United States Patent
Kim et al.

(10) Patent No.: US 11,123,409 B2
(45) Date of Patent: Sep. 21, 2021

(54) METHOD OF TREATING OR PREVENTING EYE DISEASE USING CAS9 PROTEIN AND GUIDE RNA

(71) Applicants: INSTITUTE FOR BASIC SCIENCE, Daejeon (KR); SEOUL NATIONAL UNIVERSITY R&DB FOUNDATION, Seoul (KR); SEOUL NATIONAL UNIVERSITY HOSPITAL, Seoul (KR)

(72) Inventors: Jin-Soo Kim, Seoul (KR); Jeong Hun Kim, Seoul (KR); Sung Wook Park, Seoul (KR); Kyoungmi Kim, Seoul (KR)

(73) Assignees: INSTITUTE FOR BASIC SCIENCE, Daejeon (KR); SEOUL NATIONAL UNIVERSITY R&DB FOUNDATION, Seoul (KR); SEOUL NATIONAL UNIVERSITY HOSPITAL, Seoul (KR)

( * ) Notice: Subject to any disclaimer, the term of this patent is extended or adjusted under 35 U.S.C. 154(b) by 444 days.

(21) Appl. No.: 15/661,300

(22) Filed: Jul. 27, 2017

(65) Prior Publication Data
US 2018/0078620 A1   Mar. 22, 2018

Related U.S. Application Data

(60) Provisional application No. 62/367,674, filed on Jul. 28, 2016.

(51) Int. Cl.
| | |
|---|---|
| *A61K 38/46* | (2006.01) |
| *C12N 15/11* | (2006.01) |
| *A61K 48/00* | (2006.01) |
| *C12N 15/113* | (2010.01) |
| *C12N 9/22* | (2006.01) |
| *C12N 15/10* | (2006.01) |

(52) U.S. Cl.
CPC ............ *A61K 38/465* (2013.01); *A61K 48/00* (2013.01); *C12N 9/22* (2013.01); *C12N 15/102* (2013.01); *C12N 15/11* (2013.01); *C12N 15/1136* (2013.01); *C12N 2310/20* (2017.05)

(58) Field of Classification Search
CPC ...... A61K 35/465; A61K 48/00; C12N 15/11; C12N 15/1136; C12N 15/102
See application file for complete search history.

(56) References Cited

U.S. PATENT DOCUMENTS

| | | | |
|---|---|---|---|
| 2006/0094032 A1* | 5/2006 | Fougerolles ....... | A61K 31/7088 435/6.16 |
| 2015/0376586 A1 | 12/2015 | May et al. | |
| 2016/0340661 A1* | 11/2016 | Cong .................... | A61K 48/00 |

FOREIGN PATENT DOCUMENTS

| | | | | |
|---|---|---|---|---|
| JP | 2015-177801 | 10/2015 | | |
| KR | 10-2015-0101446 | 9/2015 | | |
| KR | 10-2016-0089527 | 7/2016 | | |
| WO | 2009/111658 | 9/2009 | | |
| WO | WO-2017099494 A1 * | 6/2017 | ........... | C12N 15/113 |

OTHER PUBLICATIONS

WO 2017/0994494 translation, provided Jan. 5, 2020 (Year: 2020).*
Yanfang Fu et al, "Improving CRISPR-Cas nuclease specificity using truncated guide RNAs", Nature biotechnology vol. 32, No. 3, pp. 279-284, Mar. 2014.
Seung Woo Cho et al., "Analysis of off-target effects of CRISPR/Cas-derived RNA-guided endonucleases and nickases",Genome research 24, 132-141, Jan. 2014.
Benjamin P. Kleinstiver et al., "High-fidelity CRISPR-Cas9 nucleases with no detectable genome-wide off-target effects", Nature vol. 529, pp. 490-495, Jan. 2016.
Ian M. Slaymaker et al., "Rationally engineered Cas9 nucleases with improved specificity", Science 351, pp. 84-88 Jan. 2016.
Daesik Kim et al., "Digenome-seq: genome-wide profiling of CRISPR-Cas9 off-target effects in human cells", Nature Methods vol. 12, No. 3, pp. 237-243 Mar. 2015.
Glenn Yiu et al., "Genomic disruption of VEGF in human retinal pigment epithelial cells using CRISPR-Cas9 endonuclease", ARVO 2016 Annual Meeting Abstracts, 161 Gene editing and therapies, May 1, 2016, Program No. 1159, Poster Board No. C0009.
Taeyoung Koo et al., "Measuring and reducing off-target activities of programmable nucleases including CRISPR-Cas9", Molecules and Cells, Minireview, May 19, 2015 (online), vol. 38, No. 6, pp. 475-481.
Glenn Yiu et al., "Genomic disruption of VEGF-A expression in human retinal pigment epithelial cells using CRISPR-Cas9 endonuclease", Investigative Ophthalmology & Visual Science, Retinal Cell Biology, Aug. 2016, vol. 57, No. 13, pp. 5490-5497.
EPO, Supplementary European Search Report of EP 17834796.9 dated Mar. 18, 2020.
Glenn Yiu et al, "ARVO Meeting Abstract; Genomic Disruption of VEGF in Human Retinal Pigment Epithelial Cells using CRISPR-Cas9 Endonuclease", IOVS, May 1-5, 2016, URL: https://iovs.arvojournals.org/article.aspx?articleid=2559853&resultClick=1, (Mar. 10, 2020), XP055675266 [X] 10,14 * abstract *.
Anne Louise Askou et al., "Reduction of choroidal neovascularization in mice by adeno-associated virus-delivered anti-vascular endothelial growth factor short hairpin RNA", Journal of Gene Medicine, 14: 632-641, Nov. 1, 2012.

(Continued)

*Primary Examiner* — Antonio Galisteo Gonzalez
(74) *Attorney, Agent, or Firm* — Lex IP Meister, PLLC

(57) ABSTRACT

Provided are a method of preventing and/or treating an eye disease, using a Cas9 protein and a guide RNA targeting VEGF-A, and a ribonucleoprotein including a Cas9 protein and a guide RNA targeting VEGF-A.

3 Claims, 24 Drawing Sheets
(23 of 24 Drawing Sheet(s) Filed in Color)
Specification includes a Sequence Listing.

(56) References Cited

OTHER PUBLICATIONS

Kyoungmi Kim et al., "Genome surgery using Cas9 ribonucleoproteins for the treatment of age-related macular degeneration", Genome Research, Feb. 16, 2017.
William T. Hendriks et al., "Genome Editing in Human Pluripotent Stern Cells: Approaches, Pitfalls, and Solutions", Cell Stem Cell, (Jan. 2016), 18, [1], p. 53-65.

* cited by examiner

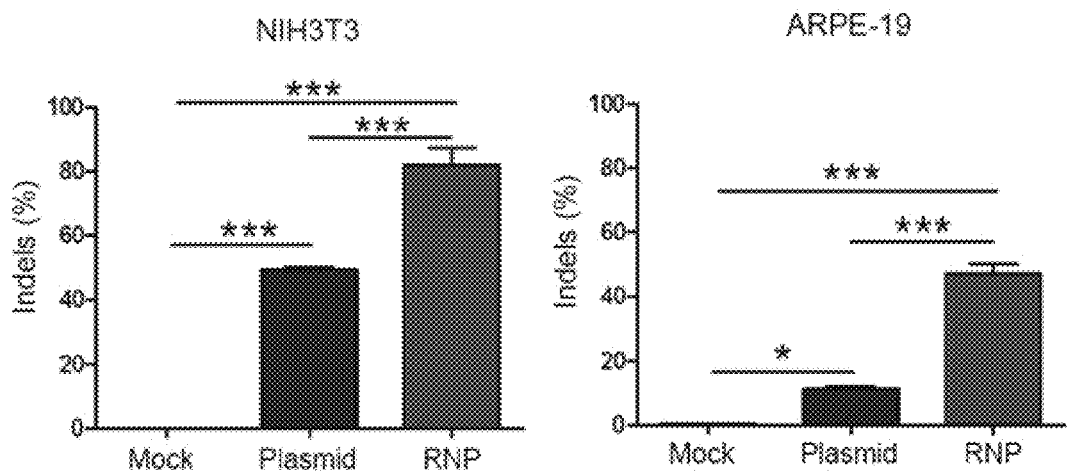

RPE in RPE/choroid/scleral complex

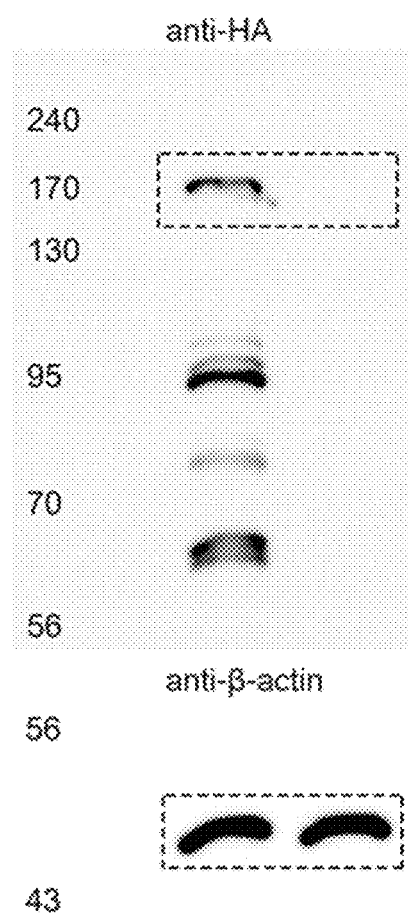

(SEQ ID NO: 293)

FIG. 5 a

Vegfa

| | | SEQ ID NO |
|---|---|---|
| CTCGTCGGGGTACTCCTGGAAGATGTCCACCAGGGTCTCAATCGGACGGC | WT | (362) |
| CTCGTCGGGGTACTCCTGGAAGATGT-------------CTCAATCGGACGGC | -10 | (374) |
| CTCGTCGGGGTACTCCTGGAAGATG-------------TCTCAATCGGACGGC | -10 | (375) |
| CTCGTCGGGGTACTCCTGG-------------AGGGTCTCAATCGGACGGC | -12 | (376) |
| CTCGTCGGGGTACTCCTGGAAGAT-------------GTCTCAATCGGACGGC | -10 | (377) |
| CTCGTCGGGGTACTCCTGGAAGATGT---CCAGGGTCTCAATCGGACGGC | -3 | (378) | b

Vegfa

| | | SEQ ID NO |
|---|---|---|
| CTCGTCGGGGTACTCCTGGAAGATGTCCA-CCAGGGTCTCAATCGGACGGC | WT | (362) |
| CTCGTCGGGGTACTCCTGGAAGATGTCCAACCAGGGTCTCAATCGGACGGC | +1 | (364) |
| CTCGTCGGGGTACTCCTGGAAGATGTC-A-CCAGGGTCTCAATCGGACGGC | -1 | (379) |
| CTCGTCGGGGTACTCCTGGAAGATGTC---CCAGGGTCTCAATCGGACGGC | -2 | (380) |
| CTCGTCGGGGTACTCCTGGAAGATGTCC--CCAGGGTCTCAATCGGACGGC | -1 | (381) |
| CTCGTCGGGGTACTCCTGGAAGATGTCCA---AGGGTCTCAATCGGACGGC | -2 | (382) |

Rosa26

| | | SEQ ID NO |
|---|---|---|
| TCCCAGGCCCAGGGCGGTCCTCAGAAGCC-AGGAGGCAGCAGAGAACTCCC | WT | (383) |
| TCCCAGGCCCAGGGCGGTCCTCAGAAGCC---GGAGGCAGCAGAGAACTCCC | -1 | (384) |
| TCCCAGGCCCAGGGCGGTCCTCAGAAGCCAGGAGGCAGCAGAGAACTCCC | +1 | (385) |
| TCCCAGGCCCAGGGCGGTCCT-------------AGGAGGCAGCAGAGAACTCCC | -8 | (386) |
| TCCCAGGCCCAGGGCGGTCCTCAGAAGC--AGGAGGCAGCAGAGAACTCCC | -1 | (387) |
| TCCCAGGCCCAGGGCGGTCCTCAGAAGC---------CAGCAGAGAACTCCC | -7 | (388) |

METHOD OF TREATING OR PREVENTING EYE DISEASE USING CAS9 PROTEIN AND GUIDE RNA

CROSS-REFERENCE TO RELATED APPLICATIONS

This application claims the benefit of U.S. Provisional Application No. 62/367,674 filed on Jul. 28, 2016 with the United States Patent and Trademark Office, the entire disclosure of which is hereby incorporated by reference.

BACKGROUND OF THE INVENTION

1. Field of the Invention

Provided are a method of treating or preventing eye disease, using a Cas9 protein and a guide RNA targeting VEGF-A, and a ribonucloprotein including a Cas9 protein and a guide RNA targeting VEGF-A.

2. Description of the Related Art

RNA-guided genome surgery or RNA-guided genome editing using CRISPR-Cas9 nuclease is expected to be helpful for the therapy of various genetic diseases, but little is known about the therapeutic effects of CRISPR-Cas9 nuclease on non-genetic diseases.

One example representative of non-genetic diseases is macular degeneration (e.g., aged-related macular degeneration (AMD)). AMD is a major cause of blindness in the elderly population in advanced countries. Choroidal neovascularization (CNV) is a main pathological feature in neovascular AMD, and is principally caused by angiogenic cytokines such as vascular endothelial growth factor A (VEGF A). So far, development has mostly been made of monoclonal antibodies or aptamers targeting VEGF-A, as therapeutic agents for AMD. However, such anti-VEGF-A are problematic in that they must be administered seven times or more a year as VEGF-A is continually expressed and secreted in retinal cells.

Therefore, there is a need for the development of a more fundamental and long-lasting therapeutic technique for eye diseases.

REFERENCE

Korean Patent No. 10-2015-0101446 A (issued on Sep. 3, 2015)

SUMMARY OF THE INVENTION

The present specification proposes a technique that allows for the long-lasting or permanent therapy of eye diseases through the fundamental inactivation of VEGF-A or by lowering the level of VEGF-A to less than a pathologic threshold.

An aspect provides a therapeutic composition for prevention and/or treatment of an eye disease, including a VEGF-A gene-inactivating agent.

The VEGF-A gene-inactivating agent may be at least one selected from the group consisting of proteins, nucleic acid molecules (DNA and/or RNA), and chemical drugs, all capable of inactivating a VEGF-A gene. In one embodiment, the VEGF-A gene-inactivating agent may include a Cas9 protein and a guide RNA targeting a VEGF-A gene.

Another aspect provides a method of preventing and/or treating an eye disease, comprising a step of inactivating a VEGF-A gene. The step of inactivating a VEGF-A gene may be carried out by a step of administering a VEGF-A gene-inactivating agent to a subject in need of prevention and/or treatment of an eye disease. The VEGF-A gene inactivation may be performed by RNA-guided genome surgery or RNA-guided genome editing. In this regard, the step of inactivating a VEGF-A gene is carried out by a step of administering a Cas9 protein and a guide RNA targeting a VEGF-A gene to a subject in need of prevention and/or treatment of an eye disease.

Another aspect provides the use of a VEGF-A gene-inactivating agent in prevention and/or treatment of an eye diseases or in preparation of a therapeutic agent for an eye disease.

Another aspect provides a guide DNA for targeting a specific target site or target region of a VEGFA gene.

Another aspect provides a VEGFA gene-specific ribonucleoprotein (RNP) including a Cas9 protein and a guide RNA having a VEGFA gene-specific targeting sequence.

Another aspect provides a pharmaceutical composition including the guide RNA or the VEGFA gene-specific RNP.

Another aspect provides a method for treatment or prevention of an eye disease, including a step of administering the VEGFA gene-specific RNP to a subject in need of treatment and/or prevention of the eye disease.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The above and other aspects, features and advantages of the present invention will be more apparent from the following detailed description taken in conjunction with the accompanying drawings, in which:

FIG. 1c shows graphs of indel frequencies induced by the delivery of either the Vegfa-specific Cas9 RNP containing the Vegfa-1 sgRNA or a plasmid carrying an encoding sequence thereof in NIH3T3 and ARPE-19 cells;

FIG. 1d shows mutant DNA sequences induced by the Vegfa-specific Cas9 RNP containing the Vegfa-1 sgRNA at the Vegfa/VEGFA locus in NIH3T3 and ARPE-19 cells;

FIG. 2i shows Cas9 protein levels in RPE/choroid/scleral complexes 24 and 72 hours post-injection, as measured by Western blot analysis;

FIG. 5 shows mutant DNA sequences induced by Vegfa-specific Cas9 RNPs (containing Vegfa-1 sgRNA) in mouse RPE, including (a) representative mutant sequences induced by the Vegfa-specific Cas9 RNP in RPE at day 3 post-injection; and (b) mutant DNA sequences in RPE containing laser-induced choroidal neovascularization (CNV) at day 7 post-injection;

DETAILED DESCRIPTION

Figure 1A:
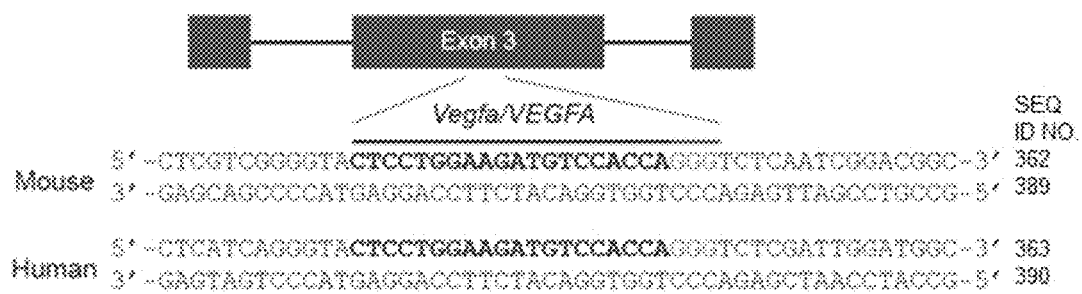
FIG. 1a shows target sequences in the Vegfa/VEGFA locus of mouse NIH3T3 and human ARPE-19 cells wherein PAM and sgRNA target sequences are shown in red and blue, respectively.

The present invention provides a technique for treating an eye disease, for example, an eye disease associated with the overexpression of VEGF-A, using a gene editing method.

An aspect provides a composition for the prevention and/or treatment of an eye disease, including a VEGF-A gene-inactivating agent. The VEGF-A gene-inactivating agent may be at least one selected from the group consisting of proteins, nucleic acid molecules (DNA and/or RNA), and chemical drugs all of which can inactivate a VEGF-A gene. In one embodiment, the VEGF-A gene-inactivating agent may include a Cas9 protein and a guide RNA targeting a VEGF-A gene.

Another aspect provides a method of preventing and/or treating an eye disease, comprising a step of in activating a VEGF-A gene. The step of inactivating a VEGF-A gene may be carried out by a step of administering a VEGF-A gene-inactivating agent to a subject in need of prevention and/or treatment of an eye disease. The VEGF-A gene inactivation may be performed by RNA-guided genome surgery or RNA-guided genome editing. In this regard, the step of inactivating a VEGF-A gene may be carried out by administering a Cas9 protein and a guide RNA targeting a VEGF-A gene to a subject in need of prevention and/or treatment of an eye disease. The method may further include a step of identifying the subject in need of prevention and/or treatment of an eye disease, prior to the administering step. The VEGF-A gene-inactivating agent may be administered in a pharmaceutically effective amount. The VEGF-A gene-inactivating agent may be administered via various routes, for example, by local administration to ocular lesions or by subretinal injection.

Another aspect provides the use of a VEGF-A gene-inactivating agent in prevention and/or treatment of an eye disease or in preparation of a therapeutic agent for an eye disease.

The VEGF-A gene to be targeted for inactivation may be located in an eye, for example, an eye having a neovascular eye disease, particularly, in a lesion site of a neovascular eye disease.

The VEGF-A gene inactivation may be at least one selected from the group consisting of:

(1) deletion of an entire sequence or a 1-50 bp or 1-40 bp long consecutive or inconsecutive partial sequence of the VEGF-A gene;

(2) substitution of 1-20, 1-15, or 1-10 consecutive or inconsecutive nucleotides in the VEGF-A gene with nucleotides different from those in a wild-type VEGF-A gene;

(3) insertion (addition) of 1-20, 1-15, or 1-10 nucleotides into the VEGF-A gene, the nucleotides to be inserted each being independently selected from among A, T, C, and G; and (4) a combination thereof.

The VEGF-A gene-inactivating agent may be at least one selected from the group consisting of proteins, nucleic acid molecules (DNA and/or RNA), and chemical drugs, all of which can inactivate a VEGF-A gene. In accordance with one embodiment, the VEGF-A gene-inactivating agent may include a Cas9 protein and a guide RNA targeting a VEGF-A gene. In this regard, the VEGF-A gene inactivation may be performed by RNA-guided genome surgery or RNA-guided genome editing.

When carried out using a Cas9 protein, the VEGF-A gene inactivation may be at least one selected from the group consisting of:

(1) deletion of at least one nucleotide positioned in a 1-50 bp- or 1-40 bp-long consecutive or inconsecutive region, adjacent to a proto-spacer-adjacent motif (PAM) sequence for a Cas9 protein, in the VEGF-A gene;

(2) substitution of 1-20, 1-15, or 1-10 consecutive or inconsecutive nucleotides positioned in 1-50 bp- or 1-40 bp-long consecutive or inconsecutive region, adjacent to a PAM sequence for a Cas9 protein, in the VEGF-A gene with nucleotides different from those in a wild-type VEGF-A gene;

(3) insertion (addition) of 1-20, 1-15, or 1-10 nucleotides into a 1-50 bp- or 1-40 bp-long consecutive or inconsecutive region, adjacent to a PAM sequence for a Cas9 protein, in the VEGF-A gene, the nucleotides to be inserted each being independently selected from among A, T, C, and G; and (4) a combination thereof.

The VEGF-A gene-inactivating agent may include a Cas protein or a coding gene thereof (DNA or mRNA); and a VEGF-A gene-specific guide RNA comprising a targeting sequence that binds specifically to a target size of a VEGF-A gene, or a coding DNA thereof.

The Cas9 protein and the VEGF-A gene-specific guide RNA may be in the form of:

(a) a complex in which the Cas9 protein is associated with the VEGF-A gene-specific guide RNA prior to administration to a body (or lesion) or cells (i.e., already assembled before administration), that is, in the form of ribonucleoprotein (RNP) (in this regard, transported in the form of RNP across cell membranes into cells or a body);

(b) a complex in which the Cas9 protein is associated with the VEGF-A gene-specific guide RNA following administration (delivery) into cells or a body by means of respective vectors carrying DNAs which respectively encode the Cas9 protein and the VEGF-A gene-specific guide RNA or one vector carrying both of the DNAs;

(c) a RNA mixture including an RNA (mRNA) coding for the Cas9 protein, and the VEGF-A gene-specific guide RNA; or (d) a mixture of a recombinant vector carrying a gene (DNA) coding for the Cas9 protein and the VEGF-A gene-specific guide RNA (e.g., obtained by in vitro transcription).

In one embodiment, the RNA mixture may be included in a typical RNA carrier for delivery into cells or a body.

Therefore, the VEGF-A gene-inactivating agent may include:

(a) a complex in which the Cas9 protein is associated with the VEGF-A gene-specific guide RNA prior to administration to a body (or lesion) or cells (i.e., already assembled before administration), that is, ribonucleoprotein (RNP) (in this regard, transported in the form of RNP across cell membranes into cells or a body);

(b) a recombinant vector carrying together genes (DNA) coding respectively for a Cas protein and a VEGF-A gene-specific guide RNA, or separate recombinant vectors respectively carrying the genes (that is, a recombinant vector carrying a gene coding for a Cas protein and a recombinant vector carrying a DNA coding for a VEGF-A gene-specific guide RNA), or a recombinant cell anchoring the recombinant(s) thereat;

(c) an RNA mixture including an RNA (mRNA) coding for a Cas9 protein and a VEGF-A gene-specific guide RNA;

(d) a mixture of a recombinant vector carrying a gene (DNA) coding for a Cas9 protein, and a VEGF-A gene-specific guide RNA (i.e., obtained by in vitro transcription); or (e) a combination thereof.

The administration of the VEGF-A gene-inactivating agent may be implemented by administering a recombinant vector carrying a gene (DNA) coding for a Cas9 protein and a recombinant vector carrying a DNA coding for a VEGF-A gene-specific guide RNA; an RNA (mRNA) coding for Cas9 protein, and a VEGF-A gene-specific guide RNA; or a recombinant carrying a gene (DNA) coding for a Cas9 protein, and a VEGF-A gene-specific guide RNA, simultaneously or sequentially irrespective of order.

Another aspect provides a guide RNA for targeting a predetermined target site or region. In one embodiment, the guide RNA may include a targeting sequence hybridizable with (i.e., a target sequence having a nucleic acid sequence complementary to) a nucleic acid sequence on one strand (e.g., a strand complementary to a strand on which a PAM sequence) of a predetermined target region in a VEGFA gene.

Another aspect provides a VEGFA gene-specific ribonucleoprotein (RNP) including a Cas9 protein and a guide RNA having a VEGFA gene-specific targeting sequence.

Another aspect provides a pharmaceutical composition including the guide RNA or the VEGFA gene-specific ribonucleoprotein (RNP). The pharmaceutical composition may be used for treating and/or preventing an eye disease such as macular degeneration (e.g., age-related macular degeneration (AMD)), retinopathy (e.g., diabetic retinopathy), etc.

Another aspect provides a method of treating or preventing an eye disease, including a step of administering the VEGFA gene-specific ribonucleoprotein (RNP) to a subject in need of treatment and/or prevention of the eye disease. The VEGFA gene-specific ribonucleoprotein (RNP) may be administered in a pharmaceutically effective amount, for example, via a topical route to an ocular lesion or by subretinal injection.

The eye disease may be an eye disease associated with the overexpression of a vascular endothelial growth factor (VEGF), for example, VEGF-A, as exemplified by a neovascular eye disease). The neovascular eye disease may be any eye disease that is caused by ocular neovascularization, for example, choroidal neovascularization (CNV) and may be selected from the group consisting of macular degeneration (e.g., age-related macular degeneration (AMD), myopic choroidal neovascularization, retinopathy (e.g., diabetic retinopathy), ischemic retinopathy, branch retinal vein occlusion, central retinal vein occlusion, and retinopathy of prematurity.

VEGF-A (vascular endothelial growth factor A) may be derived from mammals including primates such as humans, apes, and the like, and rodents such as rats, mice, etc. For example, it may be human VEGF-A (e.g., NCBI Accession No. NP_001020537, NP_001020538, NP_001020539, NP_001020540, NP_001020541, NP_001028928, NP_001165093, NP_001165094, NP_001165095, NP_001165096, NP_001165097, NP_001165098, NP_001165099, NP_001165100, NP_001165101, NP_001191313, NP_001191314, NP_001273973, NP_001303939, NP_003367, etc.), Mouse VEGF-A (NCBI Accession No. NP_001020421, NP_001020428, NP_001103736, NP_001103737, NP_001103738, NP_001273985, NP_001273986, NP_001273987, NP_001303970, NP_033531, etc.).

The Cas9 protein may be derived (isolated) from, for example, *Streptococcus pyogenes*.

As used herein, the term "target gene" refers to a gene to be targeted for gene editing (VEGF-A gene);

the term "target site" or "target region" refers to a gene site in a target gene (VEGF-A gene) in which Cas9 performs gene editing (cleavage, and deletion, addition and/or substitution of nucleotides), specifying a gene site with a maximum length of about 50 bp or 40 bp, adjacent to the 5' and/or 3' terminus of a PAM sequence recognized by Cas9 protein within the target gene (VEGF-A gene);

the term "target sequence" refers to a gene site of the target gene (VEGF-A gene), which can hybridize with a guide RNA, specifying a 17-23 bp, for example 20 bp-long nucleic acid sequence adjacent to the 5' or 3' end of a PAM sequence recognizable by Cas9 protein in the target gene; and the term "targeting sequence" is a guide RNA region hybridizable with the target sequence in the target gene and may be a guide RNA region including 17-23, for example, 20 nucleotides.

In the present specification, the target sequence is represented by a nucleic acid sequence on the PAM sequence-retaining strand of the two DNA strands in a relevant gene region of the target gene (VEGF-A gene). Indeed, because the DNA strand to which the guide RNA binds is a complementary strand to the strand on which the PAM sequence is positioned, the targeting sequence in the guide RNA has the same nucleic acid sequence as the target sequence in the target gene (VEGF-A gene) except that T is changed into U in consideration of the RNA characteristic. Therefore, herein, a sequencing sequence of the guide RNA and a target sequence of the target gene (VEGF-A gene) are represented by the same nucleic acid sequence with the exception that T and U are interchanged.

When the Cas9 protein is derived from *Streptococcus pyogenes*, the PAM sequence is 5'-NGG-3' (wherein N is A, T, G, or C), and the target region is a gene region adjacent to the 5' terminus and/or 3' terminus of the 5'-NGG-3' sequence in the target gene (VEGF-A gene), and may be, for example, a gene region about 50 bp or about 40 bp long.

In this regard, the VEGF-A gene inactivation may be induced in a VEGF-A gene by:

a) deletion of at least one nucleotide from a nucleic acid sequence (target region) that is up to 50 bp or up to 40 bp in length and which is adjacent to the 5' and/or 3' terminus of a 5'-NGG-3' sequence (wherein N is A, T, C, or G), b) substitution of at least one nucleotide (e.g., 1-20, 1-5, or 1-10 nucleotides) in a nucleic acid sequence (target site) which is up to 50 bp or up to 40 bp long and adjacent to the 5' and/or 3' terminus of a 5'-NGG-3' sequence, with a nucleotide different from a corresponding one in a wild-type gene, c) insertion of at least one nucleotide (for example, 1-20, 1-5, or 1-10 nucleotides) into a nucleic acid sequence (target site) which is up to 50 bp or up to 40 bp long and adjacent to the 5' and/or 3' terminus of a 5'-NGG-3' sequence (for this, nucleotides to be inserted are each independently selected from among A, T, C, and G), or d) a combination of two or more of a) to c).

The guide RNA may be at least one selected from the group consisting of a CRISPR RNA (crRNA), a trans-activating crRNA (tracrRNA), and a single guide RNA (sgRNA). In detail, the guide DNA may be a dual crRNA: tracrRNA complex in which a crRNA and a tracrRNA are combined with each other, or a single guide RNA (sgRNA) in which a crRNA or a part thereof is connected to a tracrRNA or a part thereof via an oligonucleotide linker.

The concrete sequence of the guide RNA may be suitably selected depending on kinds of Cas9 protein (that is, microorganisms from which the guide RNA is derived), and is a matter that a person skilled in the art could easily establish.

When a *Streptococcus pyogenes*—derived Cas9 protein is used, the crRNA may be an oligonucleotide wherein a targeting sequence represented by $(N_{cas9})_l$, GUUUUA-GAGCUA) (SEQ ID NO: 359), and $(X_{cas9})_m$ are arranged in order from 5' terminus to 3' terminus thereof:

wherein, $N_{cas9}$ is a targeting sequence which is determined depending on a target sequence in a target gene (VEGF-A gene), I represents a number of nucleotides contained in the targeting sequence and may be an integer of 17 to 23, or 18 to 22, for example, 20;

a region including the 12 consecutive nucleotides (GUUUUAGAGCUA) (SEQ ID NO: 359) adjacent to the 3' terminus of the target sequence is an indispensable part of the crRNA; and $X_{cas9}$ is a region including m nucleotides positioned at the 3' terminus of the crRNA (that is, adjacent to the 3' terminal of the indispensable part of the crRNA), and m may be an integer of 8 to 12, for example 11, and the m nucleotides, which may be the same or different, may each be independently selected from the group consisting of A, U, C, and G.

In one embodiment, $X_{cas9}$ may include, but is not limited to, UGCUGUUUUG (SEQ ID NO: 360).

Further, the tracrRNA may be an oligonucleotide wherein $(Y_{cas9})_p$ and (UAGCAAGUUAAAAUAAGGCUAGU-CCGUUAUCAACUUGAAAAAGUGGCACCGAG UCG-GUGC) (SEQ ID NO: 361) are arranged in order from 5' terminus to 3' terminus thereof:

wherein, a region consisting of 60 nucleotides (UAGCAAGUUAAAAUAAGGCUAGUCCGUUAU-CAACUUGAAAAAGUGGCACCGAG UCGGUGC) (SEQ ID NO: 361) is an indispensable part of the tracrRNA, and $Y_{cas9}$ is a region including p nucleotides adjacent to the 5' terminus of the indispensable part of the tracrRNA, p may be an integer of 6 to 20, for example, 8 to 19, and the p nucleotides, which may be the same or different, may each be independently selected from the group consisting of A, U, C, and G.

The sgRNA may be in a form of a hairpin (stem-loop structure) in which a crRNA moiety including the targeting sequence and the indispensable part of the crRNA and a tracrRNA moiety including the indispensable part (60 nucleotides) of the tracrRNA is connected via an oligonucleotide linker (in this regard, the oligonucleotide linker accounts for the loop structure). In greater detail, the sgRNA has a hairpin structure in which a crRNA moiety including the targeting sequence and indispensable part of the crRNA and a tracrRNA moiety including the indispensable part of the tracrRNA are combined each other, with connection between the 3' terminus of the crRNA moiety and the 5' terminus of the tracrRNA moiety via an oligonucleotide linker.

In one embodiment, the sgRNA may be an oligonucleotide wherein $(N_{cas9})_l$, (GUUUUAGAGCUA) (SEQ ID NO: 359), an oligonucleotide linker, and (UAGCAAGUUAAAAUAAGGCUAGUCCGUUAU-CAACUUGAAAAAGUGGCACCGAG UCGGUGC) (SEQ ID NO: 361) are arranged in order from 5' terminus to 3' terminus thereof:

wherein $(N_{cas9})_l$ is a target sequence as defined above.

The oligonucleotide linker included in the sgRNA may be a sequence consisting of three to five, for example, four nucleotides which may be the same or different and each be independently selected from the group consisting of A, U, C, and G.

The crRNA or the sgRNA may further include one to three guanines (G) at the 5' terminus (that is, the 5' terminus of the targeting sequence in the crRNA).

The tracrRNA or the sgRNA may further include a terminal region including five to seven uracil residues at the 3' terminus of the indispensable part (60 nt) of the tracrRNA.

In one embodiment, the target sequence in the target gene (VEGF-A gene) may be selected from the group consisting of:

```
Vegfa-1:
                                          (SEQ ID NO: 1)
5'-CTCCTGGAAGATGTCCACCA-3' (PAM sequence: GGG);

Vegfa-2:
                                          (SEQ ID NO: 2)
5'-AGCTCATCTCTCCTATGTGC-3' (PAM sequence: TGG);

Vegfa-3:
                                          (SEQ ID NO: 3)
5'-GACCCTGGTGGACATCTTCC-3' (PAM sequence: AGG);

Vegfa-4:
                                          (SEQ ID NO: 4)
5'-ACTCCTGGAAGATGTCCACC-3' (PAM sequence: AGG);

Vegfa-5:
                                          (SEQ ID NO: 5)
5'-CGCTTACCTTGGCATGGTGG-3' (PAM sequence: AGG);

Vegfa-6:
                                          (SEQ ID NO: 6)
5'-GACCGCTTACCTTGGCATGG-3' (PAM sequence: TGG);

Vegfa-7:
                                          (SEQ ID NO: 7)
5'-CACGACCGCTTACCTTGGCA-3' (PAM sequence: TGG);
and Vegfa-8:
                                          (SEQ ID NO: 8)
5'-GGTGCAGCCTGGGACCACTG-3' (PAM sequence: AGG).
```

These target sequences are well conserved among species and exist in, for example, both humans and rodents (e.g., mice). By way of example, the target sequence may include the nucleotide sequence of SEQ ID NO: 1 or SEQ ID NO: 2.

The target sequences are well conserved among mammals, for example, between human VEGF-A genes and mouse VEGF-A genes, and exhibit highly outstanding gene editing efficiency (e.g., indel frequency (%)) for on-target sites, and have 3 or less, 2 or less, 1, or no mismatching nucleotides in sites (off-target sites) other than the on-target sites. Thus, there is little or no probability of gene editing in sites other than the on-target sites, and the target sequences are of excellent safety (very low or almost no off-target effects)

On the basis of the outstanding editing efficiency and low off-target effect, an aspect of the present invention provides a composition for editing a VEGF-A gene, including the guide RNA or a DNA coding for the guide RNA, and a Cas9 protein or a gene (DNA or mRNA) coding for the Cas9 protein. The composition for editing a VEGF-A gene may include a ribonucleoprotein which contains the guide RNA and the Cas9 protein. In this regard, the ribonucleoprotein may be assembled prior to administration to a body or cells.

Herein, the targeting sequence of guide RNA hybridizable with the target region of the target gene means a nucleotide sequence having a sequence complementarity of 50% or higher, 60% or higher, 70% or higher, 80% or higher, 90% or higher, 95% or higher, 99% or higher, or 100% to a nucleotide sequence on a strand complementary to a DNA strand on which a target sequence is located (that is, a DNA strand on which a PAM sequence exists), and thus can complementarily bind to the nucleotide sequence on the complementary strand.

For example, the targeting sequence $(N_{cas9})_l$ of crRNA or sgRNA may have the same sequence as one of the target sequences of SEQ ID NOS: 1 to 4 (provided that T is changed with U). This is, $(N_{cas9})_l$ in crRNA or sgRNA may include a targeting sequence selected from among the sequences of SEQ ID NOS: 9 to 16:

```
Vegfa-1:
                                          (SEQ ID NO: 9)
5'-CUCCUGGAAGAUGUCCACCA-3';

Vegfa-2:
                                          (SEQ ID NO: 10)
5'-AGCUCAUCUCUCCUAUGUGC-3';

Vegfa-3:
                                          (SEQ ID NO: 11)
5'-GACCCUGGUGGACAUCUUCC-3';

Vegfa-4:
                                          (SEQ ID NO: 12)
5'-ACUCCUGGAAGAUGUCCACC-3';

Vegfa-5:
                                          (SEQ ID NO: 13)
5'-CGCUUACCUUGGCAUGGUGG-3';

Vegfa-6:
                                          (SEQ ID NO: 14)
5'-GACCGCUUACCUUGGCAUGG-3';

Vegfa-7:
                                          (SEQ ID NO: 15)
5'-CACGACCGCUUACCUUGGCA-3';
and Vegfa-8:
                                          (SEQ ID NO: 16)
5'-GGUGCAGCCUGGGACCACUG-3'.
```

For example, the crRNA or the sgRNA may include SEQ ID NO: 9 or 10 as a targeting sequence.

In one embodiment, a modified RNA may be employed in order to solve the problem of lowering cell viability upon RNA delivery to bodies or cells. By way of example, an RNA which is modified so as to retain no phosphate-phosphate bonds at the 5 terminus thereof (e.g., no 5'-terminal triphosphate or diphosphate) may be used as a guide RNA. Another example is an sgRNA (e.g., chemically synthesized sgRNA) which contains one or more (e.g., one to five, or two to four) modified ribonucleic acids at the 5' and/or 3' terminus thereof. In this regard, the modification may be expressed as phosphorothioate or may include a modification at the 2' position of the ribose moiety (e.g., 2'-acetylation, 2'-methylation, etc.). In one embodiment, the modified sgRNA may include methylation (methyl group addition) at the 2'-0 position of the ribose moiety on three nucleotides at each of the 5'-terminus and 3'-terminus and/or a phosphorothioate backbone modification.

Another aspect provides a guide RNA including a target sequence selected from among the sequences of SEQ ID NOS: 1 to 4.

In the method, the transduction of the guide RNA and the Cas9 protein into cells may be performed by directly introducing a pre-assembled complex (ribonucleoprotein) of the guide RNA and the Cas9 protein into cells with the aid of a conventional technique (e.g., electroporation, lipofection, etc.) into immune cells or one vector (e.g., plasmid, viral vector, etc.) carrying both a guide RNA-encoding DNA molecule and a Cas9 protein-encoding gene (DNA or mRNA) (or a gene having a sequence homology of 80% or greater, 85% or greater, 90% or greater, 96% or greater, 97% or greater, 98% or greater, or 99% or greater thereto) or respective vectors carrying the DNA molecule or the gene into cells or through mRNA delivery.

In one embodiment, the vector may be a viral vector. The viral vector may be selected from the group consisting of negative-sense single-stranded viruses (e.g., influenza virus) such as retrovirus, adenovirus, parvovirus (e.g., adeno-associated virus (AAV)), corona virus, and orthomyxovirus; positive-sense single-stranded RNA viruses such as rhabdovirus (e.g., rabies virus and vesicular stomatitis virus), paramyxovirus (e.g., measles virus and sendai virus), alphavirus, and picornavirus; and double-stranded DNA viruses such as herpes virus (e.g., herpes simplex virus type 1 and 2, Epstein-Barr virus, cytomegalovirus), and adenovirus; poxvirus (e.g., vaccinia); fowlpox; and canarypox.

A vector carrying the Cas9 protein, the guide RNA, a ribonucleoprotein containing both of them, or at least one thereof may be delivered into a body or cells, using a suitable one of well-known techniques such as electroporation, lipofection, viral vector, nanoparticles, and PTD (protein translocation domain) fusion protein.

The Cas9 protein and/or guide RNA may further include a typically useful nuclear localization signal (NLS) for the intranuclear translocation of the Cas9 protein, the guide RNA, or the ribonucleoprotein containing both of them.

In the VEGF-A gene-specific ribonucleoprotein, the Cas9 protein may be isolated from microorganisms, or non-naturally occurring in a recombinant or chemically synthetic manner while the guide RNA may be produced in a recombinant manner or chemically.

A VEGF-A gene-inactivating agent or VEGF-A gene-specific ribonucleoprotein including a Cas9 protein and a gene (DNA or mRNA) encoding the protein, and a gene-specific guide RNA containing a targeting sequence specifically binding to a target region of a VEGF-A gene or a DNA encoding the RNA may be administered into a body via various routes including, but not limited to, a topical route and a subretinal route to a lesion of an eye disease (associated with VEGF-A gene overexpression).

Examples of a subject to be administered with the VEGF-A gene-inactivating agent or the VEGF-A gene-specific ribonucleoprotein include all animals, selected from mammals, for example, primates such as humans, apes, etc., and rodents such as mice, rats, etc., which suffer from or are at the risk of a VEGF-A gene overexpression-associated eye disease, cells (e.g., retinal pigment epithelial cells (RPE), RPE/choroid/scleral complex, etc.,) and tissues (eye tissues) isolated from the animals, and a culture of the cells or tissues.

The VEGF-A gene-inactivating agent or the VEGF-A gene-specific ribonucleoprotein may be administered in a "pharmaceutically effective amount" or contained in a "pharmaceutically effective amount" in a pharmaceutical composition. As used herein, the term "pharmaceutically effective amount" refers to an amount that can elicit a desirable effect, that is, a VEGF-A gene editing effect in an application region, and may be determined depending on various factors including the age, body weight, sex, and health state of the patient, the time and route of administration, excretion rate, and sensitivity to a drug.

Ensuring not only high gene editing efficiency, but also very low off-target effects, the VEGF-A gene editing technology suggested herein can perform gene editing effectively and safely whereby a VEGF-A protein level can be reduced to less than a pathological threshold, with the consequent long or permanent therapy of a VEGF-A overexpression-associated eye disease.

Examples

Hereafter, the present invention will be described in detail by examples.

The following examples are intended merely to illustrate the invention and are not construed to restrict the invention.

REFERENCE EXAMPLE

1. Preparation of Cas9 RNP

A purified Cas9 protein was purchased from ToolGen Inc., South Korea. sgRNAs were produced by in vitro transcription using a T7 polymerase (New England Biolabs) according to the manufacturer's protocol. In brief, templates for the sgRNAs were prepared by annealing and extending sets of two complementary oligonucleotides (see Table 1).

TABLE 1

In vitro transcription templates encoding sgRNAs

| sgRNA name | RGEN Target (5' to 3') |
|---|---|
| Vegfa-1 (Forward) | GAAATTAATACGACTCACTATAGCTCCTGGAAGATGTCCACCAGTTTTAG AGCTAGAAATAGCAAG (SEQ ID NO: 17) |
| Vegfa-2 (Forward) | GAAATTAATACGACTCACTATAGAGCTCATCTCTCCTATGTGCGTTTTAG AGCTAGAAATAGCAAG (SEQ ID NO: 18) |
| Vegfa-3 (Forward) | GAAATTAATACGACTCACTATAGGACCCTGGTGGACATCTTCCGTTTTAG AGCTAGAAATAGCAAG (SEQ ID NO: 19) |

TABLE 1-continued

In vitro transcription templates encoding sgRNAs

| sgRNA name | RGEN Target (5' to 3') |
|---|---|
| Vegfa-4 (Forward) | GAAATTAATACGACTCACTATAG<u>ACTCCTGGAAGATGTCCACC</u>GTTTTAG AGCTAGAAATAGCAAG (SEQ ID NO: 20) |
| Rosa 26 (Forward) | GAAATTAATACGACTCACTATAG<u>GGCGGTCCTCAGAAGCCAGG</u>GTTTTA GAGCTAGAAATAGCAAG (SEQ ID NO: 21) |
| Universal (Reverse) | AAAAAAGCACCGACTCGGTGCCACTTTTTCAAGTTGATAACGGACTAGC CTATTTTAACTTGCTATTTCTAGCTCTAAAAC (SEQ ID NO: 22) |

(target sequences: underlined; indispensable parts of crRNA: bold; nucleotide linkers: italicized)

Each of the prepared sgRNA templates was added, together with a T7 RNA polymerase, to a reaction buffer (40 mM Tris-HCl, 20 mM $MgCl_2$, 2 mM spermidine, 1 mM DTT, pH7.9) including NTPs (Jena bioscience) and an RNase inhibitor (New England Biolabs), and incubated at 37° C. for 16 hours for transcription. The sgRNA transcripts were incubated at 37° C. for 30 min with DNase I (New England Biolabs). The sgRNAs were purified using RNeasy MinElute Cleanup Kit (Qiagen) and quantified using Nano drop (Thermo Fisher Scientific). The purified sgRNAs (65 µg) were incubated, together with CIP (Calf intestinal; 1000 units; Alkaline Phosphatase, New England Biolabs), at 37° C. for 1 hour to remove the 3-phosphoric acid group. The resulting sgRNAs were again purified using RNeasy MinElute Cleanup Kit (Qiagen) and quantified using Nano drop (Thermo Fisher Scientific).

All the Cas9 proteins and the sgRNA stocks were assayed for cell viability and gene editing (indel) efficiency. Based on the assay, selection was made of Cas9 proteins and sgRNA stocks that exhibited high efficiency for use in in vivo eye injection.

2. Cas9 Protein Purification

Figure 8:
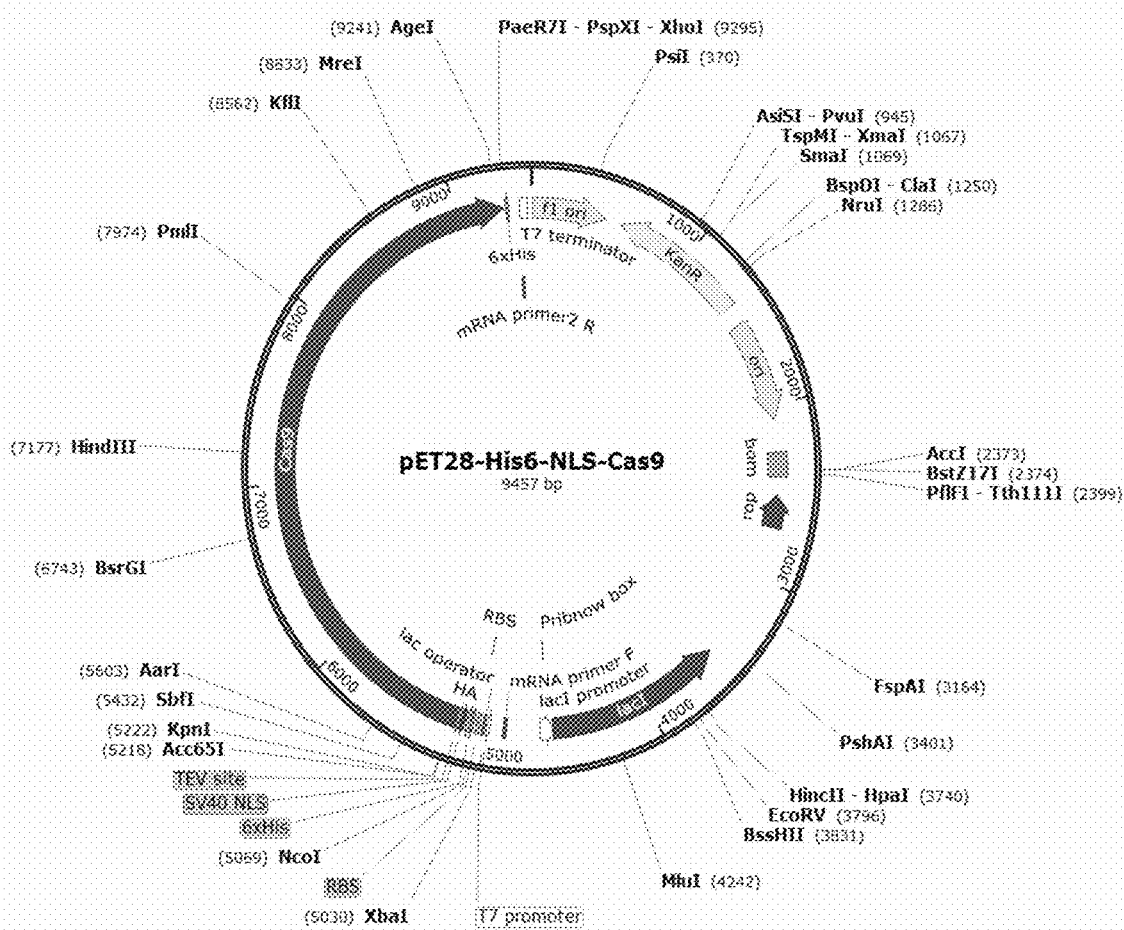
FIG. 8 is a cleavage map of a pET28-NLS-Cas9 vector.

A pET28-NLS-Cas9 vector (FIG. 8; Cas9: Streptococcus pyogenes derived (SEQ ID NO: 358)) was transformed into the E coli strain BL21 (DE3) which was then treated at 18° C. for 12 hours with 0.5 mM isopropyl β-D-1-thiogalactopyranoside (IPTG) to induce the expression of the Cas9 protein. The E. coli cells were lysed by ultrasonication and centrifuged at 20,000 g for 30 min. The soluble lysate thus obtained was mixed with Ni-NTA beads (Qiagen) and added with Cy3 dye (GE Healthcare) at a ratio of 1:10 (Cas9 protein: Cy3 dye molecule). The mixture was incubated overnight (12 hours or longer) at 4° C. in a dark condition. Cy3-labeled Cas9 was eluted with elution buffer (50 mM Tris-HCl [pH 7.6], 150-500 mM NaCl, 10-25% (w/v) glycerol, 0.2 M imidazole), and dialyzed against dialyzing buffer (20 mM HEPES pH 7.5, 150 mM KCl, 1 mM DTT, 10% (w/v) glycerol). The purified Cy3-labeled Cas9 protein was concentrated using an Ultracel 100K cellulose column (Millipore). The Cy3-labeled Cas9 protein was measured for purity by SDS-PAGE. Cy3 labeling efficiency was determined by comparing absorption spectra of the Cas9 protein (280 nm) and the conjugated Cy3 dye molecule.

3. Cell Culture and Transfection

Mouse NIH3T3 (ATCC® CRL-1658™) and ARPE-19 (human retinal pigment endothelial cell; ATCC® CRL-2302™) cell lines were cultured in Dulbecco's Modified Eagle Medium (DMEM) supplemented with 10% (v/v) BCS or FBS at 37° C. under a humidified 5% $CO_2$ atmosphere (NIH3T3 and ARPE-19 cells had not been authenticated or tested for mycoplasma contamination). One day before transfection, NIH3T3 and ARPE-19 cells were seeded into 24-well plates at a cell density of $2 \times 10^4$ cells/well, with each well containing 250 µl of an antibiotic-free growth medium.

Figure 9:
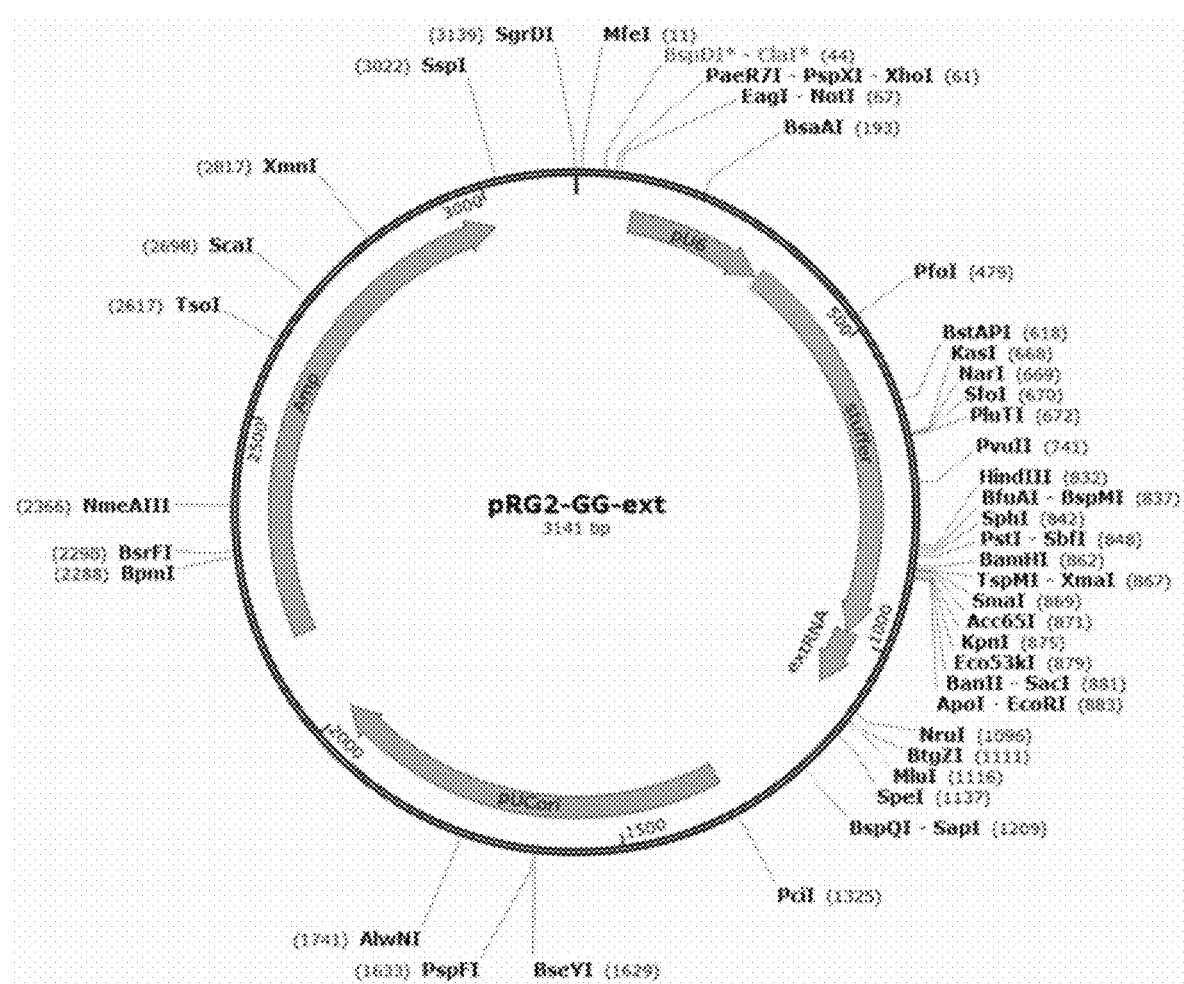
FIG. 9 is a cleavage map of a pRG2 vector.

For plasmid delivery, the cells in the 24-well plates were transfected with a Cas9 (1 µg; Streptococcus pyogenes derived; coding sequence (4107 bp): SEQ ID NO: 358) expression plasmid (pET vector (Addgene) used) and an sgRNA (1 µg; Example 1) expression plasmid (pRG2 vector (see FIG. 9) used), using Lipofectamine 2000 (Thermo Fisher Scientific) according to the manufacturer's protocol.

For RNP delivery, Cas9 protein (4 µg; Example 2) was incubated with sgRNA (2.25 µg; Example 1) at room temperature for 5 min, followed by adding 50 µl of Opti-MEM (Thermo Fisher Scientific) and 1 µl of Lipofectamine 2000 (Thermo Fisher Scientific). After 10 minutes, the RNP mixture was added to the 24-well plates and transfected into the cells. The cells were harvested 48 hours after transfection and subjected to T7E1 assay, targeted deep sequencing, and qPCR.

For VEGF-A expression in confluent RPE (human retinal pigment epithelial) cells, the prepared ARPE-19 cells were grown to confluency and then maintained in a 1% (v/v) FBS-supplemented DMEM/F12 to allow the formation of a polarized epithelial layer for experiments. ARPE-19 cells were added to 12-well plates and transfected with 8 µg of Cas9 protein, 4.5 µg of sgRNA, and 3 µl of Lipofectamine 2000. Two days after transfection, the transfection growth medium (DMEM+1% (v/v) FBS) was replaced with 0.5 ml of fresh serum-free medium. After 16 hours, cells and media were harvested and analyzed using targeted deep sequencing, qPCR, and ELISA.

4. Cy3-Labeled Cas9 RNP Imaging and Counting

One day after transfection, cells were fixed in 4% (w/v) PFA (paraformaldehyde) for 10 min at room temperature and then stained with 4', 6-diamidino-2-phenylindole (DAPI, 1 µg/ml, Sigma Aldrich) for 15 min at room temperature. The cells were visualized with a confocal microscope (LSM510, Carl Zeiss) at a magnification of x630. The scanning parameters were as follows: scaling (x=0.14 µm/pixel, y=0.14 µm/pixel, z=1 µm/pixel), dimensions (x=1024, y=1024, z=6, channels: 3, 12-bit) (with objective C-Apochromat 63x/1.20W Korr UV—VIS-IR). Cy3 positive nuclei were counted using ZEN 2 software (black edition, Ver 10.0, Carl Zeiss). In order to quantify the frequency of Cy3 positive nuclei, a total number of cells and a number of cells with Cy staining in the nucleus were counted in a field of view at a magnification of x630 and an average percentage of Cy3 positive nuclei over four fields of view were calculated (n=3).

5. T7E1 Assay

Genomic DNA was isolated from cells and tissues using a DNeasy Tissue Kit (Qiagen) according to the manufacturer's protocol. After target sites were amplified using PCR, the products were denatured and annealed using a thermal cycler. The primers used are summarized in Table 2, below.

TABLE 2

List of primers used for the T7E1 assay.

| Target | 1st PCR | | 2nd PCR | |
|---|---|---|---|---|
| | Forward (5' to 3') | Reverse (5' to 3') | Forward (5' to 3') | Reverse (5' to 3') |
| Vegfa-1 (mouse) | CAAATCT GGGTGGC GATAGA (SEQ ID NO: 23) | AGATGGTCA AATCGTGGA GAG (SEQ ID NO: 24) | ACACTCTTT CCCTACACG ACGCTCTTC CGATCTCAA ATCTGGGTG GCGATAGA (SEQ ID NO: 25) | GTGACTGG AGTTCAGA CGTGTGCT CTTCCGAT CTCCAGGG CTTCATCG TTACA (SEQ ID NO: 26) |
| Vegfa-1 (human) | CATCGTG TGATCTCT GGAATGA A (SEQ ID NO: 27) | CCCAAAGTG CCACCTGTT TTA (SEQ ID NO: 28) | ACACTCTTT CCCTACACG ACGCTCTTC CGATCTGTG GTGAAGTTC ATGGATGTC TA (SEQ ID NO: 29) | GTGACTGG AGTTCAGA CGTGTGCT CTTCCGAT CTAAAGAT GCCCACCT GCAT (SEQ ID NO: 30) |

Annealed PCR products were incubated with T7 endonuclease I (ToolGen, Inc.) at 37° C. for 25 min and analyzed by agarose gel electrophoresis.

6. Targeted Deep Sequencing

Using Phusion polymerase (Thermo Fisher Scientific), on-target and potential off-target regions were amplified from genomic DNA. The PCR amplicons were subjected to paired-end sequencing using Illumina MiSeq (LAS Inc. Korea). The primers used are listed in Tables 3 to 5:

TABLE 3

List of primers used for targeted deep sequencing

| Target | 1st PCR | | 2nd PCR | |
|---|---|---|---|---|
| | Forward (5' to 3') | Reverse (5' to 3') | Forward (5' to 3') | Reverse (5' to 3') |
| Vegfa-1 (mouse) | CAAATCTGG GTGGCGATA GA (SEQ ID NO: 23) | AGATGGTCA AATCGTGGA GAG (SEQ ID NO: 24) | ACACTCTTTCCC TACACGACGCT CTTCCGATCTCA AATCTGGGTGG CGATAGA (SEQ ID NO: 25) | GTGACTGGAG TTCAGACGTGT GCTCTTCCGAT CTCCAGGGCTT CATCGTTACA (SEQ ID NO: 26) |
| Vegfa-2 (mouse) | ACCTATCCC TGCTCAGTA GAA (SEQ ID NO: 31) | CCCAAGAGA GGAAGCAAG AA (SEQ ID NO: 32) | ACACTCTTTCCC TACACGACGCT CTTCCGATCTAT CTGCTCCCTCC CTCTAC (SEQ ID NO: 33) | GTGACTGGAG TTCAGACGTGT GCTCTTCCGAT CTGTCCATCAC CATCACCACCA CCAC (SEQ ID NO: 34) |
| Vegfa-3 (mouse) | CAAATCTGG GTGGCGATA GA (SEQ ID NO: 23) | AGATGGTCA AATCGTGGA GAG (SEQ ID NO: 24) | ACACTCTTTCCC TACACGACGCT CTTCCGATCTCA AATCTGGGTGG CGATAGA (SEQ ID NO: 25) | GTGACTGGAG TTCAGACGTGT GCTCTTCCGAT CTCCAGGGCTT CATCGTTACA (SEQ ID NO: 26) |

TABLE 3-continued

List of primers used for targeted deep sequencing

| Target | 1st PCR Forward (5' to 3') | 1st PCR Reverse (5' to 3') | 2nd PCR Forward (5' to 3') | 2nd PCR Reverse (5' to 3') |
|---|---|---|---|---|
| Vegfa-4 (mouse) | CAAATCTGG GTGGCGATA GA (SEQ ID NO: 23) | AGATGGTCA AATCGTGGA GAG (SEQ ID NO: 24) | ACACTCTTTCCC TACACGACGCT CTTCCGATCTCA AATCTGGGTGG CGATAGA (SEQ ID NO: 25) | GTGACTGGAG TTCAGACGTGT GCTCTTCCGAT CTCCAGGGCTT CATCGTTACA (SEQ ID NO: 26) |
| Vegfa-1 (human) | CATCGTGTG ATCTCTGGA ATGAA (SEQ ID NO: 27) | CCACCTGTT CCCAAAGTG TTA (SEQ ID NO: 28) | ACACTCTTTCCC TACACGACGCT CTTCCGATCTGT GGTGAAGTTCAT GGATGTCTA (SEQ ID NO: 29) | GTGACTGGAG TTCAGACGTGT GCTCTTCCGAT CTAAAGATGCC CACCTGCAT (SEQ ID NO: 30) |
| Rosa26 (mouse) | CCAAAGTCG CTCTGAGTT GT (SEQ ID NO: 35) | TCGGGTGAG CATGTCTTTA ATC (SEQ ID NO: 36) | ACACTCTTTCCC TACACGACGCT CTTCCGATCTCC AAAGTCGCTCT GAGTTGT (SEQ ID NO: 37) | GTGACTGGAG TTCAGACGTGT GCTCTTCCGAT CTCTTTAAGCC TGCCCAGAAG (SEQ ID NO: 38) |

TABLE 4

List of primers used for targeted deep sequencing at potential off target sites

| No. | 1st PCR Forward (5' to 3') | 1st PCR Reverse (5' to 3') | 2nd PCR Forward (5' to 3') | 2nd PCR Reverse (5' to 3') |
|---|---|---|---|---|
| OT1 | TCTGTCTGTC TCCAGACATT TG (SEQ ID NO: 39) | GTCCTGCTTCT ATCCTGCTTTA (SEQ ID NO: 40) | ACACTCTTTCC CTACACGACG CTCTTCCGATC TGTGATCAGCT GACTTCCAGTT C (SEQ ID NO: 41) | GTGACTGGAG TTCAGACGTGT GCTCTTCCGAT CTCTCCACAAC TCAAGTCCCAT TAC (SEQ ID NO: 42) |
| OT2 | GACGTGAGA GTGAGCAGTT TAT (SEQ ID NO: 43) | ACAGCACCCA GATTGTCTTC (SEQ ID NO: 44) | ACACTCTTTCC CTACACGACG CTCTTCCGATC TCCTTGTGTCC TTTGATGCTCT (SEQ ID NO: 45) | GTGACTGGAG TTCAGACGTGT GCTCTTCCGAT CTAAGGTCTGC ACCATGAATCC (SEQ ID NO: 46) |
| OT3 | GCTGTGCTCA AGACCAACAA (SEQ ID NO: 47) | CCGGTTCTGTA CTGGTGTCT (SEQ ID NO: 48) | ACACTCTTTCC CTACACGACG CTCTTCCGATC TTTGCCTACCT CCACCTTCT (SEQ ID NO: 49) | GTGACTGGAG TTCAGACGTGT GCTCTTCCGAT CTAGATGCTGC CCTACATGAAC (SEQ ID NO: 50) |
| OT4 | GTAGGCTCAA CAGCTCTTTC T (SEQ ID NO: 51) | CATAGTGTGAG TGGTACTGGTG (SEQ ID NO: 52) | ACACTCTTTCC CTACACGACG CTCTTCCGATC TCCTGAGCTTC CTCTGTCCTAA T (SEQ ID NO: 53) | GTGACTGGAG TTCAGACGTGT GCTCTTCCGAT CTGCCACTGCT TCTCCTCTCTA T (SEQ ID NO: 54) |
| OT5 | GCCCAAAGTA GCAGGTGATT A (SEQ ID NO: 55) | CTCAGGCTGTA ACTGACGATAT G (SEQ ID NO: 56) | ACACTCTTTCC CTACACGACG CTCTTCCGATC TACAGGATGCA AGTCCACATC (SEQ ID NO: 57) | GTGACTGGAG TTCAGACGTGT GCTCTTCCGAT CTCATTCTTCA CAGGGCCATC A (SEQ ID NO: 58) |

TABLE 4-continued

List of primers used for targeted deep sequencing at potential off target sites

| No. | 1st PCR Forward (5' to 3') | 1st PCR Reverse (5' to 3') | 2nd PCR Forward (5' to 3') | 2nd PCR Reverse (5' to 3') |
|---|---|---|---|---|
| OT6 | AGAAGCTAAGGAGCCCAATTT (SEQ ID NO: 59) | TACTTTGCCAAGCCCATGT (SEQ ID NO: 60) | ACACTCTTTCCCTACACGACGCTCTTCCGATCTGCCTTCTCTCTTGGCTGTAA (SEQ ID NO: 61) | GTGACTGGAGTTCAGACGTGTGCTCTTCCGATCTGAACCTACTCTCATCGTGCTAC (SEQ ID NO: 62) |
| OT7 | GAGGAGCCCAAGTATATCACAG (SEQ ID NO: 63) | GGTCACCATAGCTACAAGAGAG (SEQ ID NO: 64) | ACACTCTTTCCCTACACGACGCTCTTCCGATCTAAGGCTCCATTAGCCTCTTC (SEQ ID NO: 65) | GTGACTGGAGTTCAGACGTGTGCTCTTCCGATCTCTGTCATGGTGCACATCATTC (SEQ ID NO: 66) |
| OT8 | CCCTGCAGCATTCTCTGTAT (SEQ ID NO: 67) | GACCCAGTGTATTGTGGGTAG (SEQ ID NO: 68) | ACACTCTTTCCCTACACGACGCTCTTCCGATCTTGACAAGCCTGACAGTTCATC (SEQ ID NO: 69) | GTGACTGGAGTTCAGACGTGTGCTCTTCCGATCTGGCTGATGGTGAGCAGAAA (SEQ ID NO: 70) |
| OT9 | CTGGAACCAGAGTCATAGATAGTTG (SEQ ID NO: 71) | TCTGAAGCACACACCAGAAG (SEQ ID NO: 72) | ACACTCTTTCCCTACACGACGCTCTTCCGATCTCAAGATACCAAAGCAGGTGTTC (SEQ ID NO: 73) | GTGACTGGAGTTCAGACGTGTGCTCTTCCGATCTGAAGCAGTTCAGAGGTCTATGT (SEQ ID NO: 74) |
| OT10 | CTAGAAGAAGGCAGAGGGAGTA (SEQ ID NO: 75) | AGGAGGGACAGACTGGTATAAA (SEQ ID NO: 76) | ACACTCTTTCCCTACACGACGCTCTTCCGATCTCACAGCGAGCCAGAATACA (SEQ ID NO: 77) | GTGACTGGAGTTCAGACGTGTGCTCTTCCGATCTCTGTGCTACCTGATCTACTCAAC (SEQ ID NO: 78) |
| OT11 | GTGTGAATGGAGGCGAAATTG (SEQ ID NO: 79) | GCAGCTGAGAAGCTAAGGAATA (SEQ ID NO: 80) | ACACTCTTTCCCTACACGACGCTCTTCCGATCTTACATAAAGTCCCTGCAACCTG (SEQ ID NO: 81) | GTGACTGGAGTTCAGACGTGTGCTCTTCCGATCTTTACCAGGACTCTAGTGAGTGG (SEQ ID NO: 82) |
| OT12 | TAGTACCTGCCCACCAGATAG (SEQ ID NO: 83) | GGGCACTTCTTCAATGCTTTAC (SEQ ID NO: 84) | ACACTCTTTCCCTACACGACGCTCTTCCGATCTTCTCCTGACCAGTGTTCTGTAAT (SEQ ID NO: 85) | GTGACTGGAGTTCAGACGTGTGCTCTTCCGATCTAAACCTCGAGTAGGAAGGGA (SEQ ID NO: 86) |
| OT13 | CCCACTGAGGTTGTATCAGTTC (SEQ ID NO: 87) | GATCCAATGGCTTTGCACATAC (SEQ ID NO: 88) | ACACTCTTTCCCTACACGACGCTCTTCCGATCTAAAGAAGACCAGTGAAGGACTG (SEQ ID NO: 89) | GTGACTGGAGTTCAGACGTGTGCTCTTCCGATCTAGTCTGATGACCCGAGTTCTA (SEQ ID NO: 90) |
| OT14 | TCTATATAGGCAGGTTATGAAAGCA (SEQ ID NO: 91) | AACCAGGACATATGTGGTAGAAA (SEQ ID NO: 92) | ACACTCTTTCCCTACACGACGCTCTTCCGATCTTAATGGCCTTCTGGGAAAGT (SEQ ID NO: 93) | GTGACTGGAGTTCAGACGTGTGCTCTTCCGATCTCTGAGTCTGAGAGCTTGTAGTG (SEQ ID NO: 94) |

TABLE 4-continued

List of primers used for targeted deep sequencing at potential off target sites

| No. | 1st PCR Forward (5' to 3') | 1st PCR Reverse (5' to 3') | 2nd PCR Forward (5' to 3') | 2nd PCR Reverse (5' to 3') |
|---|---|---|---|---|
| OT15 | CACAGACAGT CGCCTTCAAT (SEQ ID NO: 95) | TGGAAGCCTTA ACAGGTCAATA A (SEQ ID NO: 96) | ACACTCTTTCC CTACACGACG CTCTTCCGATC TGCCTTCAATG AATCTCCCTTT G (SEQ ID NO: 97) | GTGACTGGAG TTCAGACGTGT GCTCTTCCGAT CTGCTTCATTG GCAGCACTTAC (SEQ ID NO: 98) |
| OT16 | GGAAGATCAG CAGTCTCAAC TAA (SEQ ID NO: 99) | CACATTACCTC AAAGCTGTTTC TT (SEQ ID NO: 100) | ACACTCTTTCC CTACACGACG CTCTTCCGATC TCTCAGTGACA GAGACTCACCT A (SEQ ID NO: 101) | GTGACTGGAG TTCAGACGTGT GCTCTTCCGAT CTGTGGTGACA TGGCTGTATCT T (SEQ ID NO: 102) |
| OT17 | CTTCCACCGG GTATTTCCTA TO (SEQ ID NO: 103) | TCCCAGAGAG AGTTAGGTTAA GA (SEQ ID NO: 104) | ACACTCTTTCC CTACACGACG CTCTTCCGATC TAGATGAATGA GCACCAGAGA AA (SEQ ID NO: 105) | GTGACTGGAG TTCAGACGTGT GCTCTTCCGAT CTAGACAAGAA AGGGCAGTAA GAA (SEQ ID NO: 106) |
| OT18 | CCTGGGAACA ACAGCCATAA (SEQ ID NO: 107) | GAACATTGGGT AGGTGAGGAA G (SEQ ID NO: 108) | ACACTCTTTCC CTACACGACG CTCTTCCGATC TTCTCTGTTGA GGTGGGATTT G (SEQ ID NO: 109) | GTGACTGGAG TTCAGACGTGT GCTCTTCCGAT CTGTACTGCTT GAGGAGCTTG T (SEQ ID NO: 110) |
| OT19 | TGAGCCAGTC CATTCATTCC (SEQ ID NO: 111) | TCCCTCCTGTT CTTCTCTTCT (SEQ ID NO: 112) | ACACTCTTTCC CTACACGACG CTCTTCCGATC TTTGGGACAAG TGTACAGAGAA C (SEQ ID NO: 113) | GTGACTGGAG TTCAGACGTGT GCTCTTCCGAT CTACCTTCACC TACAGAGAAGA GA (SEQ ID NO: 114) |
| OT20 | CCCACAAACC AAGAACAACA A (SEQ ID NO: 115) | CAGTGTTAAGT GCCTCTGTAGA T (SEQ ID NO: 116) | ACACTCTTTCC CTACACGACG CTCTTCCGATC TCAGAAGGGC GGCATCAG (SEQ ID NO: 117) | GTGACTGGAG TTCAGACGTGT GCTCTTCCGAT CTTTAGTCTC TGGTTTCCACC T (SEQ ID NO: 118) |

TABLE 5

List of primers used for targeted deep sequencing at potential off-target sites captured by Digenome-seq

| No. | 1st PCR Forward (5' to 3') | 1st PCR Reverse (5' to 3') | 2nd PCR Forward (5' to 3') | 2nd PCR Reverse (5' to 3') |
|---|---|---|---|---|
| OT1 | ATGGAGCTTG CATTTTAACA (SEQ ID NO: 119) | CTTTTTTCCCG TGATCCTCA (SEQ ID NO: 120) | ACACTCTTTCC CTACACGACG CTCTTCCGATC TATGGAGCTT GCATTTTAACA (SEQ ID NO: 121) | GTGACTGGAG TTCAGACGTGT GCTCTTCCGAT CTGCTGGCTT ATTTCATCATT TAG (SEQ ID NO: 122) |

TABLE 5-continued

List of primers used for targeted deep sequencing at potential off-target sites captured by Digenome-seq

| No. | 1st PCR Forward (5' to 3') | 1st PCR Reverse (5' to 3') | 2nd PCR Forward (5' to 3') | 2nd PCR Reverse (5' to 3') |
| --- | --- | --- | --- | --- |
| OT2 | CAAACTGTCAGTGAGCCAATAC (SEQ ID NO: 123) | GAAGTGATCCTCCTCTCAATACC (SEQ ID NO: 124) | ACACTCTTTCCCTACACGACGCTCTTCCGATCTCAGGAAGTCAAGCAGGAAGA (SEQ ID NO: 125) | GTGACTGGAGTTCAGACGTGTGCTCTTCCGATCTCATCCATCCATTCATAACTTTGGA (SEQ ID NO: 126) |
| OT3 | GTCCAATACTCTAAGCCTCAGTT (SEQ ID NO: 127) | ACCAGCACCACACTATCTATTT (SEQ ID NO: 128) | ACACTCTTTCCCTACACGACGCTCTTCCGATCTATACCTAGTTTGTAGGGTTGTT (SEQ ID NO: 129) | GTGACTGGAGTTCAGACGTGTGCTCTTCCGATCTGCACCACACTATCTATTTCTGTTAT (SEQ ID NO: 130) |
| OT4 | ACACTATGATCTTTCCCTGCAA (SEQ ID NO: 131) | CAGAAACCCTGAAGTCTTGAATTG (SEQ ID NO: 132) | ACACTCTTTCCCTACACGACGCTCTTCCGATCTTCTTTCCCTGCAAAGAAGTAAGA (SEQ ID NO: 133) | GTGACTGGAGTTCAGACGTGTGCTCTTCCGATCTGTCTCATTGTCCAGAACTGTGT (SEQ ID NO: 134) |
| OT5 | GGGCAGAAAGGACAGAAACT (SEQ ID NO: 135) | GGAGAAACTGAAACCAGGAGAA (SEQ ID NO: 136) | ACACTCTTTCCCTACACGACGCTCTTCCGATCTCGTAACAGCACCTTGGTCAT (SEQ ID NO: 137) | GTGACTGGAGTTCAGACGTGTGCTCTTCCGATCTCTGAAACCAGGAGAAGTGTAGTC (SEQ ID NO: 138) |
| OT6 | AGTAGGTGGGAGGGTTCTTAT (SEQ ID NO: 139) | CACCATCTCTGTGTCTCATCTG (SEQ ID NO: 140) | ACACTCTTTCCCTACACGACGCTCTTCCGATCTAGAAACAGGCATCTGGAGAAC (SEQ ID NO: 141) | GTGACTGGAGTTCAGACGTGTGCTCTTCCGATCTTTTCAGCATAGTCTTGCTCGTC (SEQ ID NO: 142) |
| OT7 | TAAGCCTGGCCTGTCTCTT (SEQ ID NO: 143) | AGAGCAGGACGTGGTGAG (SEQ ID NO: 144) | ACACTCTTTCCCTACACGACGCTCTTCCGATCTTCTCTTCCTGGGACCCT (SEQ ID NO: 145) | GTGACTGGAGTTCAGACGTGTGCTCTTCCGATCTATACCTAGGAATGCAGAACAAG (SEQ ID NO: 146) |
| OT8 | GGGATTGCACTTAGGTTCTTCT (SEQ ID NO: 147) | CTATGCGGTCTCTTGTGCTAAT (SEQ ID NO: 148) | ACACTCTTTCCCTACACGACGCTCTTCCGATCTGGTCAGGTGGGTAATGATTTCTG (SEQ ID NO: 149) | GTGACTGGAGTTCAGACGTGTGCTCTTCCGATCTCTAATCTGCCTTATGTAATGGGTTCT (SEQ ID NO: 150) |
| OT9 | GACTCCTCTGTGGAAAGAGC (SEQ ID NO: 151) | AGGACTCCAGTGCTGAGCAC (SEQ ID NO: 152) | ACACTCTTTCCCTACACGACGCTCTTCCGATCTTCCTCTGTGGAAAGAGCCT (SEQ ID NO: 153) | GTGACTGGAGTTCAGACGTGTGCTCTTCCGATCTACACCGTCTCTCCTTTGTGC (SEQ ID NO: 154) |
| OT10 | AGGGACCGTATCAGATATTGTTAATC (SEQ ID NO: 155) | TCCAATGTATTGCAGCCATCT (SEQ ID NO: 156) | ACACTCTTTCCCTACACGACGCTCTTCCGATCTTAATCAATCCTTGTGCAGCTTAATG (SEQ ID NO: 157) | GTGACTGGAGTTCAGACGTGTGCTCTTCCGATCTCAGCCATCTTGCCCTTTGA (SEQ ID NO: 158) |

TABLE 5-continued

List of primers used for targeted deep sequencing at potential off-target sites captured by Digenome-seq

| No. | 1st PCR Forward (5' to 3') | 1st PCR Reverse (5' to 3') | 2nd PCR Forward (5' to 3') | 2nd PCR Reverse (5' to 3') |
| --- | --- | --- | --- | --- |
| OT11 | CATTGAGGAA CCTCACCTTCT AT (SEQ ID NO: 159) | ATGAATGTCTT GGTACTGTCC GTATTAGGCC TC (SEQ ID NO: 160) | ACACTCTTTCC CTACACGACG CTCTTCCGATC TGGAAGAGGT ATT (SEQ ID NO: 161) | GTGACTGGAG TTCAGACGTGT GCTCTTCCGAT CTCCTCTTCTC TCTTGCTTCAT CTC (SEQ ID NO: 162) |
| OT12 | CAAAGCAGCT CCTCTTCCTC (SEQ ID NO: 163) | CAGTGCCTTTC AGTGAACCT (SEQ ID NO: 164) | ACACTCTTTCC CTACACGACG CTCTTCCGATC TTCTGGGTATA GAGACCATGA CA (SEQ ID NO: 165) | GTGACTGGAG TTCAGACGTGT GCTCTTCCGAT CTCACAGCCT GAGATAATGAT AGAGAG (SEQ ID NO: 166) |
| OT13 | GGAGTCGTAC CCTGGTTTATT T (SEQ ID NO: 167) | GAAGCATTGTT CCACCTTAACC (SEQ ID NO: 168) | ACACTCTTTCC CTACACGACG CTCTTCCGATC TGGGATAGAA GATTAGGCAG AGTATG (SEQ ID NO: 169) | GTGACTGGAG TTCAGACGTGT GCTCTTCCGAT CTTGCATGTTT GAAAGGATGA GC (SEQ ID NO: 170) |
| OT14 | CTACTCACCTA T (SEQ ID NO: 171) | ACCTGTGGAA G (SEQ ID NO: 172) | ACACTCTTTCC CTACACGACG CTCTCAGACC CTCTTCCGATC TAGACCCTACT CACCTATATCC TTT (SEQ ID NO: 173) | GTGACTGGAG TTCAGACGTGT CACTGGAAGT GCTCTTCCGAT CTTACCTGTG GAAGCAGGAG A (SEQ ID NO: 174) |
| OT15 | GGCCATCCTC AAAGACATGAA (SEQ ID NO: 175) | TCTCAAACTCC CGACCTCA (SEQ ID NO: 176) | ACACTCTTTCC CTACACGACG CTCTTCCGATC TGCATTTCTAT TTATTCATCTC CCACAG (SEQ ID NO: 177) | GTGACTGGAG TTCAGACGTGT GCTCTTCCGAT CTCTGGGATTA CAGGCGTGAG (SEQ ID NO: 178) |
| OT16 | AGAAGTTTCAG GATGACAGAT CC (SEQ ID NO: 179) | CAATCCACATC TGCGTGTTTC (SEQ ID NO: 180) | ACACTCTTTCC CTACACGACG CTCTTCCGATC TAGAAGTTTCA GGATGACAGA TCC (SEQ ID NO: 181) | GTGACTGGAG TTCAGACGTGT GCTCTTCCGAT CTCAATCCACA TCTGCGTGTTT C (SEQ ID NO: 182) |
| OT17 | TGACTCATTGT GAATGCCTTTA TTC (SEQ ID NO: 183) | GAGTTGGGTT CTCTGCAACT (SEQ ID NO: 184) | ACACTCTTTCC CTACACGACG CTCTTCCGATC TTATAGAGTCT AGATTAGCAGT AGAGC (SEQ ID NO: 185) | GTGACTGGAG TTCAGACGTGT GCTCTTCCGAT CTAAGTCTTAT CTGATACATG GATACC (SEQ ID NO: 186) |
| OT18 | TGCAGCTCTG GACAGGAA (SEQ ID NO: 187) | GGTGGGTTTC ACCATCCTC (SEQ ID NO: 188) | ACACTCTTTCC CTACACGACG CTCTTCCGATC TGGGTGATTC CCTCTGTGG (SEQ ID NO: 189) | GTGACTGGAG TTCAGACGTGT GCTCTTCCGAT CTCCATCCTCC TGCCCTCT (SEQ ID NO: 190) |

TABLE 5-continued

List of primers used for targeted deep sequencing at potential off-target sites captured by Digenome-seq

| No. | 1st PCR Forward (5' to 3') | 1st PCR Reverse (5' to 3') | 2nd PCR Forward (5' to 3') | 2nd PCR Reverse (5' to 3') |
|---|---|---|---|---|
| OT19 | GACAGCACTTAGGGATGATGAA (SEQ ID NO: 191) | GATGGAGCTGCCCAAGAAA (SEQ ID NO: 192) | ACACTCTTTCCCTACACGACGCTCTTCCGATCTGGGATGATGAATGGCTGGAT (SEQ ID NO: 193) | GTGACTGGAGTTCAGACGTGTGCTCTTCCGATCTCTTCTCCATGTAGGTGCCTT (SEQ ID NO: 194) |
| OT20 | CCTGAGAACAAGGAGTGTCAAG (SEQ ID NO: 195) | CCATGGAATGCCCAGATAGTT (SEQ ID NO: 196) | ACACTCTTTCCCTACACGACGCTCTTCCGATCTGTTGATATCCCAGCTTAAGCAATC (SEQ ID NO: 197) | GTGACTGGAGTTCAGACGTGTGCTCTTCCGATCTTTTAAACATCATTTCTGGCACGTC (SEQ ID NO: 198) |
| OT21 | AGCTATTGCTGTCAATCTCTTACT (SEQ ID NO: 199) | TACCCAGTCTCAGGTAGTTCTT (SEQ ID NO: 200) | ACACTCTTTCCCTACACGACGCTCTTCCGATCTTGCTGTCAATCTCTTACTGTAACTA (SEQ ID NO: 201) | GTGACTGGAGTTCAGACGTGTGCTCTTCCGATCTTAGCAATGCGAGAACAGACTAA (SEQ ID NO: 202) |
| OT22 | TGCCACACATCCCATCATATC (SEQ ID NO: 203) | CAGCAGACACAGACTCACAA (SEQ ID NO: 204) | ACACTCTTTCCCTACACGACGCTCTTCCGATCTCAACATGAAATGCCAGAGTCAAA (SEQ ID NO: 205) | GTGACTGGAGTTCAGACGTGTGCTCTTCCGATCTCCCATTCAAGTTGCAATCACTATC (SEQ ID NO: 206) |
| OT23 | TCCTGAAAGAAGGGATAAGGTAAG (SEQ ID NO: 207) | TGAGGATGGGTTTCGGTAAAT (SEQ ID NO: 208) | ACACTCTTTCCCTACACGACGCTCTTCCGATCTATAAGGTAAGCTCAGCCTGTC (SEQ ID NO: 209) | GTGACTGGAGTTCAGACGTGTGCTCTTCCGATCTGTTTCAACATGAAGGCAGGAG (SEQ ID NO: 210) |
| OT24 | CAAGAAGGGTGTTAGGTTATGAAAG (SEQ ID NO: 211) | ACAGTCAACCCTTAAGGAAGAG (SEQ ID NO: 212) | ACACTCTTTCCCTACACGACGCTCTTCCGATCTGGGTGTTAGGTTATGAAAGTTAAGG (SEQ ID NO: 213) | GTGACTGGAGTTCAGACGTGTGCTCTTCCGATCTAAGGAAGAGTTGTCTTCACTCG (SEQ ID NO: 214) |
| OT25 | CTTTCACAGCCAGTCACAAATAAA (SEQ ID NO: 215) | CTCACACTCTAGGAAACAGATGATAG (SEQ ID NO: 216) | ACACTCTTTCCCTACACGACGCTCTTCCGATCTCAATCCACTCAGACTACAGAGAAA (SEQ ID NO: 217) | GTGACTGGAGTTCAGACGTGTGCTCTTCCGATCTAGACAGGAGTGTTCTCCAAATC (SEQ ID NO: 218) |
| OT26 | GTGAGCCAAGATCACACCAT (SEQ ID NO: 219) | CTCTCAGCAAGAAGGCAGATT (SEQ ID NO: 220) | ACACTCTTTCCCTACACGACGCTCTTCCGATCTAGATCACACCATTGCACTCC (SEQ ID NO: 221) | GTGACTGGAGTTCAGACGTGTGCTCTTCCGATCTGCCAGATCAGTGTCTGCTAAA (SEQ ID NO: 222) |
| OT27 | GGACACGCTGAGTCAAAGTT (SEQ ID NO: 223) | CCTTTCCTTCGTGCTGATTGA (SEQ ID NO: 224) | ACACTCTTTCCCTACACGACGCTCTTCCGATCTGCAACCACGTCGACAATACA (SEQ ID NO: 225) | GTGACTGGAGTTCAGACGTGTGCTCTTCCGATCTGGTGGAAGTGACAAGCAAGTTA (SEQ ID NO: 226) |

TABLE 5-continued

List of primers used for targeted deep sequencing at potential off-target sites captured by Digenome-seq

| No. | 1st PCR Forward (5' to 3') | 1st PCR Reverse (5' to 3') | 2nd PCR Forward (5' to 3') | 2nd PCR Reverse (5' to 3') |
|---|---|---|---|---|
| OT28 | CCCAACAATTC CTTCTTTGAGC (SEQ ID NO: 227) | TCTGCTATTAG AGGAGGCTAG AA (SEQ ID NO: 228) | ACACTCTTTCC CTACACGACG CTCTTCCGATC TCAATTCCTTC TTTGAGCTCAC TAT (SEQ ID NO: 229) | GTGACTGGAG TTCAGACGTGT GCTCTTCCGAT CTGAGGCTAG AACAACCTTG GA (SEQ ID NO: 230) |
| OT29 | GGGCAAATCC ATAACCCAGAA TA (SEQ ID NO: 231) | AGGCGATGCA TGAGCTTAAA (SEQ ID NO: 232) | ACACTCTTTCC CTACACGACG CTCTTCCGATC TGGGCAAATC CATAACCCAG A (SEQ ID NO: 233) | GTGACTGGAG TTCAGACGTGT GCTCTTCCGAT CTGTAGCTAAT CTGGCTACCA TCAC (SEQ ID NO: 234) |
| OT30 | ATTGGCTGGC ACACAGTAG (SEQ ID NO: 235) | CCCAGGATCT AGCAAACATTC A (SEQ ID NO: 236) | ACACTCTTTCC CTACACGACG CTCTTCCGATC TTGAATGAATG AAGGAAAGAA TGGG (SEQ ID NO: 237) | GTGACTGGAG TTCAGACGTGT GCTCTTCCGAT CTGCAAACATT CATCTTTCGAG CTA (SEQ ID NO: 238) |
| OT31 | CACTTCTCGC CTTTGACCTT (SEQ ID NO: 239) | TGGCTGTGCT CACTTTACTG (SEQ ID NO: 240) | ACACTCTTTCC CTACACGACG CTCTTCCGATC TAGAGGAGGA AACTGGAGCT TA (SEQ ID NO: 241) | GTGACTGGAG TTCAGACGTGT GCTCTTCCGAT CTACTTTACTG CCACCAGTGC (SEQ ID NO: 242) |
| OT32 | ATCTTCCACAG GTGCAAATCT (SEQ ID NO: 243) | TTGCCTATGG CTGCCTTG (SEQ ID NO: 244) | ACACTCTTTCC CTACACGACG CTCTTCCGATC TCTGGTCATTC TCTTCCGTCAA A (SEQ ID NO: 245) | GTGACTGGAG TTCAGACGTGT GCTCTTCCGAT CTAACAGTATG GGCCTGAAAA G (SEQ ID NO: 246) |
| OT33 | CATGTAACCAC GACTACCTCAA (SEQ ID NO: 247) | CCATGGCTTG CAGCAATTT (SEQ ID NO: 248) | ACACTCTTTCC CTACACGACG CTCTTCCGATC TGTAACCACG ACTACCTCAAG ATATAA (SEQ ID NO: 249) | GTGACTGGAG TTCAGACGTGT GCTCTTCCGAT CTCACACAGA CGTACTGTTAA GGA (SEQ ID NO: 250) |
| OT34 | CTTAGAGGAA AGAGAACTGG GATTAT (SEQ ID NO: 251) | AGTGTGGCTG ATTATGGTGAT TA (SEQ ID NO: 252) | ACACTCTTTCC CTACACGACG CTCTTCCGATC TCCAAGAGTA GCCTAACCTTT ACAA (SEQ ID NO: 253) | GTGACTGGAG TTCAGACGTGT GCTCTTCCGAT CTCACGTAAAT TGCACCTGTC AC (SEQ ID NO: 254) |
| OT35 | TTTCTCTGCCA TTCTTCCTCTG (SEQ ID NO: 255) | GAATGAAGAC ACGAGGCATT TG (SEQ ID NO: 256) | ACACTCTTTCC CTACACGACG CTCTTCCGATC TTCTTAGCCCA TGTTGCTTCC (SEQ ID NO: 257) | GTGACTGGAG TTCAGACGTGT GCTCTTCCGAT CTTCCAGAATG TACCTTGCACT TT (SEQ ID NO: 258) |
| OT36 | TGCTGTCTTTA GTTCCTTCATT (SEQ ID NO: 259) | TTAACCCAGCA TCAGCTCTC (SEQ ID NO: 260) | ACACTCTTTCC CTACACGACG CTCTTCCGATC TTGCTGTCTTT AGTTCCTTCAT T (SEQ ID NO: 261) | GTGACTGGAG TTCAGACGTGT GCTCTTCCGAT CTTTAACCCAG CATCAGCTCTC (SEQ ID NO: 262) |

TABLE 5-continued

List of primers used for targeted deep sequencing at potential off-target sites captured by Digenome-seq

| | 1st PCR | | 2nd PCR | |
|---|---|---|---|---|
| No. | Forward (5' to 3') | Reverse (5' to 3') | Forward (5' to 3') | Reverse (5' to 3') |
| OT37 | TTTCCAGAAGAGCCGACAAG (SEQ ID NO: 263) | CCAACAACCACCACGACTAA (SEQ ID NO: 264) | ACACTCTTTCCCTACACGACGCTCTTCCGATCTGGGCCCTTCTGCTTTGAG (SEQ ID NO: 265) | GTGACTGGAGTTCAGACGTGTGCTCTTCCGATCTAGTCTCCCATGAAGGCTGTA (SEQ ID NO: 266) |
| OT38 | AAAGTACATAGAGGACGTGCATAG (SEQ ID NO: 267) | AGTTCACCACCACCACAAG (SEQ ID NO: 268) | ACACTCTTTCCCTACACGACGCTCTTCCGATCTTGTGCAAATACTACGCCATTTC (SEQ ID NO: 269) | GTGACTGGAGTTCAGACGTGTGCTCTTCCGATCTACAAGTTTGCACTTGCTTTCA (SEQ ID NO: 270) |
| OT39 | CACCTGGACCACCAGAAA (SEQ ID NO: 271) | GCTGTTTGCAAATGCCTCA (SEQ ID NO: 272) | ACACTCTTTCCCTACACGACGCTCTTCCGATCTCACCTGGACCACCAGAAA (SEQ ID NO: 273) | GTGACTGGAGTTCAGACGTGTGCTCTTCCGATCTACCCATCTCTGCAGACCTTA (SEQ ID NO: 274) |
| OT40 | CTGATTTCCTGAGTTTCTCCCTAA (SEQ ID NO: 275) | AAGTGTGGGCTGTGCATAA (SEQ ID NO: 276) | ACACTCTTTCCCTACACGACGCTCTTCCGATCTCTGTGAAGGGATTTCAAACTTTCC (SEQ ID NO: 277) | GTGACTGGAGTTCAGACGTGTGCTCTTCCGATCTCGATCAAGGCTAACGTCATCA (SEQ ID NO: 278) |
| OT41 | CATCTCCTGCTGTGTCATCTT (SEQ ID NO: 279) | CCAGTCTCGGGTATGTCTTTATT (SEQ ID NO: 280) | ACACTCTTTCCCTACACGACGCTCTTCCGATCTGACTGACTTCCATCTTCCTCAC (SEQ ID NO: 281) | GTGACTGGAGTTCAGACGTGTGCTCTTCCGATCTCAGACTAATACATCCGGTCTCATC (SEQ ID NO: 282) |

Indels around a site 3 bp upstream of the PAM sequence were considered to be mutations resulting from Cas9 RNP activity.

7. RNA extraction and qPCR

Total RNA was isolated from NIH3T3 and ARPE-19 cells using an Easy-Spin™ Total RNA extraction Kit (iNtRON, Korea) according to the manufacturer's protocol. Then, 250 ng of RNA was reverse transcribed using SuperScript II (Enzynomics). Quantitative PCR (qPCR) was performed using SYBR Green (KAPA) with the following primers:

Mouse Vegfa:
(forward; SEQ ID NO: 283)
5'-ACGTCAGAGAGCAACATCAC-3', (reverse; SEQ ID NO: 284)
5'-CTGTCTTTCTTTGGTCTGCATTC-3';

Mouse Gapdh:
(forward; SEQ ID NO: 285)
5'-GCTGAGTATGTCGTGGAGTCTA-3', (reverse; SEQ ID NO: 286)
5'-GTGGTTCACACCCATCACAA-3';

Human VEGFA-1:
(forward; SEQ ID NO: 287)
5'-CGAGTACATCTTCAAGCCATCC-3', (reverse; SEQ ID NO: 288)
5'-GGTGAGGTTTGATCCGCATAAT-3';

Human VEGFA-2:
(forward; SEQ ID NO: 289)
5'-AGAAGGAGGAGGGCAGAAT-3', (reverse; SEQ ID NO: 290)
5'-CACAGGATGGCTTGAAGATGTA-3';

Human GAPDH:
(forward; SEQ ID NO: 291)
5'-CAATGACCCCTTCATTGACC-3', (reverse; SEQ ID NO: 292)
5'-TTGATTTTGGAGGGATCTCG-3'.

8. VEGFA ELISA Using Confluent ARPE-19 Cells

For human VEGFA ELISA, Vegfa-specific Cas9 RNP-treated confluent ARPE-19 cells were incubated in a serum-free medium for 16 hours after which serum-free supernatants were collected from the cell culture. Secreted VEGFA protein levels were measured using a human VEGF Quantikine ELISA Kit (DVE00, R & D systems) according to the manufacturer's instructions.

9. In Vitro Cleavage of Genomic DNA and Digenome Sequencing

Genomic DNA was isolated from ARPE-19 cells (ATCC) using a DNeasy Tissue Kit (Qiagen). In vitro cleavage of genomic DNA for Digenome sequencing was performed as described below. In brief, genomic DNA (20 µg) was incubated with Cas9 protein (16.7 µg) and sgRNA (12.5 µg) in reaction buffer (100 mM NaCl, 50 mM Tris-HCl, 10 mM $MgCl_2$, 100 µg/mL BAS, pH 7.9) for 3 hours at 37° C. to induce the cleavage of genomic DNA by Cas9. Cleaved genomic DNA was treated with RNase A (50 µg/mL, Sigma Aldrich) for 30 min at 37° C. and purified with a DNeasy Tissue Kit (Qiagen). Whole-genome and Digenome sequencing were performed as described previously (Kim, D., Kim, S., Kim, S., Park, J. & Kim, J. S. Genome-wide target specificities of CRISPR-Cas9 nucleases revealed by multiplex Digenome-seq. *Genome research* 26, 406-415 (2016)).

10. Preparation of Animals Administered with RNP by Subretinal Injection

The care, use, and treatment of all animals in this study were in strict agreement with the guidelines established by the Seoul National University Institutional Animal Care and Use Committee and "the ARVO Statement for the Use of Animals in Ophthalmic and Vision Research". Adult (6 weeks old) male SPF C57BU6J mice were used in the study. Mice were maintained under a 12 hours dark-light cycle.

Subretinal injection of RNP was performed on the prepared mice as follows. First, RNPs composed of Cas9 protein (8 µg), sgRNA (4.5 µg), and Lipofectamine 2000 (20% v/v) were mixed in 2 µL or 3 µL of injection volume. RNPs (2 or 3 µL) were injected into the subretinal space using a Nanofil syringe with a 33G blunt needle (World Precision Instruments, Inc.) under an operating microscope (Leica Microsystems, Ltd.). Subjects with retinal hemorrhage were excluded from the study.

11. Construction of Laser-Induced Choroidal Neovascularization (CNV) Animal Models Mice were anesthetized by intraperitoneally injecting at a dose of 2.25 mg/kg (body weight) a mixture containing tiletamine and zolazepam at a weight ratio of 1:1. Pupils were dilated with an eye drop containing phenylephrine (0.5% (w/v)) and tropicamide (0.5% (w/v)). Laser photocoagulation was performed using an indirect head set delivery system (Iridex) and laser system (Ilooda). The laser wavelength was 810 nm. Laser parameters were as follows: spot size: 200 µm; power: 1W; and exposure time: 100 ms. Laser burn was induced at the 12 (right eye) or 6 (left eye) o'clock positions around the optic disc with a modification. Only burns that produced a bubble without vitreous hemorrhage were included in the experiments. Subretinal RNP injections were performed in the quadrant of laser burn. Cas9 RNPs (sgRosa26 (containing a Rosa26 targeting sgRNA) or sg Vegfa (containing a Vegfa targeting sgRNA)) were randomly allocated to the left or right eye in each mouse. Subretinal injection of Cas9 RNPs produced a bleb. It was confirmed that the bleb overlapped with the laser-burn site. Subjects in which the bleb overlapped the laser-burn site were used in further studies. Seven days after laser treatment, the eyes were fixed in 4% PFA for 1 hour at room temperature. RPE (retinal pigment epithelium) complexes (RPE/choroid/sclera) were treated overnight at 4° C. with isolectin-B4 (Thermo Fisher Scientific, catalog no. 121413, 1:100) for immunostaining. The stained RPE complexes were flat-mounted and viewed with a fluorescence microscope (Eclipse 90i, Nikon) at a magnification of x40. The CNV area was measured using ImageJ software (1.47v, NIH) by blind observers.

12. Immunosfluorescent Staining and Imaging

The number of RPE cells in the RPE complex was calculated by counting DAPI-stained nuclei in paraffin embedded cross-section samples (4 µm) in a high power field area (100 µm×100 µm, n=8). Cross-section samples obtained at day 7 post-injection (n=4) were immunostained with an anti-opsin antibody (Millipore, AB5405, 1:1000) and an Alexa Fluor 488 antibody (Thermo Fisher Scientific, 1:500). The opsin positive area was measured using ImageJ software (1.47v, NIH) by blind observers. The intracellular distribution of the Cy3-Cas9 protein in the RPE flat-mounts was imaged using a confocal microscope (LSM 710, Carl Zeiss). The scanning parameters were as follows: scaling (x=0.042 µm/pixel, y=0.042 µm/pixel, z=0.603 µm/pixel), dimensions (x=1024, y=1024, z=12, channels: 2, 8-bit), and zoom (5.0) with objective C-Apochromat 40x/1.20W Korr M27. ZEN 2 software was used to process the images.

13. Genomic DNA Extraction from CNV Area and RPE Complex

Genomic DNA was isolated from RPE complexed at day 3 after RNP injection, and measured for CNV area. At day 7 after RNP injection, genomic DNA was isolated from CNV samples. Genomic DNA isolation was performed using a NucleoSpin Tissue Kit (Macherey-Nagel). In order to evaluate RNP efficacy, each RPE complex was divided into quadrants and the RNP-injected quadrant was treated to isolate genomic DNA. To assess indel frequencies in CNV areas of RPE complexes, RPE flat-mounts were imaged and washed with PBS. Genomic DNA was isolated from the following regions: (i) a quadrant including an RNP-injected area of CNV (representative of injected areas); and (ii) an opposite quadrant (representative of non-injected areas).

14. Mouse VEGF-A ELISA

For mouse VEGF-A ELISA, a total of 30 laser burns were induced in the eye, followed by injecting RNPs (3 µL) into the subretinal space. At day 3 post-injection, whole RPE complexes were isolated from the retina and frozen for further analysis. Cells were lysed with RIPA buffer (50 mM Tris-HCl(pH 8.0), 150 mM NaCl, 1% Igepal CA-630, 0.5% Na.deoxycholate, 0.1% SDS), and VEGFA levels were measured using a mouse VEGF Quantikine ELISA Kit (MMV00, R&D systems) according to the manufacturer's instructions.

15. Western Blotting

To analyze RNP levels over time after in vivo RNP delivery, Western blotting of RPE complexes, obtained at 1 and 3 days post-injection, was performed. Samples, each containing an equal amount of protein (20 µg), were analyzed; Cas9 and beta-actin were detected with an anti-HA high affinity antibody (Roche, 3F10, 1:1000) and an anti-beta-actin antibody (Sigma Aldrich, A2066, 1:1000), respectively. ImageQuant LAS4000 (GE healthcare) was used for digital imaging.

16. Statistics

Data were analyzed with SPSS software version 18.0 (SPSS, Inc.). P-values were determined by an unpaired, two-sided Student's t-tests or one-way ANOVA and Tukey post-hoc tests (for multiple groups). Data are expressed as mean with s.e.m (standard error of the mean).

Example 1: Target Mutation of VegfaNEGFA Gene Through Cas9 Ribonucleoproteins (RNPs)

A test was made of four single-chain guide RNAs (sgRNAs) (labeled as Vegfa-1, 2, 3, and 4) targeting target sites in exons 3 and 4 which encode binding sites for VEGF receptors 1 and 2, respectively, in the mouse NIH3T3 cell line and the human RPE cell line (ARPE-19). The four sgRNAs (Vegfa-1, 2, 3, and 4) were constructed with reference to Reference Example 1.

The targeting sequences of sgRNA for CRISPR-Cas9 target sequences in the VEGFA/Vefga gene and numbers of homologous sites in the human and mouse genomes are summarized in Table 6, below:

Representative mutant DNA sequences induced by Vegfa-specific Cas9 RNP (containing Vegfa-1 sgRNA) at the Vegfa/VEGFA locus in NIH3T3 and ARPE-19 cells are shown in FIG. 1d (underlined: target sequence targeted by sgRNA, blue: inserted nucleotides, —: deleted region, WT: wild type; triangle: cleavage position; column on the right: number of inserted or deleted nucleotides).

Mutation (indel) frequencies induced by the delivery of Vegfa-specific Cas9 RNP containing Vegfa-1 sgRNA in

TABLE 6

| Target | sgRNA with PAM (5' to 3') | Position | Direction | Number of mismatches at homologous sites* | | |
|---|---|---|---|---|---|---|
| | | | | 0 | 1 | 2 |
| Vegfa-1 human | CTCCTGGAAGATGTCCACCAG GG | Exon 3 | - | 1 | 0 | 1 |
| mouse | (SEQ ID NO: 293) | | | 1 | 0 | 1 |
| Vegfa-2 human | AGCTCATCTCTCCTATGTGCT GG | Exon 4 | - | 1 | 0 | 1 |
| mouse | (SEQ ID NO: 294) | | | 1 | 0 | 3 |
| Vegfa-3 human | GACCCTGGTGGACATCTTCCA GG | Exon 3 | + | 1 | 0 | 0 |
| mouse | (SEQ ID NO: 295) | | | 1 | 0 | 1 |
| Vegfa-4 human | ACTCCTGGAAGATGTCCACCA GG | Exon 3 | - | 1 | 0 | 1 |
| mouse | (SEQ ID NO: 296) | | | 1 | 0 | 0 |

(*Determined using Cas-OFFinder; underlined: PAM sequence)

The sgRNA-containing Vegfa-specific Cas9 RNP prepared above were transfected into mouse NIH3T3 and human ARPE-19 cells and used in the following experiments. The delivery of RNP into cells, as described in Reference Example 3, was carried out with the aid of a plasmid that was introduced into cells and allowed nucleic acid molecules to express sgRNA and Cas9 protein in the cells (expressed as plasmid in figures) or in such a manner that a complex (or mixture) of the sgRNA and the recombinant Cas9 protein was delivered into cells using cationic lipid (Lipofectamine) (expressed as RNP in figures).

The target sequence in the Vegfa/VEGFA locus of mouse NIH3T3 and human ARPE-19 cells are depicted in FIG. 1a (PAM sequence in red; sgRNA target sequence in blue).

Mutation frequencies induced by the delivery of either Vegfa-specific Cas9 RNPs containing the four sgRNAs (Vegfa-1 sgRNA, Vegfa-2 sgRNA, Vegfa-3 sgRNA, and Vegfa-4 sgRNA) or plasmids carrying encoding sequences thereof were measured using deep sequencing (see Reference Example 2) at day 2 post-transfection. The results are shown in FIG. 1h (Error bars indicate s.e.m. (n=3), One-way ANOVA and Tukey post-hoc tests, *** P<0.001).

Figure 1B:
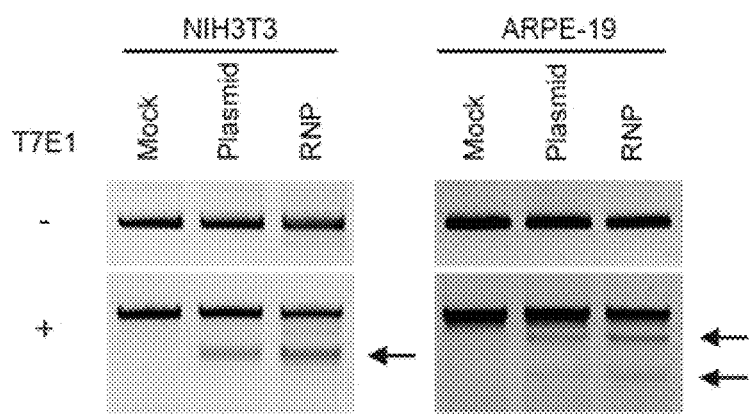
FIG. 1b shows mutations induced by the delivery of either Vegfa-specific Cas9 RNP containing Vegfa-1 sgRNA or a plasmid carrying an encoding sequence thereof in NIH3T3, as detected by the T7 endonuclease I (T7E1) assay.

In addition, mutations induced by the delivery of either Vegfa-specific Cas9 RNP containing Vegfa-1 sgRNA or a plasmid carrying an encoding sequence thereof in NIH3T3 and ARPE-19 cells were detected by the T7 endonuclease I (T7E1) assay and are shown in FIG. 1b. In FIG. 1b, arrows indicate the expected positions of DNA bands cleaved by T7E1.

Figure 1E:
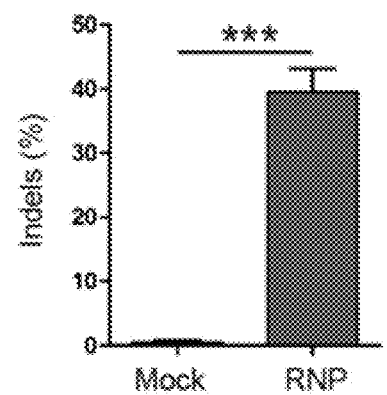
FIG. 1e is a graph showing indel frequencies induced by the delivery of the Vegfa-specific Cas9 RNP containing the Vegfa-1 sgRNA in confluent ARPE-19 cells.
Figure 1F:
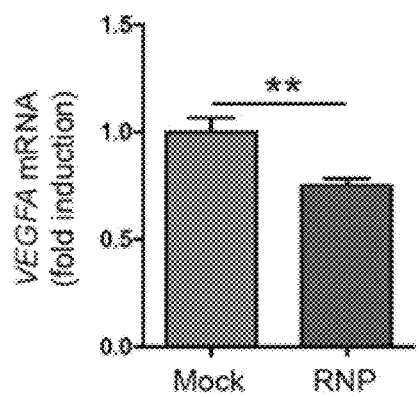
FIG. 1f is a graph showing VEGFA mRNA levels in confluent ARPE-19 cells transfected with the Vegfa-specific Cas9 RNP containing the Vegfa-1 sgRNA.
Figure 1G:
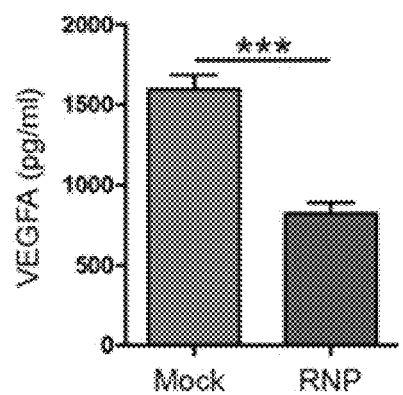
FIG. 1g is a graph showing VEGFA protein levels in confluent ARPE-19 cells transfected with the Vegfa-specific Cas9 RNP containing the Vegfa-1 sgRNA.
Figure 1H:
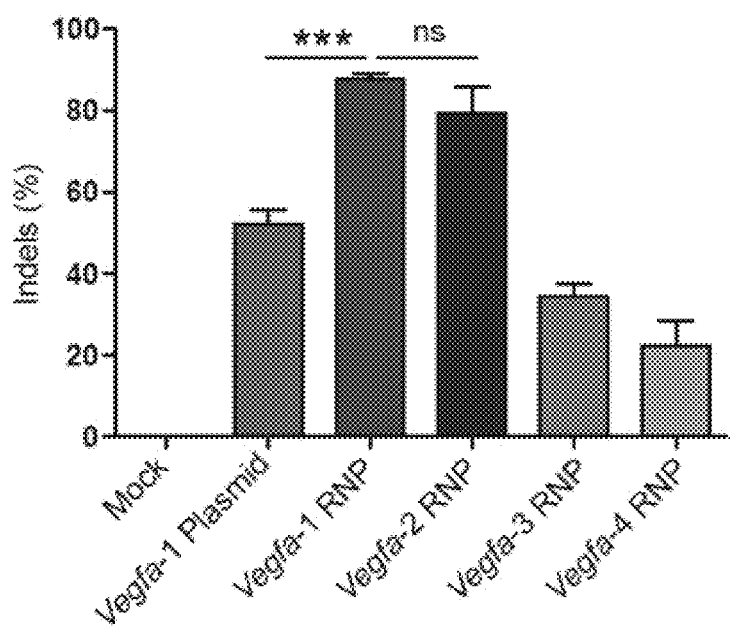
FIG. 1h is a graph showing indel frequencies induced by the delivery of either Vegfa-specific Cas9 RNPs containing four sgRNAs (Vegfa-1 sgRNA, Vegfa-2 sgRNA, Vegfa-3 sgRNA, and Vegfa-4 sgRNA) or plasmids carrying encoding sequences thereof.

Indel frequencies induced by the delivery of either Vegfa-specific Cas9 RNP containing Vegfa-1 sgRNA or a plasmid carrying an encoding sequence thereof in NIH3T3 and ARPE-19 cells were measured using targeted deep sequencing (see Reference Example 6) at day 2 post-transfection. The results are shown in FIG. 1c (error bar: s.e.m (n=3); One-way ANOVA and Tukey post-hoc tests, * P<0.05,  P<0.01, * P<0.001).

confluent ARPE-19 cells were detected by targeted deep sequencing at 64 hours post-transfection, and the results are given in FIG. 1e. Relative VEGFA mRNA levels measured in the cells by quantitative PCR (qPCR) are depicted in FIG. 1f, and VEGFA protein levels measured in the cells by VEGFA ELISA as in Reference Example 8 are shown in FIG. 1g (Error bar: s.e.m. (n=5), Student's t-test,  P<0.01, * P<0.001).

As shown in FIG. 1h, the highest indel efficiency was obtained in NIH3T3 cells when Vegfa-1 sgRNA among the four sgRNAs was complexed with Cas9 and delivered in the RNP form into the cells. In addition, FIGS. 1b and 1c show that Vegfa-1 sgRNA with the highest indel efficiency induced mutations in NIH3T3 and ARPE-19 cells and when delivered in an RNP form, was observed to induce small insertions and deletions (indels) at the target site with a frequency of 82±5% (NIH3T3 cells) or 57±3% (ARPE-19 cells). The RNP delivery of sgRNA and Cas9 allowed higher indel efficiency than plasmid transfection (FIG. 1c).

As shown in FIG. 1e, indels were detected at a frequency of 40±8% in ARPE-19 cells treated with Vegfa-specific Cas9 RNP, and FIGS. 1f and 1g show that Vegfa-specific Cas9 RNP reduced the VEGFA mRNA level by 24±4% and the VEGFA protein level by 52±9% in confluent ARPE-19 cells under post-mitotic conditions.

Example 2: In Vitro and In Vivo Delivery of Cy3-Labeled Cas9 RNP

To monitor the localization of Cas9 RNPs in vitro and in vivo, Cy3-conjugated Cas9 protein (Reference Example 4). Thus, Cy3-Cas9 combined with or without the Vegfa-1 sgRNA was mixed with cationic lipids and delivered into NIH3T3 cells. Alternatively, the Vegfa-specific, Cy3-labeled or -unlabeled Cas9 RNP was delivered into an adult mouse eye via subretinal injection for the following experiments.

Figure 2A:
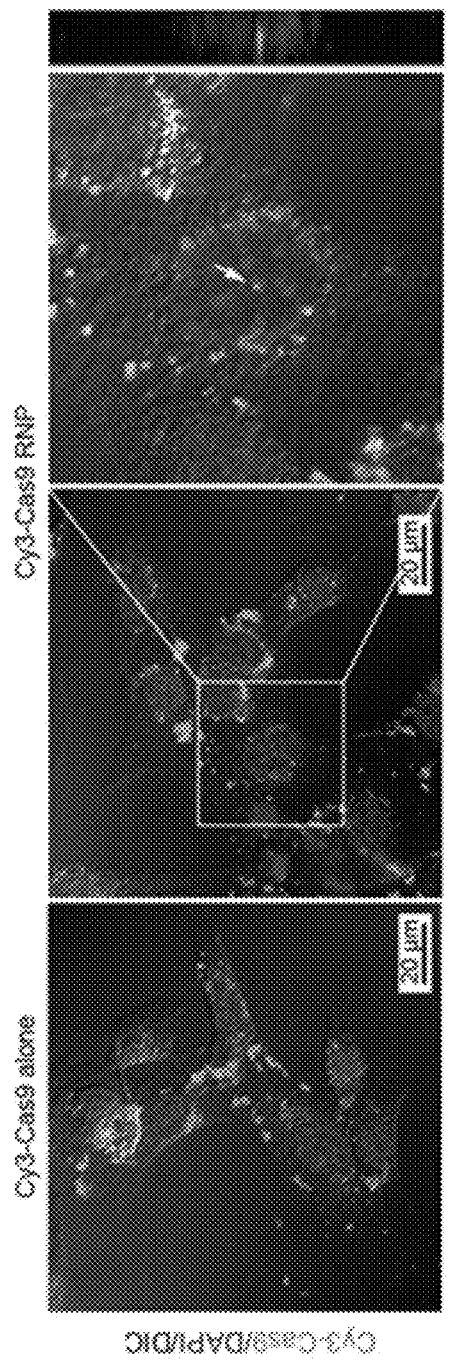
FIG. 2a shows confocal microscophic images of NIH3T3 cells 24 hours after transinfection with Cy3-labeled Cas9 RNP (a complex of Cy3-labeled Cas9 and Vegfa-1 sgRNA) or Cy3-labeled Cas9 alone (as a control)

NIH3T3 cells were transfected with Cy3-labeled Cas9 RNP (a complex of Cy3-labeled Cas9 and Vegfa-1 sgRNA) or Cy3-labeled Cas9 alone (as a control) and observed under a confocal microscope at 24 hours post-transfection to visualize Cy3 signals in the cells (see Reference Example 4). The images thus obtained are given FIG. 2a. In FIG. 2a, the white arrow indicates nuclear co-localization of Cy3 dye. The z-axis image on the right shows that Cy3-Cas9 is localized inside the nucleus.

Figure 2B:
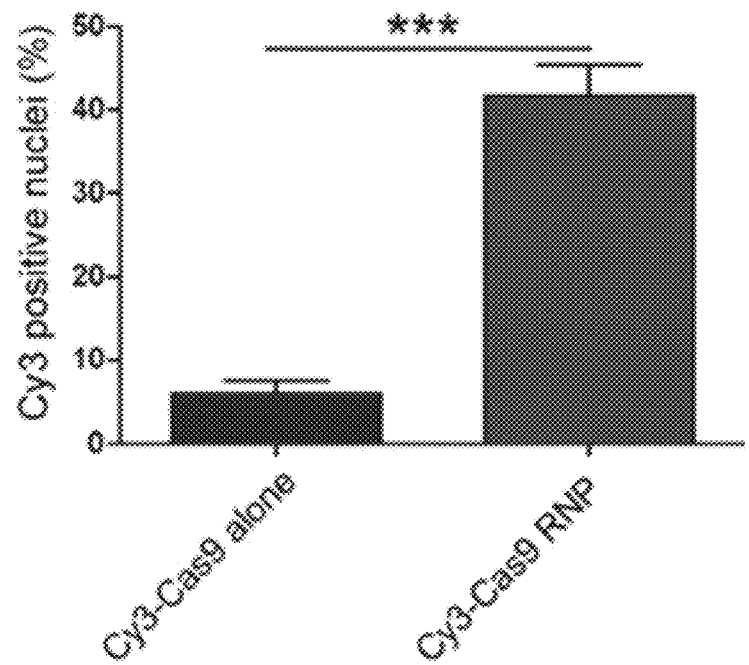
FIG. 2b is a graph showing the proportion of Cy3 positive nuclei in total DAPI positive nuclei (100*[number of Cy3-positive nuclei]/[total number of DAPI-positive nuclei]) at 24 hours after transfection with Cy3-labeled Cas9 or Cy3-labeled Cas9 alone.

In addition, measurement was made of the proportion of Cy3 positive nuclei in total DAPI positive nuclei (100* [number of Cy3-positive nuclei]/[total number of DAPI-positive nuclei]) at 24 hours post-transfection, and the results are depicted in FIG. 2b (Error bars indicate SEM (n=3). Student's t-test: *** P<0.001).

Figure 2C:
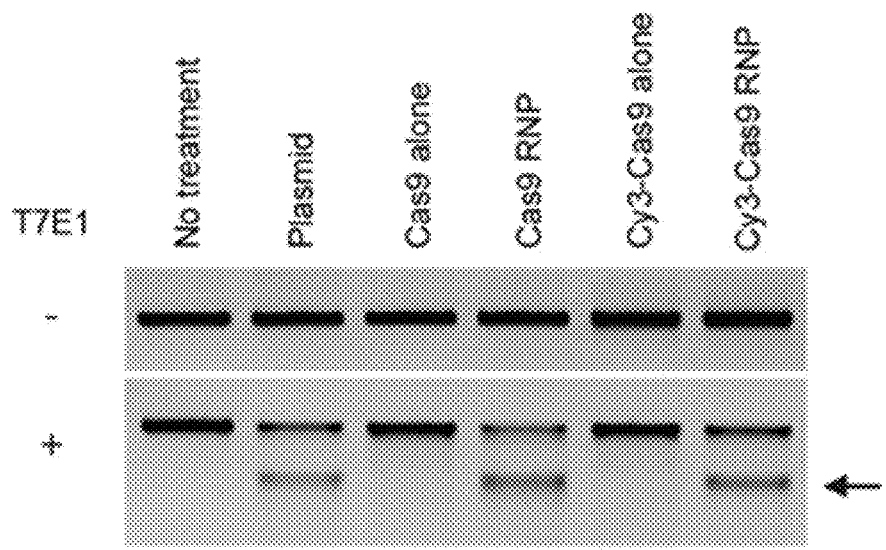
FIG. 2c shows mutations induced in NIH3T3 cells 24 hours post-transfection, as detected by T7 endonuclease 1 (T7E1) assay.

Mutations mediated by Vegfa-specific Cas9 RNP containing the Vegfa-1 sgRNA in NIH3T3 cells were detected by the T7 endonuclease 1 (T7E1) assay (see Reference Example 5) and are shown in FIG. 2c. In FIG. 2c, the arrow indicates the expected position of DNA bands cleaved by T7E1.

Figure 2D:
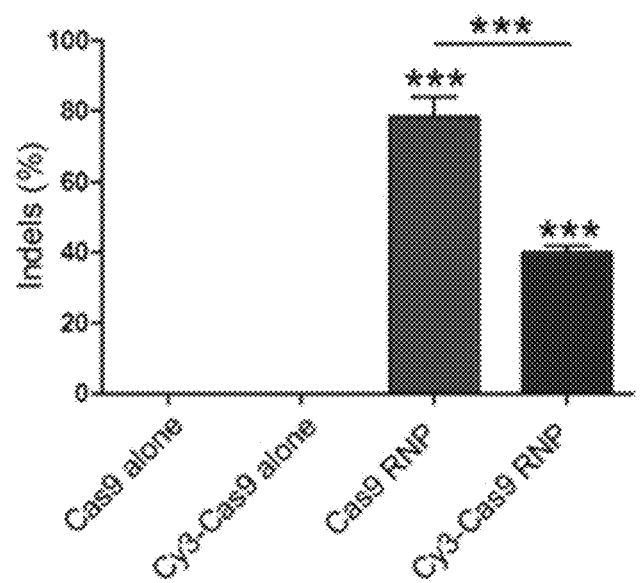
FIG. 2d is a graph showing indel frequencies induced in NIH3T3 cells 24 hours post-transfection.

Mutation frequencies driven by the Vegfa-specific Cas9 RNP containing the Vegfa-1 sgRNA in NIH3T3 cells were measured using targeted deep sequencing (see Reference Example 6) at 24 hours post-transfection and are shown in FIG. 2d (error bar: s.e.m (n=3); One-way ANOVA and Tukey post-hoc tests, *** P<0.001).

Figure 2E:
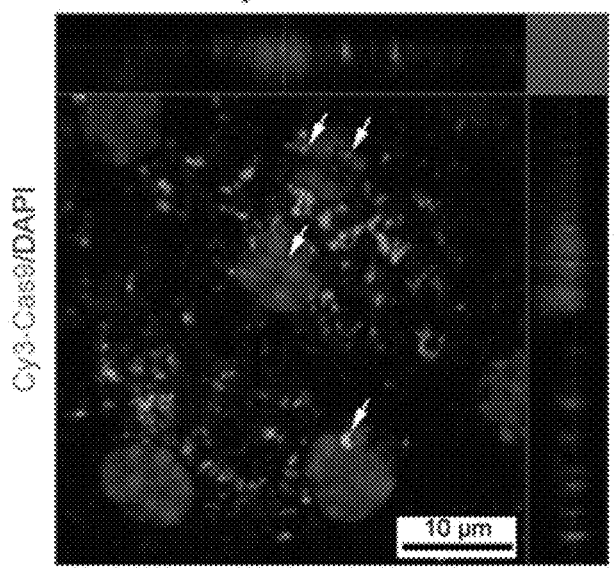
FIG. 2e is a fluorescent image of an RPE flat-mount at day 3 after the injection of the Cy3-labeled Cas9 RNP into mouse eye, as observed under a fluorescence microscope.

Representative RPE flat-mount at day 3 after the injection of Cy3-labeled Cas9 RNP into mouse eye was observed under a fluorescence microscope (see Reference Examples 11 and 12) and the results are given in FIG. 2e. In this figure, white arrows indicate nuclear colocalization of Cy3 dye.

Figure 2F:
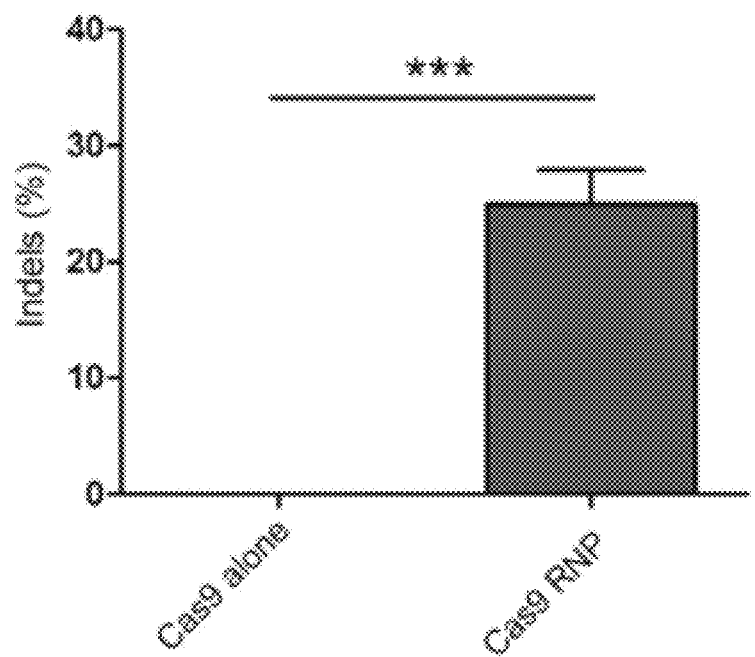
FIG. 2f is a graph showing in vivo indel frequencies induced in genomic DNAs DNA isolated from the retinal pigment epithelium (RPE)/choroid/scleral complexes at day 3 after injection of the Cy3-labeled Cas9 RNP.
Figure 2G:
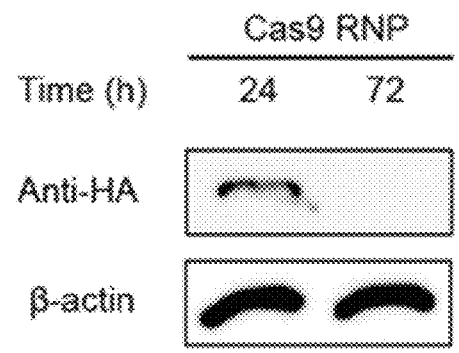
FIG. 2g shows Cas9 protein levels in RPE/choroid/scleral complexes 24 and 72 hours post-injection, as measured by Western blot analysis.
Figure 2H:
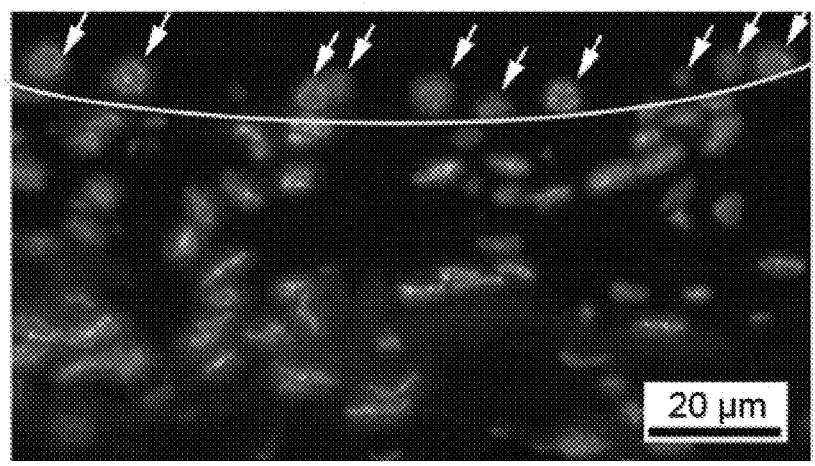
FIG. 2h is a fluorescent image showing the distribution of retinal pigment epithelium (RPE) in the RPE/choroid/scleral complex, as observed under a fluorescence microscope.

Distribution of retinal pigment epithelium (RPE) in the RPE/choroid/scleral complex was observed under a fluorescence microscope (see Reference Examples 11 and 12), and the results are shown in FIG. 2h. FIG. 2h depicts a representative cross-section of the RPE/choroid/scleral complex. DAPI-positive RPE cells and other cells were counted in a high-power field area (100 μm×100 μm). In FIG. 2h, the yellow line indicates a boundary between RPE and choroid and white arrows indicate RPE nuclei in the RPE/choroid/scleral complex (10.5±2.8%, n=8).

Indel frequencies induced in vivo were determined using genomic DNA isolated from the retinal pigment epithelium (RPE)/choroid/scleral complexes, with reference to Reference Example 13. Indels were analyzed by deep sequencing (see Reference Example 6) at day 3 post-injection. The results are depicted in FIG. 2f (Error bars are s.e.m. (n=6), Student's t-test, ** P<0.01).

Mutant DNA sequences induced by Vegfa-specific Cas9 RNPs (containing Vegfa-1 sgRNA) in vivo are depicted in FIG. 5: (a) Representative mutant DNA sequences induced by the Vegfa-specific Cas9 RNP in RPE at day 3 post-injection; and (b) Mutant DNA sequences in RPE containing laser-induced choroidal neovascularization (CNV) at day 7 post-injection. The PAM sequence is shown in red. WT denotes wild-type. The column on the right indicates the number and frequency of inserted or deleted nucleotides.

Western blot analysis was performed to measure the level of Cas9 protein in the RPE/choroid/scleral complex 24 and 72 hours after injection (n=4), and the results are shown in FIGS. 2g and 2i.

FIGS. 2a to 2d show in vitro results. Cy3-Cas9 RNP was detected in many nuclei, as shown in FIGS. 2a and 2b, and was observed to induce indels at the target site, as shown in FIGS. 2c and 2d.

The proportion of Cy3 positive nuclei (42±6%) (FIG. 2b) upon treatment with Cy3-Cas9 RNP was almost equal to the frequency of indels (40±3%) (FIG. 2d) at the target site, suggesting that target sites were almost completely cleaved in cells by nucleus-localized Cas9 and that the rate-limiting factor in genome editing was nuclear localization of Cas9. When delivered alone without sgRNA, Cy3-Cas9 was rarely detected in nuclei and did not induce indels (FIGS. 2a and 2d). Cas9 is a positively charged protein with a pI value of 9.12 and cannot form a complex with cationic lipids in the absence of negatively charged sgRNAs. However, the Cy3-Cas9 RNP was less active than the unlabeled Cas9 RNP, which induced target-specific mutations at a frequency of 80% (FIG. 2d).

FIGS. 2e to 2i show in vivo results. Cy3 dye was observed in the nuclei of the RPE in vivo 3 days after the injection of Cy3-Cas9 RNP (in vivo, FIG. 2e). Because RPE is a major target of the RNP delivery by retinal injection, RPE alone allows for the ideal analysis of mutation frequencies. Actually, however, it is not easy to classify RPE for use in targeted deep sequencing from the RPE/choroid/scleral complex. Instead, DAPI-positive nuclei were counted to calculate the proportion of RPE, which accounted for 11±3% of the RPE/choroid/scleral complex (FIG. 2h).

Notably, the subretinal injection of the Cy3-unlabeled Cas9 RNP gave rise to indels with a frequency of 16±2% at day 3 post-injection, with the consequent editing in most target sites of the Vegfa gene in RPE in vivo (n=6, FIGS. 2f and 5a). Through Western blot analysis, it was also found that the Cas9 protein was degraded completely at day 3 post-injection (FIGS. 2g and 2i), indicating that Cas9 was rapidly turned over in vivo.

Example 3: Assay for Effect of Retinal Injection of Vegfa-Targeting Cas9 RNP on Age-Related Macular Degeneration (AMD) and Laser-Induced Choroidal Neovascularization (CNV)

In order to investigate whether the Cas9 RNP could be used for the treatment of CNV in AMD mouse models, mice with laser-induced CNV were treated by subretinal injection of the Vegfa-specific Cas9 RNP (containing Vegfa-1 sgRNA) or Rosa26-specific Cas9 RNP (Rosa26-RNP; containing Rosa26 sgRNA). Since retinal injection itself increases the size of CNV, the Rosa26-RNP was used as a negative control.

Figure 3A:
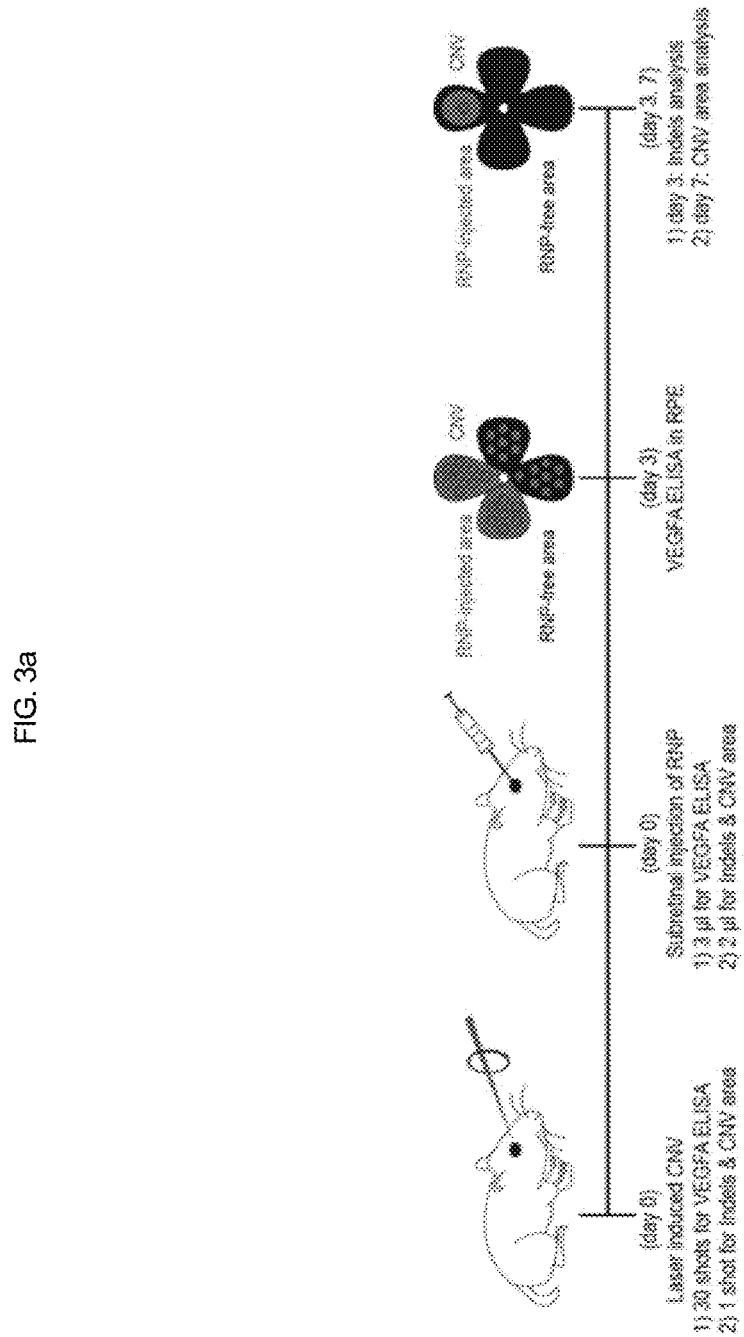
FIG. 3a is a schematic diagram illustrating the experimental procedure of Example 3.

Mice with laser-induced CNV were administered with the preassembled Vegfa-specific Cas9 RNP by retinal injection. After the retinal pigment epithelium (RPE) complex in the eye was flat-mounted, the CNV area was analyzed at day 7 post-injection. Genomic DNA isolated from the Cas9 RNP-injected area or from the opposite non-injected area (RNP-free area) was analyzed by deep sequencing. Vegfa ELISA was performed at day 3 post-injection. This procedure is schematically shown in FIG. 3a.

Figure 3B:
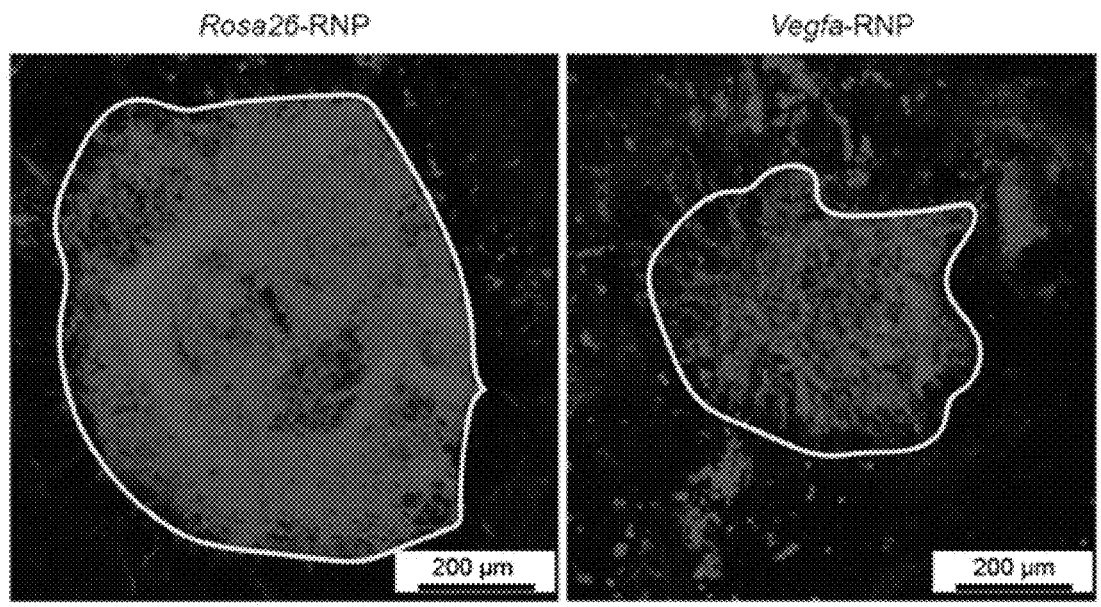
FIG. 3b shows images visualizing laser-induced CNV stained with isolectin B4 (IB4) in C576L/6J mice injected with the Rosa26-specific Cas9 RNP (as a control) or the Vegfa-specific Cas9 RNP at day 7 post-injection.

Laser-induced CNV stained with isolectin B4 (IB4) in C576L/6J mice injected with the Rosa26-specific Cas9 RNP (as a control) or the Vegfa-RNP at day 7 post-injection was visualized (see Reference Example 11). Representative images are shown in FIG. 3b. The yellow line demarcates the area of CNV.

At day 3 post-injection, a therapeutic effect was evaluated by assessing the CNV area. CNV areas were measured in C57BU6J mice injected with the Vegfa-specific Cas9 RNP with reference to Reference Example 11 and are depicted as relative values (%) to the CNV area (100%) of the control injected with the Rosa26-specific Cas9 RNP in FIG. 3c (Error bars indicate s.e.m. (n=15), Student's t-test, *** P<0.001).

Figure 3C:
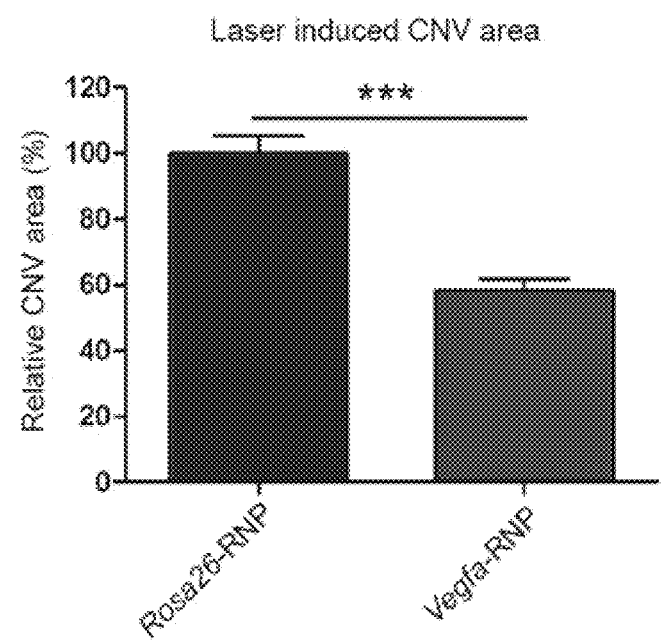
FIG. 3c is a graph showing the comparison of CNV areas in C576L/6J mice injected with the Vegfa-specific Cas9 RNP and a control injection with the Rosa26-specific Cas9 RNP.
Figure 3D:
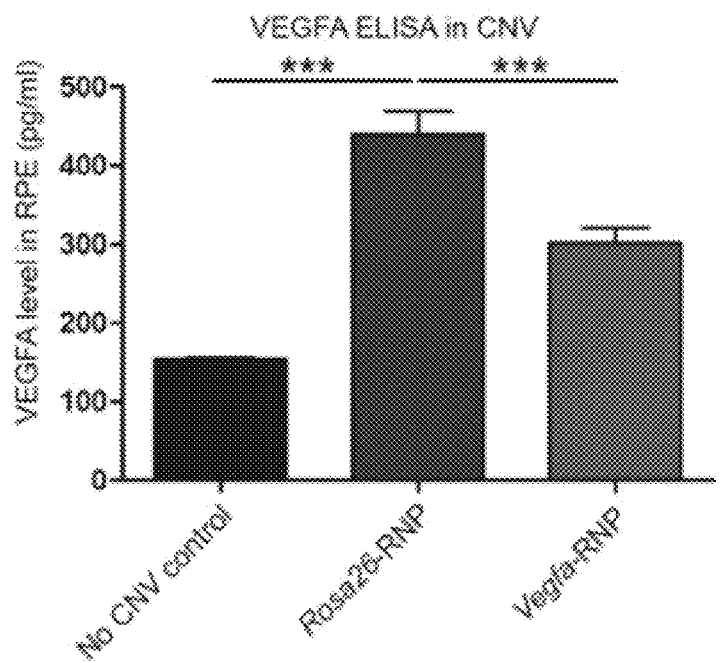
FIG. 3d is a graph showing Vegfa protein levels in CNV areas.

Vegfa levels (pg/ml) in CNV areas were measured by ELISA (see Reference Example 14), and the results are shown in FIG. 3d (Error bars indicate s.e.m. (n=10), Student's t-test, ** P<0.01).

Figure 3E:
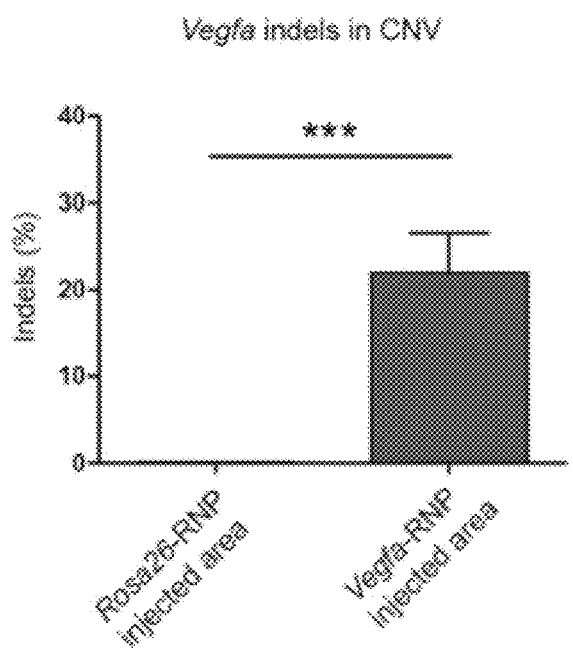
FIG. 3e is a graph of indel frequencies (%) at Vegfa target sites in the RPE complexes.

Indel frequencies (%) at the Vegfa target site in the RPE complex are shown in FIG. 3e (Error bars indicate s.e.m. (n=7), One-way ANOVA and Tukey post-hoc tests, *** P<0.001).

Figure 3F:
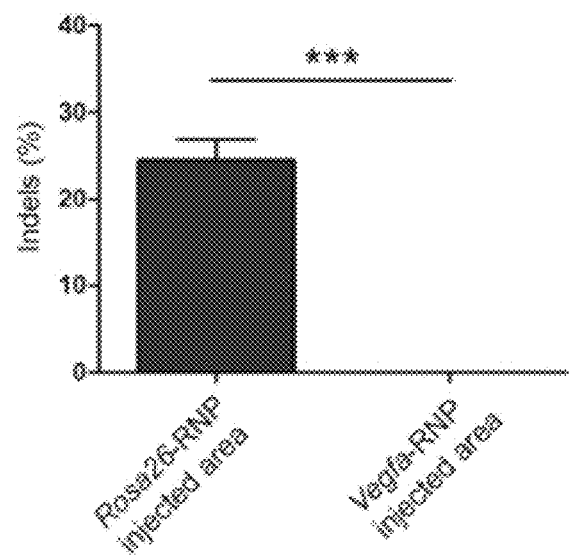
FIG. 3f is a graph of indel frequencies (%) at Rosa26 target sites in the RPE complexes.

Indel frequencies (%) at the Rosa26 target site in the RPE complex are shown in FIG. 3f (Error bars indicate s.e.m. (n=7), Student's t-test, * P<0.05).

Figure 3G:
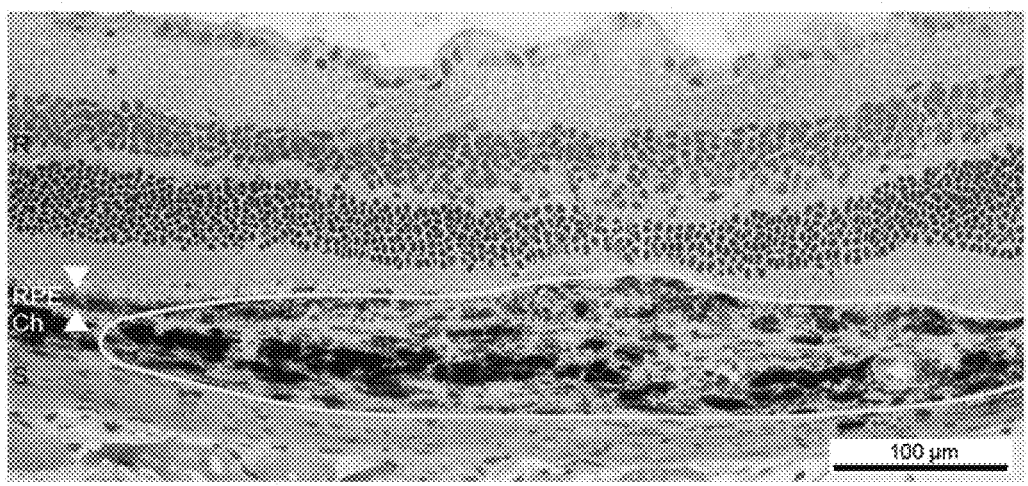
FIG. 3g is an image of a laser-induced CNV structure in a cross-section sample, as visualized by hematoxylin & eosin staining.

The laser-induced CNV structure in a cross-section sample was visualized by hematoxylin & eosin staining and is shown in FIG. 3g. In FIG. 3g, the yellow line indicates a CNV boundary and white triangles indicate a retinal pigment epithelium (RPE) layer in the RPE/choroid/scleral complex. Most RPE cells were observed to be injured in the CNV area (Ch: choroid, R: retina, S: sclera).

Figure 3H:
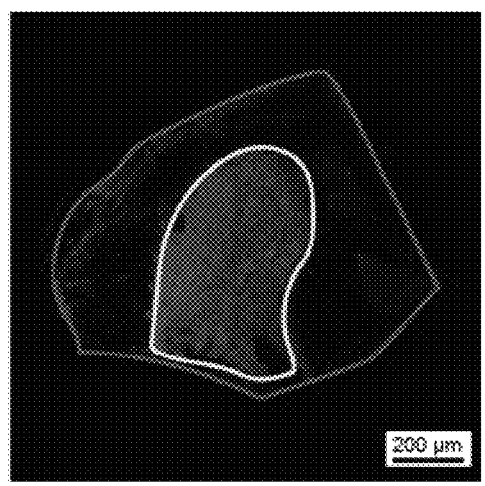
FIG. 3h shows a CNV sample for use in mutation analysis through targeted deep sequencing.

A representative CNV sample for use in mutation analysis through targeted deep sequencing is shown in FIG. 3h. In FIG. 3h, the red line indicates a boundary of the RPE/choroid/scleral complex for mutation analysis. RPE cells predominantly existed outside the CNV area limited by the yellow line.

Figure 3I:
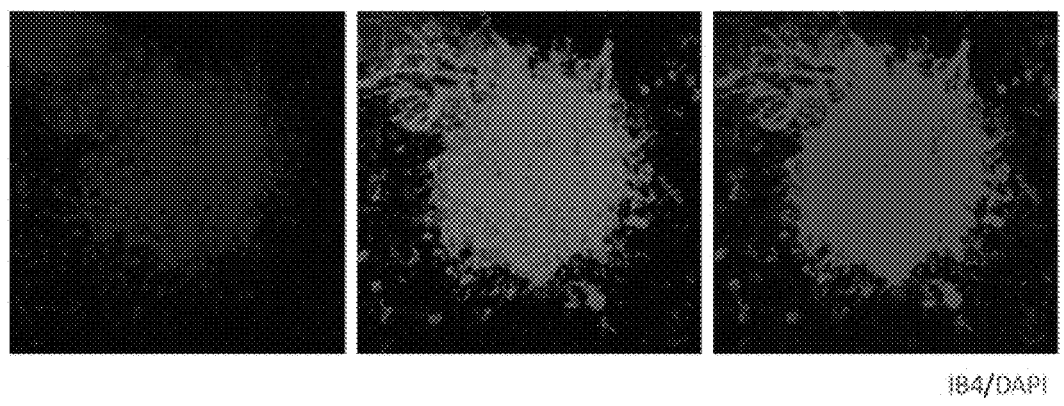
FIG. 3i shows images of laser-induced CNV at day 7 after laser treatment.

Laser-induced CNV at day 7 after laser treatment is depicted in FIG. 3i. Epithelial cells co-stained with 1B4 marker and DAPI were collected into the CNV areal (middle).

As shown in FIGS. 3b and 3c, a significant reduction of CNV area was found in the Vegfa-RNP-injected mice, compared to the Rosa26-RNP-injected mice (58±4% relative to Rosa26-RNP-injected mice, n=15, P<0.001, Student's t-test).

In addition, as shown in FIG. 3d, the injection of Vegfa-specific Cas9 RNP effectively reduced the concentration of the Vegfa protein (300±20 pg/ml, n=10)) in the CNV area, compared to the injection of Rosa26-RNP (440±30 pg/ml, n=10).

As understood from FIGS. 3e and 3f, indel frequencies in RNP target sites in the Vegfa-specific Cas9 RNP-treated CNV and the Rosa26-RNP-treated CNV (see FIG. 5b) were detected to be 3.5±0.3% (Vegfa indel) and 3.3±1.0% (Rosa26 indel), respectively, whereas indels were not detected in the negative control at all. This result suggests that subretinal injection of the Vegfa-specific Cas9 RNP can lead to local treatment even in the eye.

FIG. 3g shows that most RPE cells in CNV were killed by laser treatment. Gene editing by Cas9 RNP was not effected in dead cells, but only in viable RPE cells (FIG. 3h). As a result, lower indel frequencies were detected in viable RPE cells than in cells in CNV-free areas. At day 3 after laser treatment, epithelial cells gathered in the CNV area to form new vessels (FIG. 3i). Indel frequencies further decreased I the CNV area as the cells were not be gene edited. These results suggest that that targeted inactivation of Vegfa in the eye using Cas9 RNPs enables therapeutic genome surgery for the local treatment of AMD.

A critical issue in therapeutic genome therapy is the target specificity of CRISPR-Cas9. It was examined whether the Vegfa-specific Cas9 RNP used in this experiment caused any off-target mutations in the mouse eye or in human cells. First, 20 potential off-target sites in the mouse genome that are the most homologous to the target sequence of Vegfa-sgRNA of the Cas9 RNP were identified using Cas-OFFinder and are summarized in Table 7, below.

TABLE 7

Potential off-target sites of the Vegfa-1 sgRNA (with PAM) in the mouse genome

| No. | Gene | | Sequence | Chromo-some | Position | Direction |
|---|---|---|---|---|---|---|
| On | Vegfa | Exon | CTCCTGGAAGATGTC-CACCAGGG (SEQ ID NO: 293) | chr17 | 46025487 | − |
| OT1 | Intergenic-region | | CTCCTGGAAGATTTT-CACCAGGG (SEQ ID NO: 297) | chr2 | 123023449 | − |
| OT2 | Arhgef7 | Intron | CTCCTGGAA-GATCTCCAGGAAGG (SEQ ID NO: 298) | chr8 | 11735358 | − |
| OT3 | Gsc | Exon | CTCCTG-GAAGAGGTTCTCCAGGG (SEQ ID NO: 299) | chr12 | 104472064 | + |
| OT4 | Ptpm2 | Exon | CTCTTGGCAGATGTC-CACAAGGG (SEQ ID NO: 300) | chr12 | 116842612 | + |
| OT5 | Gpr139 | Intron | CTCCTGGAAGCTGCC-CATCATGG (SEQ ID NO: 301) | chr7 | 119178456 | − |
| OT6 | Kank4 | Intron | CTCCTGGAAAATGCC-CACCCTGG (SEQ ID NO: 302) | chr4 | 98816689 | + |

TABLE 7-continued

Potential off-target sites of the Vegfa-1 sgRNA (with PAM) in the mouse genome

| No. | Gene | | Sequence | Chromosome | Position | Direction |
|---|---|---|---|---|---|---|
| OT7 | Stk32b | Intron | CTCCTGGAA-GATGTGGGCCATGG (SEQ ID NO: 303) | chr5 | 37675822 | − |
| OT8 | Ptpn11 | Intron | CTCCTGAAAGCTGAC-CAC CACGG (SEQ ID NO: 304) | chr5 | 121146230 | + |
| OT9 | Acad12 | Intron | CACATGGAGGATGTC-CAC CATGG (SEQ ID NO: 305) | chr5 | 121606239 | + |
| OT10 | Intergenic—region | | CTCCTG-GAAGCTGTTGACC AGGG (SEQ ID NO: 306) | chr5 | 138824186 | + |
| OT11 | Intergenic—region | | CTCCTG-GAAGAGGACAAC CAAGG (SEQ ID NO: 307) | chr13 | 44510080 | − |
| OT12 | Fibp | Exon | CTGCTGGATGTTGTC-CACC AGGG (SEQ ID NO: 308) | chr19 | 5462580 | − |
| OT13 | Intergenic—region | | CTCCTG-GAAGTTGTCCTCC TTGG (SEQ ID NO: 309) | chr15 | 87360502 | − |
| OT14 | Intergenic—region | | CCCCTGGAAGATTTC-CATC AAGG (SEQ ID NO: 310) | chr17 | 37793411 | + |
| OT15 | Intergenic—region | | CTCTTGGCAGCTGTC-CACC ATGG (SEQ ID NO: 311) | chr10 | 24365585 | − |
| OT16 | Intergenic—region | | CTCCAAGAA-GATGTCCTCC ATGG (SEQ ID NO: 312) | chr10 | 55869098 | − |
| OT17 | Fam180a | Exon | CTCCTGGAA-GATGTCCTGG AAGG (SEQ ID NO: 313) | chr6 | 35325901 | − |
| OT18 | Rasgrf1 | Exon | CTCCTGGTA-GATGTTCAGC ATGG (SEQ ID NO: 314) | chr9 | 89970376 | − |
| OT19 | Abca13 | Intron | GTCCTGGAAGCTGTC-CAC AAAGG (SEQ ID NO: 315) | chr11 | 9509771 | + |
| OT20 | C130046K22Rik | Intron | CTCAGTGAAGATGTC-CACC AAGG (SEQ ID NO: 316) | chr11 | 103713336 | + |

Figure 6:
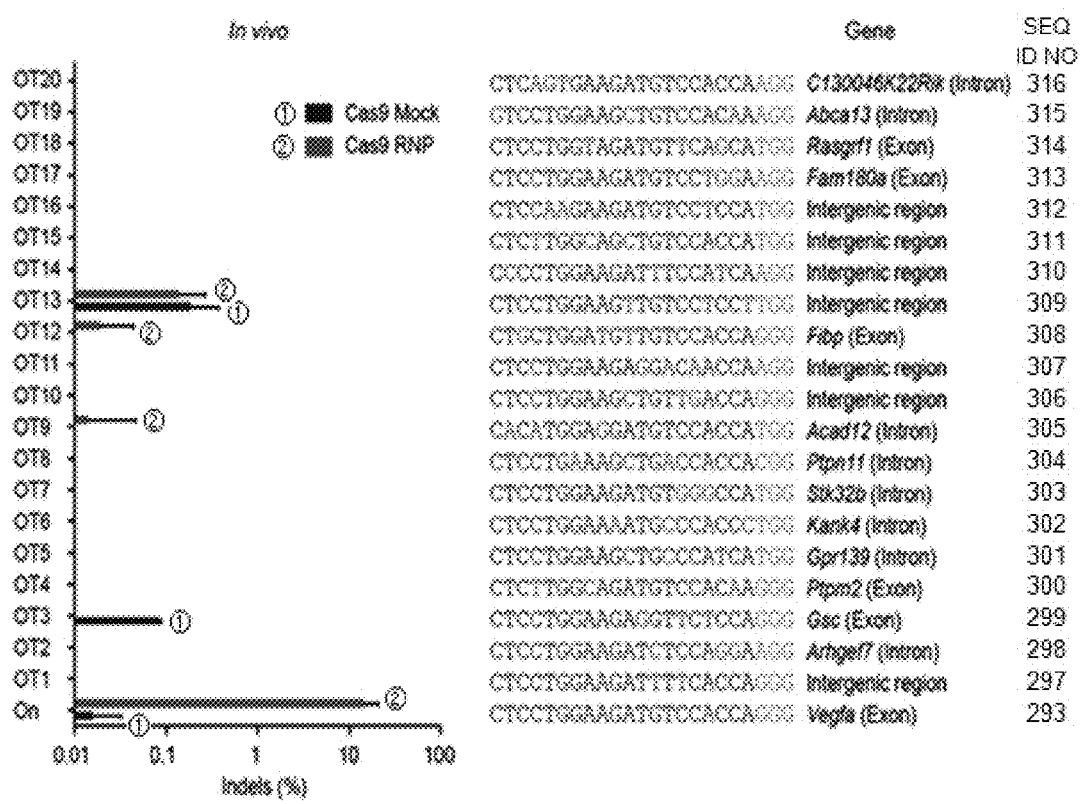
FIG. 6 shows indel frequencies (%) in 20 potential off-target sites of mouse RPE.

Genomic DNA isolated from the CNV-free RPC complex of the Cas9 RNP-treated mouse eye was subjected to targeted deep sequencing to indel frequencies (%) in the 20 potential off-target sites. The results are depicted in FIG. 6 (Error bars indicate s.e.m. (n=3 for Cas9 Mock, n=5 for Cas9 RNP, respectively). Mismatched nucleotides and PAM sequences are shown in red and blue, respectively. At the 20 potential off-target sites treated with the Cas9 RNP, no Cas9-induced indels were detected with a frequency greater than 0.1%, demonstrating that no off-target mutations were induced above sequencing error rates (sequencing error rate; average 0.1%). That is, the Vegfa-specific Cas9 RNP used in the present disclosure was found to exhibit no off-target effects in RPE.

Example 4: Assay for Genome-Wide Target Specificity of Vegfa-Specific Cas9 RNP in Human Genome Genome-wide target specificity of the Vegfa-specific Cas9 RNP in the human genome was revealed by Digenome-seq (see Reference Examples 6 and 9).

Figure 4A:
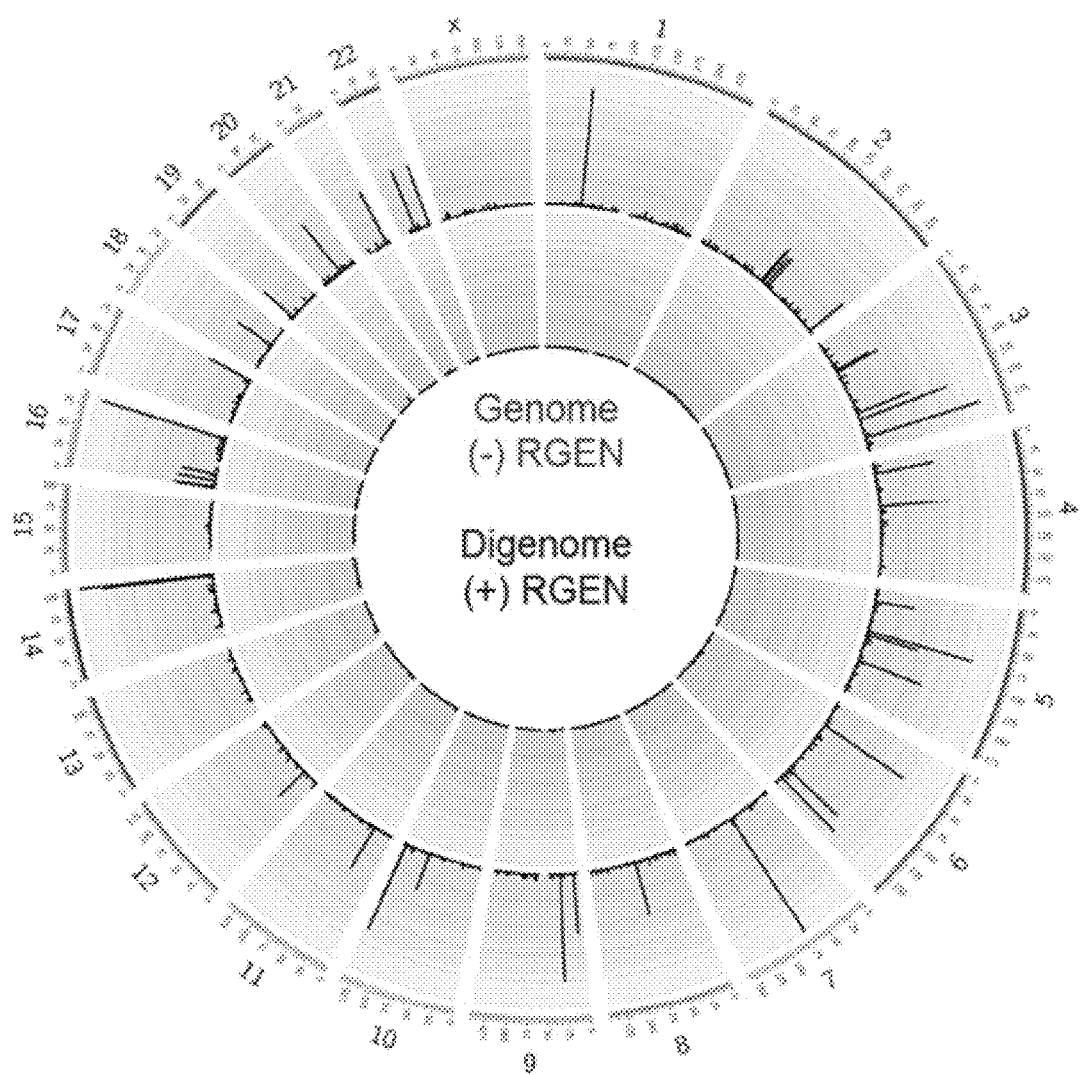
FIG. 4a is a genome-wide Circos plot showing in vitro cleavage sites.

FIG. 4a is a genome-wide Circos plot showing in vitro cleavage sites. Human genomic DNA is shown in red, and RGEN-digested genomic DNA is shown in blue.

Figure 4B:
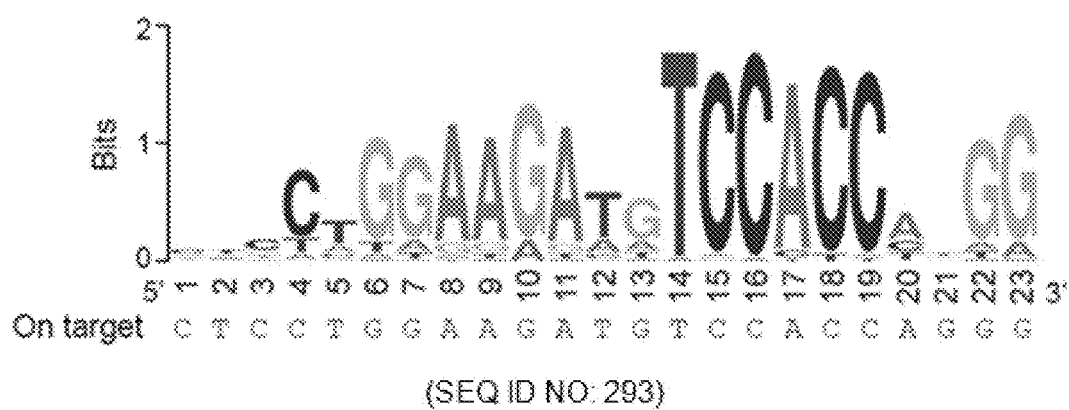
FIG. 4b shows sequence logos obtained using 42 sequences including 41 Digenome-capture sites and one On-target sequence.

Sequence logos obtained using 42 sequences including 41 Digenome-capture sites and one On-target sequence are given in FIG. 4b.

Figure 4C:
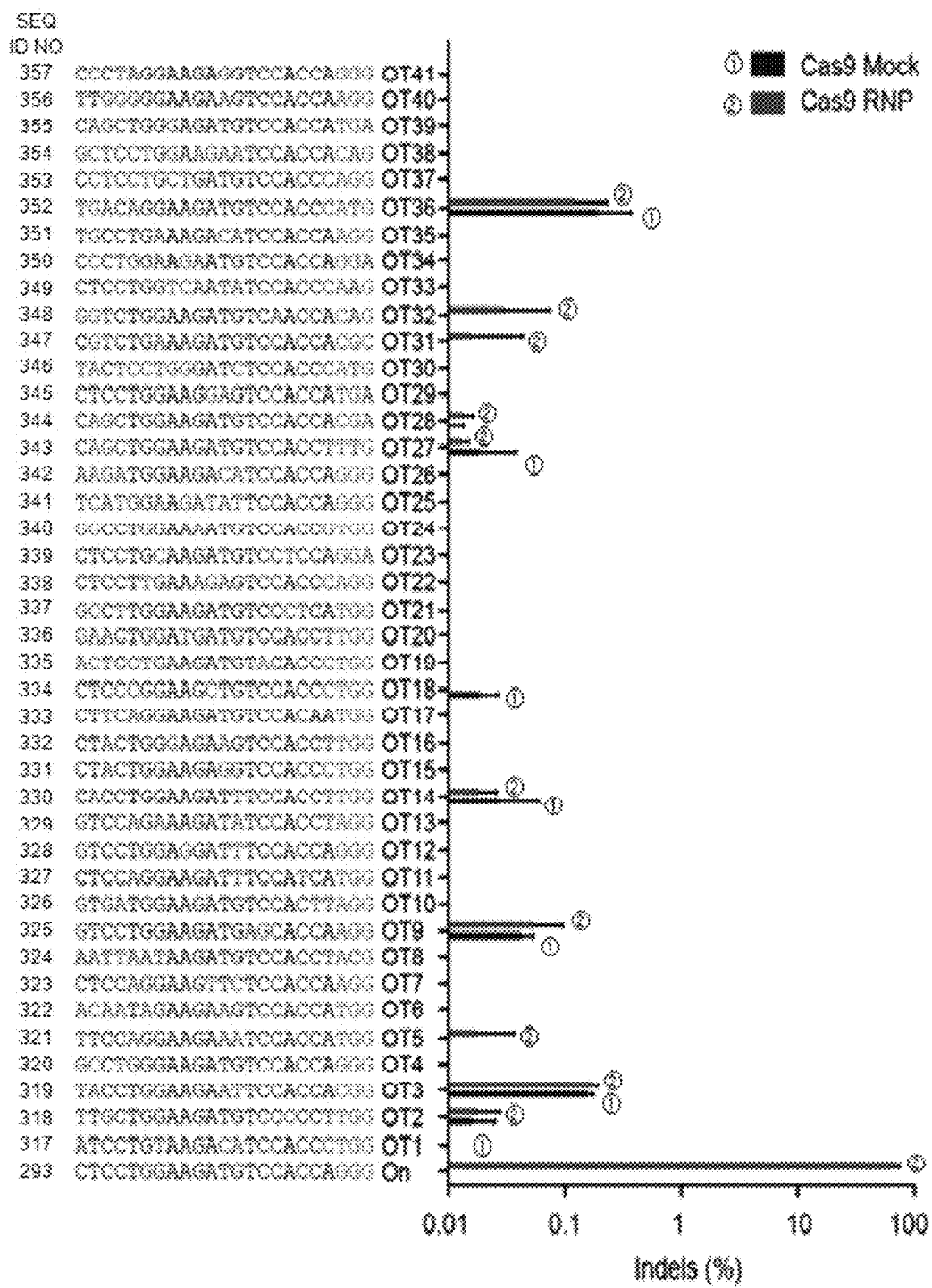
FIG. 4c shows off-target sites and indel frequencies validated in human ARPE-19 cells.

Off-target sites and indel frequencies validated in human ARPE-19 cells by targeted deep sequencing are shown in FIG. 4c. Mismatched nucleotides are shown in red, and PAM sequences are shown in blue.

The particular target sequence of the Vegfa-specific Cas9 RNP shown in FIGS. 4a and 4b is well conserved in the human VEGFA gene.

The human genome-wide specificity was assessed using Digenome-seq (Kim et al., Nature Methods 12, 237-243 (2015)) in which cell-free human genomic DNA was treated in vitro using the Vegfa-specific Cas9 RNP and then subjected to whole-genome sequencing. Uniform, rather than random, alignments of sequence reads at in vitro cleavage sites are computationally identified to provide a list of potential off-target sites. Digenome-seq using the Vegfa-specific Cas9 RNP revealed 42 in vitro cleavage sites including the on-target site and the sites are summarized in Table 8, below.

TABLE 8

In vitro cleavage sites in the human genome identified by Digenome-seq using the VEGFA sgRNA

| No. | Gene | | Sequence | Chromosome | Position | Direction |
|---|---|---|---|---|---|---|
| On | VEGFA | Exon | CTCCTGGAAGATGTCCACCA GGG (SEQ ID NO: 293) | chr6 | 43745263 | - |
| OT1 | NAALADL2 | Intron | ATCCTGTAAGACATCCACCC TGG (SEQ ID NO: 317) | chr3 | 174605831 | - |
| OT2 | Intergenic region | – | TTGCTGGAAGATGTCCCCCT GG (SEQ ID NO: 318) | chr12 | 28147929 | - |
| OT3 | CPNE4 | Intron | TACCTGGAAGAATTCCACCA CGG (SEQ ID NO: 319) | chr3 | 131485198 | - |
| OT4 | ABTB2 | Intron | GCCTGGGAAGATGTCCACC AGGG (SEQ ID NO: 320) | chr11 | 34241888 | - |
| OT5 | ARFGEF3 | Intron | TTCCAGGAAGAAATCCACCA TGG (SEQ ID NO: 321) | chr6 | 138531951 | - |
| OT6 | Intergenic region | – | ACAATAGAAGAAGTCCACC ATGG (SEQ ID NO: 322) | chr5 | 21242334 | + |
| OT7 | BAIAP2-AS1 | Exon | CTCCAGGAAGTTCTCCACCA AGG (SEQ ID NO: 323) | chr17 | 7900648 | - |
| OT8 | HOMER1 | Intron | AATTAATAAGATGTCCACCT ACG (SEQ ID NO: 324) | chr5 | 78719511 | - |
| OT9 | ABCA3 | Exon | GTCCTGGAAGATGAGCACC AAGG (SEQ ID NO: 325) | chr16 | 2327650 | - |
| OT10 | Intergenic region | – | GTGATGGAAGATGTCCACTT AGG (SEQ ID NO: 326) | chr2 | 129298046 | - |
| OT11 | Intergenic region | – | CTCCAGGAAGATTTCCATCA TGG (SEQ ID NO: 327) | chr4 | 16957810 | + |
| OT12 | Intergenic region | – | GTCCTGGAGGATTTCCACCA GGG (SEQ ID NO: 328) | chr8 | 70150186 | - |
| OT13 | DSCAM | Intron | GTCCAGAAAGATATCCACCT AGG (SEQ ID NO: 329) | chr21 | 42029091 | - |
| OT14 | CLIP2 | Intron | CACCTGGAAGATTTCCACCT TGG (SEQ ID NO: 330) | chr7 | 73770600 | + |
| OT15 | Intergenic region | – | CTACTGGAAGAGGTCCACC CTGG (SEQ ID NO: 331) | chr14 | 103748791 | + |
| OT16 | ACSS2 | Intron | CTACTGGGAGAAGTCCACC TTGG (SEQ ID NO: 332) | chr20 | 33506330 | + |

TABLE 8-continued

In vitro cleavage sites in the human genome identified by Digenome-seq using the VEGFA sgRNA

| No. | Gene | | Sequence | Chromosome | Position | Direction |
|---|---|---|---|---|---|---|
| OT17 | Intergenic region | – | CTTCAGGAAGATGTCCACAA TGG (SEQ ID NO: 333) | chr4 | 74527941 | + |
| OT18 | Intergenic region | – | CTCCCGGAAGCTGTCCACC CTGG (SEQ ID NO: 334) | chr14 | 106089679 | + |
| OT19 | ITIH4, RP5-966M1.6 | Intron | ACTCCTGAAGATGTACACCC TGG (SEQ ID NO: 335) | chr3 | 52863033 | + |
| OT20 | Intergenic region | – | GAACTGGATGATGTCCACCT TGG (SEQ ID NO: 336) | chr6 | 157061270 | + |
| OT21 | LINC01170 | Exon | GCCTTGGAAGATGTCCCTCA TGG (SEQ ID NO: 337) | chr5 | 123650052 | + |
| OT22 | Intergenic region | – | CTCCTTGAAAGAGTCCACCC AGG (SEQ ID NO: 338) | chr2 | 236108683 | + |
| OT23 | Intergenic region | – | CTCCTGCAAGATGTCCTCCA GGA (SEQ ID NO: 339) | chr2 | 120420942 | - |
| OT24 | Intergenic region | – | GGCCTGGAAAATGTCCACC GTGG (SEQ ID NO: 340) | chr2 | 122905021 | + |
| OT25 | MGAT5 | Intron | TCATGGAAGATATTCCACCA GGG (SEQ ID NO: 341) | chr2 | 134952386 | - |
| OT26 | U91319.1 | Intron | AAGATGGAAGACATCCACC AGGG (SEQ ID NO: 342) | chr16 | 13592695 | + |
| OT27 | Intergenic region | – | CAGCTGGAAGATGTCCACCT TTG (SEQ ID NO: 343) | chr16 | 84252079 | + |
| OT28 | Intergenic region | – | CAGCTGGAAGATGTCCACC ACGA (SEQ ID NO: 344) | chr1 | 59037909 | + |
| OT29 | Intergenic region | – | CTCCTGGAAGGAGTCCACC ATGA (SEQ ID NO: 345) | chr5 | 72463793 | + |
| OT30 | SLC9A9 | Intron | TACTCCTGGGATCTCCACCC ATG (SEQ ID NO: 346) | chr3 | 143166935 | - |
| OT31 | PTPRS | Exon | CGTCTGAAAGATGTCCACCA CGC (SEQ ID NO: 347) | chr19 | 5207995 | + |
| OT32 | Intergenic region | – | GGTCTGGAAGATGTCAACCA CAG (SEQ ID NO: 348) | chr10 | 131177201 | - |
| OT33 | Intergenic region | – | CTCCTGGTCAATATCCACCC AAG (SEQ ID NO: 349) | chr22 | 25944921 | + |
| OT34 | ERC2 | Intron | CCCTGGAAGAATGTCCACC AGGA (SEQ ID NO: 350) | chr3 | 55563577 | + |
| OT35 | CTD-2130O13.1 | Intron | TGCCTGAAAGACATCCACCA AGG (SEQ ID NO: 351) | chr18 | 44830053 | - |
| OT36 | Intergenic region | – | TGACAGGAAGATGTCCACC CATG (SEQ ID NO: 352) | chr9 | 28979308 | + |
| OT37 | Intergenic region | – | CCTCCTGCTGATGTCCACCC AGG (SEQ ID NO: 353) | chr16 | 1065437 | + |
| OT38 | Intergenic region | – | GCTCCTGGAAGAATCCACC ACAG (SEQ ID NO: 354) | chr10 | 130753819 | + |
| OT39 | BRD1 | Intron | CAGCTGGGAGATGTCCACC ATGA (SEQ ID NO: 355) | chr22 | 50174426 | + |
| OT40 | CACNG3 | Intron | TTGGGGGAAGAAGTCCACC AAGG (SEQ ID NO: 356) | chr16 | 24310237 | + |

TABLE 8-continued

In vitro cleavage sites in the human genome identified by Digenome-seq using the VEGFA sgRNA

| No. | Gene | | Sequence | Chromosome | Position | Direction |
|---|---|---|---|---|---|---|
| OT41 | RP11-57C13.6, RP11-57C13.3 | Intron | CCCTAGGAAGAGGTCCACCAGGG (SEQ ID NO: 357) | chr10 | 89404735 | - |

To examine the validity of the sites listed in Table 8, targeted deep sequencing was performed using genomic DNA isolated from Vegfa-specific RNP-transfected ARPE-19 cells (see FIG. 4c). Although these sites were cleaved efficiently in vitro, off-target indels were not detected at these 41 cleavage sites above sequencing error rates (average 0.1%).

Modified gRNAs with improved specificity (Fu, Y., Sander, J. D., Reyon, D., Cascio, V. M. & Joung, J. K. Improving CRISPR-Cas nuclease specificity using truncated guide RNAs. *Nature biotechnology* 32, 279-284 (2014); Cho, S. W. et al. Analysis of off-target effects of CRISPR/Cas-derived RNA-guided endonucleases and nickases. *Genome research* 24, 132-141 (2014)) or Cas9 variants (Kleinstiver, B. P. et al. High-fidelity CRISPR-Cas9 nucleases with no detectable genome-wide off-target effects. *Nature* 529, 490-495 (2016); Slaymaker, I. M. et al. Rationally engineered Cas9 nucleases with improved specificity. *Science* 351, 84-88 (2016)) may be used, if necessary, to further reduce or avoid the off-target effect that exists although slight.

Taken together, these results show that the Vegfa-specific RNP containing the sgRNA that has the Vegfa targeting sequence provided in the present disclosure is highly specific in both mouse and human cells (in vivo and in vitro).

Example 5: Assay for Side-Effect of Vegfa-Specific Cas9 RNP

Another major concern for mutating the Vegfa gene for the treatment of AMD or diabetic retinopathy is the trophic role of Vegfa in the eye. Cone dysfunction is the most significant change upon Vegfa mutating, and is observed 3 days after conditional deletion of the Vegfa gene in mouse RPE.

To examine whether the Vegfa-specific Cas9 RNP provided by the present disclosure caused cone dysfunction, such as ??, opsin-positive areas were observed using a fluorescence microscope and calculated. The results are depicted in FIGS. 7a (fluorescent image) and 7b (opsin positive area (%)).

Figure 7A:
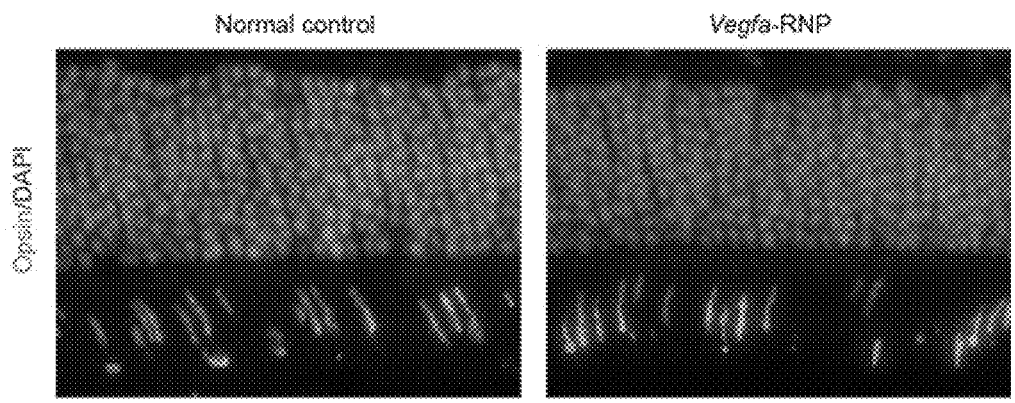
FIG. 7a shows fluorescent cross-sectional images of the respective retinas obtained 7 days after injection of the Vegfa-specific Cas9 RNP from a normal mouse injected with the Vegfa-specific Cas9 RNP and a normal control mouse without injection of the Vegfa-specific Cas9 RNP.
Figure 7B:
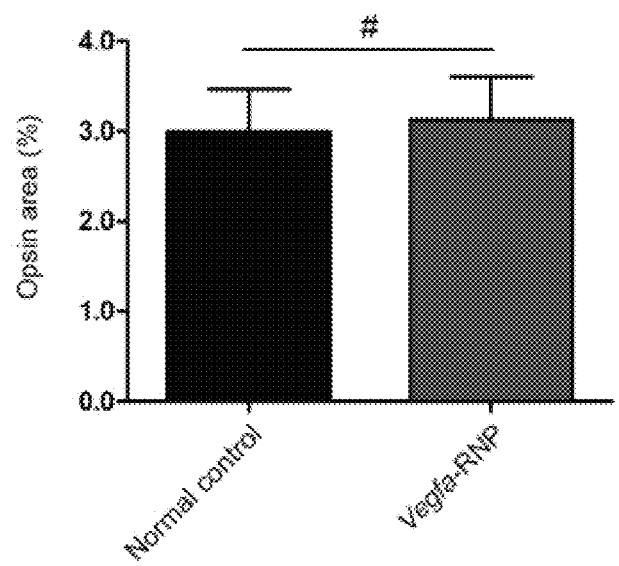
FIG. 7b is a graph showing opsin positive areas (%)

FIG. 7a shows fluorescent cross-sectional images of the respective retinas obtained 7 days after injection of the Vegfa-specific Cas9 RNP from a normal mouse injected with the Vegfa-specific Cas9 RNP (only RNP injection without laser treatment) and a normal control mouse without injection of the Vegfa-specific Cas9 RNP. Opsin appears in green and DAPI is shown in blue. FIG. 7b is a graph showing opsin positive areas (%), with no significant difference between the normal control (3.0±0.5%) and the Vegfa-specific Cas9 RNP-injected mice (3.1±0.5%) (Error bars indicate s.e.m. (n=4); #, P>0.05 (Student's t-test)).

As understood from FIGS. 7a and 7b, the mice injected with the Vegfa-specific Cas9 RNP provided by the present disclosure did not differ in the option positive area of cone cells from the non-injected normal control, even at day 7 after treatment, suggesting that no cone dysfunction had occurred. These results imply that the Vegfa-specific Cas9 RNP specifically mutates only target sequences of the Vegfa genes, without incurring significant side effects. In addition, the use of Vegfa-specific Cas9 RNP did not generate side effects even 7 days after treatment whereas side effects were observed 3 days after treatment in conventional Vegfa-target therapies.

Herein, some exemplary embodiments of the present invention have been described herein. However, it should be understood by those skilled in the art that these embodiment are provided for illustrative purpose only and should not be construed in any way as limiting the present invention. Rather, it should be understood that various modifications, changes, alterations, and equivalent embodiments can be made without departing from the spirit and scope of the present invention, as defined only by the following claims and equivalents thereof.

What is claimed is:

1. A method of treating an eye disease associated with VEGF-A overexpression, comprising a step of administering a ribonucleoprotein comprising a Cas9 protein, and a VEGF-A gene-specific guide RNA containing a targeting sequence binding specifically to a target site of a VEGF-A gene, to a subject in need of treatment of the eye disease associated with VEGF-A overexpression, wherein the Cas9 protein and the VEGF-A gene-specific guide RNA are preassembled to form the ribonucleoprotein before administration, and the guide RNA is hybridizable with a nucleic acid sequence of SEQ ID NO: 1 or 2 in a VEGF-A gene.

2. The method of claim 1, wherein the guide RNA comprises a nucleic acid sequence of SEQ ID NO: 9 or 10.

3. The method of claim 1, wherein the eye disease associated with VEGF-A overexpression is macular degeneration or retinopathy.

\* \* \* \* \*

SEQUENCE LISTING

<160> NUMBER OF SEQ ID NOS: 390

<210> SEQ ID NO 1
<211> LENGTH: 20
<212> TYPE: DNA
<213> ORGANISM: Artificial Sequence
<220> FEATURE:
<223> OTHER INFORMATION: Synthetic(Vegfa-1 target sequence of VEGF-A gene)

<400> SEQUENCE: 1
ctcctggaag atgtccacca            20

```
<210> SEQ ID NO 2
<211> LENGTH: 20
<212> TYPE: DNA
<213> ORGANISM: Artificial Sequence
<220> FEATURE:
<223> OTHER INFORMATION: Synthetic(Vegfa-2 target sequence of VEGF-A
      gene)

<400> SEQUENCE: 2
agctcatctc tcctatgtgc                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic(Vegfa-3 target sequence of VEGF-A
      gene)

<400> SEQUENCE: 3
gaccctggtg gacatcttcc                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic(Vegfa-4 target sequence of VEGF-A
      gene)

<400> SEQUENCE: 4
actcctggaa gatgtccacc                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic(Vegfa-5 target sequence of VEGF-A
      gene)

<400> SEQUENCE: 5
cgcttacctt ggcatggtgg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic(Vegfa-6 target sequence of VEGF-A
      gene)

<400> SEQUENCE: 6
gaccgcttac cttggcatgg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic(Vegfa-7 target sequence of VEGF-A
      gene)

<400> SEQUENCE: 7
cacgaccgct taccttggca                                               20

<210> SEQ ID NO 8
```

```
<211> LENGTH: 20
<212> TYPE: DNA
<213> ORGANISM: Artificial Sequence
<220> FEATURE:
<223> OTHER INFORMATION: Synthetic(Vegfa-8 target sequence of VEGF-A
      gene)

<400> SEQUENCE: 8
ggtgcagcct gggaccactg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic(Vegfa-1 targeting sequence)

<400> SEQUENCE: 9
cuccuggaag auguccacca                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic(Vegfa-2 targeting sequence)

<400> SEQUENCE: 10
agcucaucuc uccuaugugc                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic(Vegfa-3 targeting sequence)

<400> SEQUENCE: 11
gacccuggug gacaucuucc                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic(Vegfa-4 targeting sequence)

<400> SEQUENCE: 12
acuccuggaa gauguccacc                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic(Vegfa-5 targeting sequence)

<400> SEQUENCE: 13
cgcuuaccuu ggcauggugg                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic(Vegfa-6 targeting sequence)
```

```
<400> SEQUENCE: 14
gaccgcuuac cuuggcaugg                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic(Vegfa-7 targeting sequence)

<400> SEQUENCE: 15
cacgaccgcu uaccuuggca                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic(Vegfa-8 targeting sequence)

<400> SEQUENCE: 16
ggugcagccu gggaccacug                                               20

<210> SEQ ID NO 17
<211> LENGTH: 66
<212> TYPE: DNA
<213> ORGANISM: Artificial Sequence
<220> FEATURE:
<223> OTHER INFORMATION: Synthetic(In vitro transcription template
      (forward) encoding sgRNA Vegfa-1)

<400> SEQUENCE: 17
gaaattaata cgactcacta tagctcctgg aagatgtcca ccagttttag agctagaaat   60
agcaag                                                              66

<210> SEQ ID NO 18
<211> LENGTH: 66
<212> TYPE: DNA
<213> ORGANISM: Artificial Sequence
<220> FEATURE:
<223> OTHER INFORMATION: Synthetic(In vitro transcription template
      (forward) encoding sgRNA Vegfa-2)

<400> SEQUENCE: 18
gaaattaata cgactcacta tagagctcat ctctcctatg tgcgttttag agctagaaat   60
agcaag                                                              66

<210> SEQ ID NO 19
<211> LENGTH: 66
<212> TYPE: DNA
<213> ORGANISM: Artificial Sequence
<220> FEATURE:
<223> OTHER INFORMATION: Synthetic(In vitro transcription template
      (forward) encoding sgRNA Vegfa-3)

<400> SEQUENCE: 19
gaaattaata cgactcacta taggaccctg gtggacatct tccgttttag agctagaaat   60
agcaag                                                              66

<210> SEQ ID NO 20
<211> LENGTH: 66
<212> TYPE: DNA
<213> ORGANISM: Artificial Sequence
<220> FEATURE:
```

<223> OTHER INFORMATION: Synthetic(In vitro transcription template
      (forward) encoding sgRNA Vegfa-4)

<400> SEQUENCE: 20
gaaattaata cgactcacta gagctcctg gaagatgtcc accgttttag agctagaaat    60
agcaag                                                              66

<210> SEQ ID NO 21
<211> LENGTH: 66
<212> TYPE: DNA
<213> ORGANISM: Artificial Sequence
<220> FEATURE:
<223> OTHER INFORMATION: Synthetic(In vitro transcription template
      (forward) encoding sgRNA Rosa26)

<400> SEQUENCE: 21
gaaattaata cgactcacta ggcggtc ctcagaagcc agggttttag agctagaaat    60
agcaag                                                              66

<210> SEQ ID NO 22
<211> LENGTH: 82
<212> TYPE: DNA
<213> ORGANISM: Artificial Sequence
<220> FEATURE:
<223> OTHER INFORMATION: Synthetic(In vitro transcription template
      (reverse) encoding sgRNA (universal))

<400> SEQUENCE: 22
aaaaaagcac cgactcggtg ccacttttc aagttgataa cggactagcc ttattttaac    60
ttgctatttc tagctctaaa ac                                            82

<210> SEQ ID NO 23
<211> LENGTH: 20
<212> TYPE: DNA
<213> ORGANISM: Artificial Sequence
<220> FEATURE:
<223> OTHER INFORMATION: Synthetic(Forward primer used for the T7E1
      assay (mouse Vegfa-1, 1st PCR))

<400> SEQUENCE: 23
caaatctggg tggcgataga                                               20

<210> SEQ ID NO 24
<211> LENGTH: 21
<212> TYPE: DNA
<213> ORGANISM: Artificial Sequence
<220> FEATURE:
<223> OTHER INFORMATION: Synthetic(Reverse primer used for the T7E1
      assay (mouse Vegfa-1, 1st PCR))

<400> SEQUENCE: 24
agatggtcaa atcgtggaga g                                             21

<210> SEQ ID NO 25
<211> LENGTH: 53
<212> TYPE: DNA
<213> ORGANISM: Artificial Sequence
<220> FEATURE:
<223> OTHER INFORMATION: Synthetic(Forward primer used for the T7E1
      assay (mouse Vegfa-1, 2nd PCR))

<400> SEQUENCE: 25
acactctttc cctacacgac gctcttccga tctcaaatct gggtggcgat aga          53

```
<210> SEQ ID NO 26
<211> LENGTH: 53
<212> TYPE: DNA
<213> ORGANISM: Artificial Sequence
<220> FEATURE:
<223> OTHER INFORMATION: Synthetic(Reverse primer used for the T7E1
      assay (mouse Vegfa-1, 2nd PCR))

<400> SEQUENCE: 26
gtgactggag ttcagacgtg tgctcttccg atctccaggg cttcatcgtt aca         53

<210> SEQ ID NO 27
<211> LENGTH: 23
<212> TYPE: DNA
<213> ORGANISM: Artificial Sequence
<220> FEATURE:
<223> OTHER INFORMATION: Synthetic(Forward primer used for the T7E1
      assay (human Vegfa-1, 1st PCR))

<400> SEQUENCE: 27
catcgtgtga tctctggaat gaa                                          23

<210> SEQ ID NO 28
<211> LENGTH: 21
<212> TYPE: DNA
<213> ORGANISM: Artificial Sequence
<220> FEATURE:
<223> OTHER INFORMATION: Synthetic(Reverse primer used for the T7E1
      assay (human Vegfa-1, 1st PCR))

<400> SEQUENCE: 28
ccacctgttc ccaaagtgtt a                                            21

<210> SEQ ID NO 29
<211> LENGTH: 56
<212> TYPE: DNA
<213> ORGANISM: Artificial Sequence
<220> FEATURE:
<223> OTHER INFORMATION: Synthetic(Forward primer used for the T7E1
      assay (human Vegfa-1, 2nd PCR))

<400> SEQUENCE: 29
acactctttc cctacacgac gctcttccga tctgtggtga agttcatgga tgtcta      56

<210> SEQ ID NO 30
<211> LENGTH: 52
<212> TYPE: DNA
<213> ORGANISM: Artificial Sequence
<220> FEATURE:
<223> OTHER INFORMATION: Synthetic(Reverse primer used for the T7E1
      assay (human Vegfa-1, 2nd PCR))

<400> SEQUENCE: 30
gtgactggag ttcagacgtg tgctcttccg atctaaagat gcccacctgc at          52

<210> SEQ ID NO 31
<211> LENGTH: 21
<212> TYPE: DNA
<213> ORGANISM: Artificial Sequence
<220> FEATURE:
<223> OTHER INFORMATION: Synthetic(Forward primer used for targeted deep
      sequencing (mouse Vegfa-2, 1st PCR))

<400> SEQUENCE: 31
acctatccct gctcagtaga a                                            21

<210> SEQ ID NO 32
```

```
<211> LENGTH: 20
<212> TYPE: DNA
<213> ORGANISM: Artificial Sequence
<220> FEATURE:
<223> OTHER INFORMATION: Synthetic(Reverse primer used for targeted deep
      sequencing (mouse Vegfa-2, 1st PCR))

<400> SEQUENCE: 32
cccaagagag gaagcaagaa                                                       20

<210> SEQ ID NO 33
<211> LENGTH: 52
<212> TYPE: DNA
<213> ORGANISM: Artificial Sequence
<220> FEATURE:
<223> OTHER INFORMATION: Synthetic(Forward primer used for targeted deep
      sequencing (mouse Vegfa-2, 2nd PCR))

<400> SEQUENCE: 33
acactctttc cctacacgac gctcttccga tctatctgct ccctccctct ac                   52

<210> SEQ ID NO 34
<211> LENGTH: 58
<212> TYPE: DNA
<213> ORGANISM: Artificial Sequence
<220> FEATURE:
<223> OTHER INFORMATION: Synthetic(Reverse primer used for targeted deep
      sequencing (mouse Vegfa-2, 2nd PCR))

<400> SEQUENCE: 34
gtgactggag ttcagacgtg tgctcttccg atctgtccat caccatcacc accaccac            58

<210> SEQ ID NO 35
<211> LENGTH: 20
<212> TYPE: DNA
<213> ORGANISM: Artificial Sequence
<220> FEATURE:
<223> OTHER INFORMATION: Synthetic(Forward primer used for targeted deep
      sequencing (mouse rosa26, 1st PCR))

<400> SEQUENCE: 35
ccaaagtcgc tctgagttgt                                                       20

<210> SEQ ID NO 36
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing (mouse rosa26, 1st PCR))

<400> SEQUENCE: 36
tcgggtgagc atgtctttaa tc                                                    22

<210> SEQ ID NO 37
<211> LENGTH: 53
<212> TYPE: DNA
<213> ORGANISM: Artificial Sequence
<220> FEATURE:
<223> OTHER INFORMATION: Synthetic(Forward primer used for targeted deep
      sequencing (mouse rosa26, 2nd PCR))

<400> SEQUENCE: 37
acactctttc cctacacgac gctcttccga tctccaaagt cgctctgagt tgt                  53

<210> SEQ ID NO 38
<211> LENGTH: 54
```

```
<212> TYPE: DNA
<213> ORGANISM: Artificial Sequence
<220> FEATURE:
<223> OTHER INFORMATION: Synthetic(Reverse primer used for targeted deep
      sequencing (mouse rosa26, 2nd PCR))

<400> SEQUENCE: 38
gtgactggag ttcagacgtg tgctcttccg atctctttaa gcctgcccag aaga          54

<210> SEQ ID NO 39
<211> LENGTH: 22
<212> TYPE: DNA
<213> ORGANISM: Artificial Sequence
<220> FEATURE:
<223> OTHER INFORMATION: Synthetic(Forward primer used for targeted deep
      sequencing (OT1, 1st PCR))

<400> SEQUENCE: 39
tctgtctgtc tccagacatt tg                                             22

<210> SEQ ID NO 40
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing (OT1, 1st PCR))

<400> SEQUENCE: 40
gtcctgcttc tatcctgctt ta                                             22

<210> SEQ ID NO 41
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing (OT1, 2nd PCR))

<400> SEQUENCE: 41
acactctttc cctacacgac gctcttccga tctgtgatca gctgacttcc agttc         55

<210> SEQ ID NO 42
<211> LENGTH: 57
<212> TYPE: DNA
<213> ORGANISM: Artificial Sequence
<220> FEATURE:
<223> OTHER INFORMATION: Synthetic(Reverse primer used for targeted deep
      sequencing (OT1, 2nd PCR))

<400> SEQUENCE: 42
gtgactggag ttcagacgtg tgctcttccg atctctccac aactcaagtc ccattac       57

<210> SEQ ID NO 43
<211> LENGTH: 22
<212> TYPE: DNA
<213> ORGANISM: Artificial Sequence
<220> FEATURE:
<223> OTHER INFORMATION: Synthetic(Forward primer used for targeted deep
      sequencing (OT2, 1st PCR))

<400> SEQUENCE: 43
gacgtgagag tgagcagttt at                                             22

<210> SEQ ID NO 44
<211> LENGTH: 20
<212> TYPE: DNA
```

<213> ORGANISM: Artificial Sequence
<220> FEATURE:
<223> OTHER INFORMATION: Synthetic(Reverse primer used for targeted deep sequencing (OT2, 1st PCR))

<400> SEQUENCE: 44
acagcaccca gattgtcttc                                                    20

<210> SEQ ID NO 45
<211> LENGTH: 54
<212> TYPE: DNA
<213> ORGANISM: Artificial Sequence
<220> FEATURE:
<223> OTHER INFORMATION: Synthetic(Forward primer used for targeted deep sequencing (OT2, 2nd PCR))

<400> SEQUENCE: 45
acactctttc cctacacgac gctcttccga tctccttgtg tcctttgatg ctct             54

<210> SEQ ID NO 46
<211> LENGTH: 54
<212> TYPE: DNA
<213> ORGANISM: Artificial Sequence
<220> FEATURE:
<223> OTHER INFORMATION: Synthetic(Reverse primer used for targeted deep sequencing (OT2, 2nd PCR))

<400> SEQUENCE: 46
gtgactggag ttcagacgtg tgctcttccg atctaaggtc tgcaccatga atcc             54

<210> SEQ ID NO 47
<211> LENGTH: 20
<212> TYPE: DNA
<213> ORGANISM: Artificial Sequence
<220> FEATURE:
<223> OTHER INFORMATION: Synthetic(Forward primer used for targeted deep sequencing (OT3, 1st PCR))

<400> SEQUENCE: 47
gctgtgctca agaccaacaa                                                    20

<210> SEQ ID NO 48
<211> LENGTH: 20
<212> TYPE: DNA
<213> ORGANISM: Artificial Sequence
<220> FEATURE:
<223> OTHER INFORMATION: Synthetic(Reverse primer used for targeted deep sequencing (OT3, 1st PCR))

<400> SEQUENCE: 48
ccggttctgt actggtgtct                                                    20

<210> SEQ ID NO 49
<211> LENGTH: 52
<212> TYPE: DNA
<213> ORGANISM: Artificial Sequence
<220> FEATURE:
<223> OTHER INFORMATION: Synthetic(Forward primer used for targeted deep sequencing (OT3, 2nd PCR))

<400> SEQUENCE: 49
acactctttc cctacacgac gctcttccga tctttgccta cctccacctt ct               52

<210> SEQ ID NO 50
<211> LENGTH: 54
<212> TYPE: DNA
<213> ORGANISM: Artificial Sequence

```
<220> FEATURE:
<223> OTHER INFORMATION: Synthetic(Reverse primer used for targeted deep
      sequencing (OT3, 2nd PCR))

<400> SEQUENCE: 50
gtgactggag ttcagacgtg tgctcttccg atctagatgc tgccctacat gaac              54

<210> SEQ ID NO 51
<211> LENGTH: 21
<212> TYPE: DNA
<213> ORGANISM: Artificial Sequence
<220> FEATURE:
<223> OTHER INFORMATION: Synthetic(Forward primer used for targeted deep
      sequencing (OT4, 1st PCR))

<400> SEQUENCE: 51
gtaggctcaa cagctctttc t                                                  21

<210> SEQ ID NO 52
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing (OT4, 1st PCR))

<400> SEQUENCE: 52
catagtgtga gtggtactgg tg                                                 22

<210> SEQ ID NO 53
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing (OT4, 2nd PCR))

<400> SEQUENCE: 53
acactctttc cctacacgac gctcttccga tctcctgagc ttcctctgtc ctaat             55

<210> SEQ ID NO 54
<211> LENGTH: 55
<212> TYPE: DNA
<213> ORGANISM: Artificial Sequence
<220> FEATURE:
<223> OTHER INFORMATION: Synthetic(Reverse primer used for targeted deep
      sequencing (OT4, 2nd PCR))

<400> SEQUENCE: 54
gtgactggag ttcagacgtg tgctcttccg atctgccact gcttctcctc tctat             55

<210> SEQ ID NO 55
<211> LENGTH: 21
<212> TYPE: DNA
<213> ORGANISM: Artificial Sequence
<220> FEATURE:
<223> OTHER INFORMATION: Synthetic(Forward primer used for targeted deep
      sequencing (OT5, 1st PCR))

<400> SEQUENCE: 55
gcccaaagta gcaggtgatt a                                                  21

<210> SEQ ID NO 56
<211> LENGTH: 23
<212> TYPE: DNA
<213> ORGANISM: Artificial Sequence
<220> FEATURE:
```

<223> OTHER INFORMATION: Synthetic(Reverse primer used for targeted deep
      sequencing (OT5, 1st PCR))

<400> SEQUENCE: 56
ctcaggctgt aactgacgat atg                                              23

<210> SEQ ID NO 57
<211> LENGTH: 53
<212> TYPE: DNA
<213> ORGANISM: Artificial Sequence
<220> FEATURE:
<223> OTHER INFORMATION: Synthetic(Forward primer used for targeted deep
      sequencing (OT5, 2nd PCR))

<400> SEQUENCE: 57
acactctttc cctacacgac gctcttccga tctacaggat gcaagtccac atc             53

<210> SEQ ID NO 58
<211> LENGTH: 54
<212> TYPE: DNA
<213> ORGANISM: Artificial Sequence
<220> FEATURE:
<223> OTHER INFORMATION: Synthetic(Reverse primer used for targeted deep
      sequencing (OT5, 2nd PCR))

<400> SEQUENCE: 58
gtgactggag ttcagacgtg tgctcttccg atctcattct tcacagggcc atca            54

<210> SEQ ID NO 59
<211> LENGTH: 21
<212> TYPE: DNA
<213> ORGANISM: Artificial Sequence
<220> FEATURE:
<223> OTHER INFORMATION: Synthetic(Forward primer used for targeted deep
      sequencing (OT6, 1st PCR))

<400> SEQUENCE: 59
agaagctaag gagcccaatt t                                                21

<210> SEQ ID NO 60
<211> LENGTH: 19
<212> TYPE: DNA
<213> ORGANISM: Artificial Sequence
<220> FEATURE:
<223> OTHER INFORMATION: Synthetic(Reverse primer used for targeted deep
      sequencing (OT6, 1st PCR))

<400> SEQUENCE: 60
tactttgcca agcccatgt                                                   19

<210> SEQ ID NO 61
<211> LENGTH: 53
<212> TYPE: DNA
<213> ORGANISM: Artificial Sequence
<220> FEATURE:
<223> OTHER INFORMATION: Synthetic(Forward primer used for targeted deep
      sequencing (OT6, 2nd PCR))

<400> SEQUENCE: 61
acactctttc cctacacgac gctcttccga tctgccttct ctcttggctg taa             53

<210> SEQ ID NO 62
<211> LENGTH: 56
<212> TYPE: DNA
<213> ORGANISM: Artificial Sequence
<220> FEATURE:
<223> OTHER INFORMATION: Synthetic(Reverse primer used for targeted deep sequencing (OT6, 2nd PCR))

<400> SEQUENCE: 62
gtgactggag ttcagacgtg tgctcttccg atctgaacct actctcatcg tgctac         56

<210> SEQ ID NO 63
<211> LENGTH: 22
<212> TYPE: DNA
<213> ORGANISM: Artificial Sequence
<220> FEATURE:
<223> OTHER INFORMATION: Synthetic(Forward primer used for targeted deep
      sequencing (OT7, 1st PCR))

<400> SEQUENCE: 63
gaggagccca agtatatcac ag                                              22

<210> SEQ ID NO 64
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing (OT7, 1st PCR))

<400> SEQUENCE: 64
ggtcaccata gctacaagag ag                                              22

<210> SEQ ID NO 65
<211> LENGTH: 53
<212> TYPE: DNA
<213> ORGANISM: Artificial Sequence
<220> FEATURE:
<223> OTHER INFORMATION: Synthetic(Forward primer used for targeted deep
      sequencing (OT7, 2nd PCR))

<400> SEQUENCE: 65
acactctttc cctacacgac gctcttccga tctaaggctc cattagcctc ttc            53

<210> SEQ ID NO 66
<211> LENGTH: 55
<212> TYPE: DNA
<213> ORGANISM: Artificial Sequence
<220> FEATURE:
<223> OTHER INFORMATION: Synthetic(Reverse primer used for targeted deep
      sequencing (OT7, 2nd PCR))

<400> SEQUENCE: 66
gtgactggag ttcagacgtg tgctcttccg atctctgtca tggtgcacat cattc          55

<210> SEQ ID NO 67
<211> LENGTH: 20
<212> TYPE: DNA
<213> ORGANISM: Artificial Sequence
<220> FEATURE:
<223> OTHER INFORMATION: Synthetic(Forward primer used for targeted deep
      sequencing (OT8, 1st PCR))

<400> SEQUENCE: 67
ccctgcagca ttctctgtat                                                 20

<210> SEQ ID NO 68
<211> LENGTH: 21
<212> TYPE: DNA
<213> ORGANISM: Artificial Sequence
<220> FEATURE:
<223> OTHER INFORMATION: Synthetic(Reverse primer used for targeted deep
      sequencing (OT8, 1st PCR))

<400> SEQUENCE: 68
gacccagtgt attgtgggta g                                             21

<210> SEQ ID NO 69
<211> LENGTH: 54
<212> TYPE: DNA
<213> ORGANISM: Artificial Sequence
<220> FEATURE:
<223> OTHER INFORMATION: Synthetic(Forward primer used for targeted deep
      sequencing (OT8, 2nd PCR))

<400> SEQUENCE: 69
acactctttc cctacacgac gctcttccga tcttgacaag cctgacagtt catc          54

<210> SEQ ID NO 70
<211> LENGTH: 53
<212> TYPE: DNA
<213> ORGANISM: Artificial Sequence
<220> FEATURE:
<223> OTHER INFORMATION: Synthetic(Reverse primer used for targeted deep
      sequencing (OT8, 2nd PCR))

<400> SEQUENCE: 70
gtgactggag ttcagacgtg tgctcttccg atctggctga tggtgagcag aaa           53

<210> SEQ ID NO 71
<211> LENGTH: 25
<212> TYPE: DNA
<213> ORGANISM: Artificial Sequence
<220> FEATURE:
<223> OTHER INFORMATION: Synthetic(Forward primer used for targeted deep
      sequencing (OT9, 1st PCR))

<400> SEQUENCE: 71
ctggaaccag agtcatagat agttg                                         25

<210> SEQ ID NO 72
<211> LENGTH: 20
<212> TYPE: DNA
<213> ORGANISM: Artificial Sequence
<220> FEATURE:
<223> OTHER INFORMATION: Synthetic(Reverse primer used for targeted deep
      sequencing (OT9, 1st PCR))

<400> SEQUENCE: 72
tctgaagcac acaccagaag                                               20

<210> SEQ ID NO 73
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing (OT9, 2nd PCR))

<400> SEQUENCE: 73
acactctttc cctacacgac gctcttccga tctcaagata ccaaagcagg tgttc         55

<210> SEQ ID NO 74
<211> LENGTH: 56
<212> TYPE: DNA
<213> ORGANISM: Artificial Sequence
<220> FEATURE:
<223> OTHER INFORMATION: Synthetic(Reverse primer used for targeted deep
      sequencing (OT9, 2nd PCR))

<400> SEQUENCE: 74
gtgactggag ttcagacgtg tgctcttccg atctgaagca gttcagaggt ctatgt    56

<210> SEQ ID NO 75
<211> LENGTH: 22
<212> TYPE: DNA
<213> ORGANISM: Artificial Sequence
<220> FEATURE:
<223> OTHER INFORMATION: Synthetic(Forward primer used for targeted deep
      sequencing (OT10, 1st PCR))

<400> SEQUENCE: 75
ctagaagaag gcagagggag ta    22

<210> SEQ ID NO 76
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing (OT10, 1st PCR))

<400> SEQUENCE: 76
aggagggaca gactggtata aa    22

<210> SEQ ID NO 77
<211> LENGTH: 52
<212> TYPE: DNA
<213> ORGANISM: Artificial Sequence
<220> FEATURE:
<223> OTHER INFORMATION: Synthetic(Forward primer used for targeted deep
      sequencing (OT10, 2nd PCR))

<400> SEQUENCE: 77
acactctttc cctacacgac gctcttccga tctcacagcg agccagaata ca    52

<210> SEQ ID NO 78
<211> LENGTH: 57
<212> TYPE: DNA
<213> ORGANISM: Artificial Sequence
<220> FEATURE:
<223> OTHER INFORMATION: Synthetic(Reverse primer used for targeted deep
      sequencing (OT10, 2nd PCR))

<400> SEQUENCE: 78
gtgactggag ttcagacgtg tgctcttccg atctctgtgc tacctgatct actcaac    57

<210> SEQ ID NO 79
<211> LENGTH: 21
<212> TYPE: DNA
<213> ORGANISM: Artificial Sequence
<220> FEATURE:
<223> OTHER INFORMATION: Synthetic(Forward primer used for targeted deep
      sequencing (OT11, 1st PCR))

<400> SEQUENCE: 79
gtgtgaatgg aggcgaaatt g    21

<210> SEQ ID NO 80
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing (OT11, 1st PCR))

<400> SEQUENCE: 80
gcagctgaga agctaaggaa ta        22

<210> SEQ ID NO 81
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing (OT11, 2nd PCR))

<400> SEQUENCE: 81
acactctttc cctacacgac gctcttccga tcttacataa agtccctgca acctg        55

<210> SEQ ID NO 82
<211> LENGTH: 56
<212> TYPE: DNA
<213> ORGANISM: Artificial Sequence
<220> FEATURE:
<223> OTHER INFORMATION: Synthetic(Reverse primer used for targeted deep
      sequencing (OT11, 2nd PCR))

<400> SEQUENCE: 82
gtgactggag ttcagacgtg tgctcttccg atctttacca ggactctagt gagtgg        56

<210> SEQ ID NO 83
<211> LENGTH: 21
<212> TYPE: DNA
<213> ORGANISM: Artificial Sequence
<220> FEATURE:
<223> OTHER INFORMATION: Synthetic(Forward primer used for targeted deep
      sequencing (OT12, 1st PCR))

<400> SEQUENCE: 83
tagtacctgc ccaccagata g        21

<210> SEQ ID NO 84
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing (OT12, 1st PCR))

<400> SEQUENCE: 84
gggcacttct tcaatgcttt ac        22

<210> SEQ ID NO 85
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing (OT12, 2nd PCR))

<400> SEQUENCE: 85
acactctttc cctacacgac gctcttccga tctctcctga ccagtgttct gtaat        55

<210> SEQ ID NO 86
<211> LENGTH: 54
<212> TYPE: DNA
<213> ORGANISM: Artificial Sequence
<220> FEATURE:
<223> OTHER INFORMATION: Synthetic(Reverse primer used for targeted deep
      sequencing (OT12, 2nd PCR))

<400> SEQUENCE: 86
gtgactggag ttcagacgtg tgctcttccg atctaaacct cgagtaggaa ggga    54

<210> SEQ ID NO 87
<211> LENGTH: 22
<212> TYPE: DNA
<213> ORGANISM: Artificial Sequence
<220> FEATURE:
<223> OTHER INFORMATION: Synthetic(Forward primer used for targeted deep
      sequencing (OT13, 1st PCR))

<400> SEQUENCE: 87
cccactgagg ttgtatcagt tc    22

<210> SEQ ID NO 88
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing (OT13, 1st PCR))

<400> SEQUENCE: 88
gatccaatgg ctttgcacat ac    22

<210> SEQ ID NO 89
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing (OT13, 2nd PCR))

<400> SEQUENCE: 89
acactctttc cctacacgac gctcttccga tctaaagaag accagtgaag gactg    55

<210> SEQ ID NO 90
<211> LENGTH: 55
<212> TYPE: DNA
<213> ORGANISM: Artificial Sequence
<220> FEATURE:
<223> OTHER INFORMATION: Synthetic(Reverse primer used for targeted deep
      sequencing (OT13, 2nd PCR))

<400> SEQUENCE: 90
gtgactggag ttcagacgtg tgctcttccg atctagtctg atgacccgag ttcta    55

<210> SEQ ID NO 91
<211> LENGTH: 25
<212> TYPE: DNA
<213> ORGANISM: Artificial Sequence
<220> FEATURE:
<223> OTHER INFORMATION: Synthetic(Forward primer used for targeted deep
      sequencing (OT14, 1st PCR))

<400> SEQUENCE: 91
tctatatagg caggttatga aagca    25

<210> SEQ ID NO 92
<211> LENGTH: 23
<212> TYPE: DNA
<213> ORGANISM: Artificial Sequence
<220> FEATURE:
<223> OTHER INFORMATION: Synthetic(Reverse primer used for targeted deep
      sequencing (OT14, 1st PCR))

<400> SEQUENCE: 92
aaccaggaca tatgtggtag aaa    23

```
<210> SEQ ID NO 93
<211> LENGTH: 52
<212> TYPE: DNA
<213> ORGANISM: Artificial Sequence
<220> FEATURE:
<223> OTHER INFORMATION: Synthetic(Forward primer used for targeted deep
      sequencing (OT14, 2nd PCR))

<400> SEQUENCE: 93
acactctttc cctacacgac gctcttccga tctaatggcc ttctgggaaa gt            52

<210> SEQ ID NO 94
<211> LENGTH: 56
<212> TYPE: DNA
<213> ORGANISM: Artificial Sequence
<220> FEATURE:
<223> OTHER INFORMATION: Synthetic(Reverse primer used for targeted deep
      sequencing (OT14, 2nd PCR))

<400> SEQUENCE: 94
gtgactggag ttcagacgtg tgctcttccg atctctgagt ctgagagctt gtagtg        56

<210> SEQ ID NO 95
<211> LENGTH: 20
<212> TYPE: DNA
<213> ORGANISM: Artificial Sequence
<220> FEATURE:
<223> OTHER INFORMATION: Synthetic(Forward primer used for targeted deep
      sequencing (OT15, 1st PCR))

<400> SEQUENCE: 95
cacagacagt cgccttcaat                                                20

<210> SEQ ID NO 96
<211> LENGTH: 23
<212> TYPE: DNA
<213> ORGANISM: Artificial Sequence
<220> FEATURE:
<223> OTHER INFORMATION: Synthetic(Reverse primer used for targeted deep
      sequencing (OT15, 1st PCR))

<400> SEQUENCE: 96
tggaagcctt aacaggtcaa taa                                            23

<210> SEQ ID NO 97
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing (OT15, 2nd PCR))

<400> SEQUENCE: 97
acactctttc cctacacgac gctcttccga tctgccttca atgaatctcc ctttg         55

<210> SEQ ID NO 98
<211> LENGTH: 54
<212> TYPE: DNA
<213> ORGANISM: Artificial Sequence
<220> FEATURE:
<223> OTHER INFORMATION: Synthetic(Reverse primer used for targeted deep
      sequencing (OT15, 2nd PCR))

<400> SEQUENCE: 98
gtgactggag ttcagacgtg tgctcttccg atctgcttca ttggcagcac ttac          54
```

```
<210> SEQ ID NO 99
<211> LENGTH: 23
<212> TYPE: DNA
<213> ORGANISM: Artificial Sequence
<220> FEATURE:
<223> OTHER INFORMATION: Synthetic(Forward primer used for targeted deep
      sequencing (OT16, 1st PCR))

<400> SEQUENCE: 99
ggaagatcag cagtctcaac taa                                              23

<210> SEQ ID NO 100
<211> LENGTH: 24
<212> TYPE: DNA
<213> ORGANISM: Artificial Sequence
<220> FEATURE:
<223> OTHER INFORMATION: Synthetic(Reverse primer used for targeted deep
      sequencing (OT16, 1st PCR))

<400> SEQUENCE: 100
cacattacct caaagctgtt tctt                                             24

<210> SEQ ID NO 101
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing (OT16, 2nd PCR))

<400> SEQUENCE: 101
acactctttc cctacacgac gctcttccga tctctcagtg acagagactc accta           55

<210> SEQ ID NO 102
<211> LENGTH: 55
<212> TYPE: DNA
<213> ORGANISM: Artificial Sequence
<220> FEATURE:
<223> OTHER INFORMATION: Synthetic(Reverse primer used for targeted deep
      sequencing (OT16, 2nd PCR))

<400> SEQUENCE: 102
gtgactggag ttcagacgtg tgctcttccg atctgtggtg acatggctgt atctt           55

<210> SEQ ID NO 103
<211> LENGTH: 22
<212> TYPE: DNA
<213> ORGANISM: Artificial Sequence
<220> FEATURE:
<223> OTHER INFORMATION: Synthetic(Forward primer used for targeted deep
      sequencing (OT17, 1st PCR))

<400> SEQUENCE: 103
cttccaccgg gtatttccta tc                                               22

<210> SEQ ID NO 104
<211> LENGTH: 23
<212> TYPE: DNA
<213> ORGANISM: Artificial Sequence
<220> FEATURE:
<223> OTHER INFORMATION: Synthetic(Reverse primer used for targeted deep
      sequencing (OT17, 1st PCR))

<400> SEQUENCE: 104
tcccagagag agttaggtta aga                                              23
```

```
<210> SEQ ID NO 105
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing (OT17, 2nd PCR))

<400> SEQUENCE: 105
acactctttc cctacacgac gctcttccga tctagatgaa tgagcaccag agaaa          55

<210> SEQ ID NO 106
<211> LENGTH: 56
<212> TYPE: DNA
<213> ORGANISM: Artificial Sequence
<220> FEATURE:
<223> OTHER INFORMATION: Synthetic(Reverse primer used for targeted deep
      sequencing (OT17, 2nd PCR))

<400> SEQUENCE: 106
gtgactggag ttcagacgtg tgctcttccg atctagacaa gaaagggcag taagaa         56

<210> SEQ ID NO 107
<211> LENGTH: 20
<212> TYPE: DNA
<213> ORGANISM: Artificial Sequence
<220> FEATURE:
<223> OTHER INFORMATION: Synthetic(Forward primer used for targeted deep
      sequencing (OT18, 1st PCR))

<400> SEQUENCE: 107
cctgggaaca acagccataa                                                 20

<210> SEQ ID NO 108
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing (OT18, 1st PCR))

<400> SEQUENCE: 108
gaacattggg taggtgagga ag                                              22

<210> SEQ ID NO 109
<211> LENGTH: 54
<212> TYPE: DNA
<213> ORGANISM: Artificial Sequence
<220> FEATURE:
<223> OTHER INFORMATION: Synthetic(Forward primer used for targeted deep
      sequencing (OT18, 2nd PCR))

<400> SEQUENCE: 109
acactctttc cctacacgac gctcttccga tcttctctgt tgaggtggga tttg           54

<210> SEQ ID NO 110
<211> LENGTH: 54
<212> TYPE: DNA
<213> ORGANISM: Artificial Sequence
<220> FEATURE:
<223> OTHER INFORMATION: Synthetic(Reverse primer used for targeted deep
      sequencing (OT18, 2nd PCR))

<400> SEQUENCE: 110
gtgactggag ttcagacgtg tgctcttccg atctgtactg cttgaggagc ttgt           54

<210> SEQ ID NO 111
```

<211> LENGTH: 20
<212> TYPE: DNA
<213> ORGANISM: Artificial Sequence
<220> FEATURE:
<223> OTHER INFORMATION: Synthetic(Forward primer used for targeted deep
      sequencing (OT19, 1st PCR))

<400> SEQUENCE: 111
tgagccagtc cattcattcc                                          20

<210> SEQ ID NO 112
<211> LENGTH: 21
<212> TYPE: DNA
<213> ORGANISM: Artificial Sequence
<220> FEATURE:
<223> OTHER INFORMATION: Synthetic(Reverse primer used for targeted deep
      sequencing (OT19, 1st PCR))

<400> SEQUENCE: 112
tccctcctgt tcttctcttc t                                        21

<210> SEQ ID NO 113
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing (OT19, 2nd PCR))

<400> SEQUENCE: 113
acactctttc cctacacgac gctcttccga tctttgggac aagtgtacag agaac    55

<210> SEQ ID NO 114
<211> LENGTH: 56
<212> TYPE: DNA
<213> ORGANISM: Artificial Sequence
<220> FEATURE:
<223> OTHER INFORMATION: Synthetic(Reverse primer used for targeted deep
      sequencing (OT19, 2nd PCR))

<400> SEQUENCE: 114
gtgactggag ttcagacgtg tgctcttccg atctaccttc acctacagag aagaga   56

<210> SEQ ID NO 115
<211> LENGTH: 21
<212> TYPE: DNA
<213> ORGANISM: Artificial Sequence
<220> FEATURE:
<223> OTHER INFORMATION: Synthetic(Forward primer used for targeted deep
      sequencing (OT20, 1st PCR))

<400> SEQUENCE: 115
cccacaaacc aagaacaaca a                                        21

<210> SEQ ID NO 116
<211> LENGTH: 23
<212> TYPE: DNA
<213> ORGANISM: Artificial Sequence
<220> FEATURE:
<223> OTHER INFORMATION: Synthetic(Reverse primer used for targeted deep
      sequencing (OT20, 1st PCR))

<400> SEQUENCE: 116
cagtgttaag tgcctctgta gat                                      23

<210> SEQ ID NO 117
<211> LENGTH: 50

<212> TYPE: DNA
<213> ORGANISM: Artificial Sequence
<220> FEATURE:
<223> OTHER INFORMATION: Synthetic(Forward primer used for targeted deep
      sequencing (OT20, 2nd PCR))

<400> SEQUENCE: 117
acactctttc cctacacgac gctcttccga tctcagaagg gcggcatcag                50

<210> SEQ ID NO 118
<211> LENGTH: 55
<212> TYPE: DNA
<213> ORGANISM: Artificial Sequence
<220> FEATURE:
<223> OTHER INFORMATION: Synthetic(Reverse primer used for targeted deep
      sequencing (OT20, 2nd PCR))

<400> SEQUENCE: 118
gtgactggag ttcagacgtg tgctcttccg atcttttagt ctctggtttc cacct          55

<210> SEQ ID NO 119
<211> LENGTH: 20
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT1, 1st PCR))

<400> SEQUENCE: 119
atggagcttg cattttaaca                                                 20

<210> SEQ ID NO 120
<211> LENGTH: 20
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT1, 1st PCR))

<400> SEQUENCE: 120
cttttttccc gtgatcctca                                                 20

<210> SEQ ID NO 121
<211> LENGTH: 53
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT1, 2nd PCR))

<400> SEQUENCE: 121
acactctttc cctacacgac gctcttccga tctatggagc ttgcatttta aca            53

<210> SEQ ID NO 122
<211> LENGTH: 56
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT1, 2nd PCR))

<400> SEQUENCE: 122
gtgactggag ttcagacgtg tgctcttccg atctgctggc ttatttcatc atttag         56

<210> SEQ ID NO 123
<211> LENGTH: 22
<212> TYPE: DNA

<213> ORGANISM: Artificial Sequence
<220> FEATURE:
<223> OTHER INFORMATION: Synthetic(Forward primer used for targeted deep
      sequencing captured by Digenome-seq (OT2, 1st PCR))

<400> SEQUENCE: 123
caaactgtca gtgagccaat ac                                              22

<210> SEQ ID NO 124
<211> LENGTH: 23
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT2, 1st PCR))

<400> SEQUENCE: 124
gaagtgatcc tcctctcaat acc                                             23

<210> SEQ ID NO 125
<211> LENGTH: 53
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT2, 2nd PCR))

<400> SEQUENCE: 125
acactctttc cctacacgac gctcttccga tctcaggaag tcaagcagga aga            53

<210> SEQ ID NO 126
<211> LENGTH: 58
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT2, 2nd PCR))

<400> SEQUENCE: 126
gtgactggag ttcagacgtg tgctcttccg atctcatcca tccattcata actttgga      58

<210> SEQ ID NO 127
<211> LENGTH: 23
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT3, 1st PCR))

<400> SEQUENCE: 127
gtccaatact ctaagcctca gtt                                             23

<210> SEQ ID NO 128
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT3, 1st PCR))

<400> SEQUENCE: 128
accagcacca cactatctat tt                                              22

<210> SEQ ID NO 129
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT3, 2nd PCR))

<400> SEQUENCE: 129
acactctttc cctacacgac gctcttccga tctatascta gtttgtaggg ttgtt         55

<210> SEQ ID NO 130
<211> LENGTH: 59
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT3, 2nd PCR))

<400> SEQUENCE: 130
gtgactggag ttcagacgtg tgctcttccg atctgcacca cactatctat ttctgttat    59

<210> SEQ ID NO 131
<211> LENGTH: 22
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT4, 1st PCR))

<400> SEQUENCE: 131
acactatgat ctttccctgc aa                                             22

<210> SEQ ID NO 132
<211> LENGTH: 24
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT4, 1st PCR))

<400> SEQUENCE: 132
cagaaaccct gaagtcttga attg                                           24

<210> SEQ ID NO 133
<211> LENGTH: 56
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT4, 2nd PCR))

<400> SEQUENCE: 133
acactctttc cctacacgac gctcttccga tcttcttttcc ctgcaaagaa gtaaga       56

<210> SEQ ID NO 134
<211> LENGTH: 56
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT4, 2nd PCR))

<400> SEQUENCE: 134
gtgactggag ttcagacgtg tgctcttccg atctgtctca ttgtccagaa ctgtgt        56

<210> SEQ ID NO 135
<211> LENGTH: 20
<212> TYPE: DNA
<213> ORGANISM: Artificial Sequence
<220> FEATURE:

<223> OTHER INFORMATION: Synthetic(Forward primer used for targeted deep
      sequencing captured by Digenome-seq (OT5, 1st PCR))

<400> SEQUENCE: 135
gggcagaaag gacagaaact                                              20

<210> SEQ ID NO 136
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT5, 1st PCR))

<400> SEQUENCE: 136
ggagaaactg aaaccaggag aa                                           22

<210> SEQ ID NO 137
<211> LENGTH: 53
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT5, 2nd PCR))

<400> SEQUENCE: 137
acactctttc cctacacgac gctcttccga tctcgtaaca gcaccttggt cat          53

<210> SEQ ID NO 138
<211> LENGTH: 57
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT5, 2nd PCR))

<400> SEQUENCE: 138
gtgactggag ttcagacgtg tgctcttccg atctctgaaa ccaggagaag tgtagtc      57

<210> SEQ ID NO 139
<211> LENGTH: 21
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT6, 1st PCR))

<400> SEQUENCE: 139
agtaggtggg agggttctta t                                            21

<210> SEQ ID NO 140
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT6, 1st PCR))

<400> SEQUENCE: 140
caccatctct gtgtctcatc tg                                           22

<210> SEQ ID NO 141
<211> LENGTH: 54
<212> TYPE: DNA
<213> ORGANISM: Artificial Sequence
<220> FEATURE:
<223> OTHER INFORMATION: Synthetic(Forward primer used for targeted deep sequencing captured by Digenome-seq (OT6, 2nd PCR))

<400> SEQUENCE: 141
acactctttc cctacacgac gctcttccga tctagaaaca ggcatctgga gaac            54

<210> SEQ ID NO 142
<211> LENGTH: 55
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT6, 2nd PCR))

<400> SEQUENCE: 142
gtgactggag ttcagacgtg tgctcttccg atctttcagc atagtcttgc tcgtc           55

<210> SEQ ID NO 143
<211> LENGTH: 19
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT7, 1st PCR))

<400> SEQUENCE: 143
taagcctggc ctgtctctt                                                   19

<210> SEQ ID NO 144
<211> LENGTH: 18
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT7, 1st PCR))

<400> SEQUENCE: 144
agagcaggac gtggtgag                                                    18

<210> SEQ ID NO 145
<211> LENGTH: 50
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT7, 2nd PCR))

<400> SEQUENCE: 145
acactctttc cctacacgac gctcttccga tcttctcttc ctgggaccct                 50

<210> SEQ ID NO 146
<211> LENGTH: 56
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT7, 2nd PCR))

<400> SEQUENCE: 146
gtgactggag ttcagacgtg tgctcttccg atctatacct aggaatgcag aacaag          56

<210> SEQ ID NO 147
<211> LENGTH: 22
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT8, 1st PCR))

<210> SEQ ID NO 148
<211> LENGTH: 22
<212> TYPE: DNA
<213> ORGANISM: Artificial Sequence
<220> FEATURE:
<223> OTHER INFORMATION: Synthetic(Reverse primer used for targeted deep sequencing captured by Digenome-seq (OT8, 1st PCR))

<400> SEQUENCE: 148
ctatgcggtc tcttgtgcta at             22

<210> SEQ ID NO 149
<211> LENGTH: 56
<212> TYPE: DNA
<213> ORGANISM: Artificial Sequence
<220> FEATURE:
<223> OTHER INFORMATION: Synthetic(Forward primer used for targeted deep sequencing captured by Digenome-seq (OT8, 2nd PCR))

<400> SEQUENCE: 149
acactctttc cctacacgac gctcttccga tctggtcagg tgggtaatga tttctg      56

<210> SEQ ID NO 150
<211> LENGTH: 60
<212> TYPE: DNA
<213> ORGANISM: Artificial Sequence
<220> FEATURE:
<223> OTHER INFORMATION: Synthetic(Reverse primer used for targeted deep sequencing captured by Digenome-seq (OT8, 2nd PCR))

<400> SEQUENCE: 150
gtgactggag ttcagacgtg tgctcttccg atctctaatc tgccttatgt aatgggttct   60

<210> SEQ ID NO 151
<211> LENGTH: 20
<212> TYPE: DNA
<213> ORGANISM: Artificial Sequence
<220> FEATURE:
<223> OTHER INFORMATION: Synthetic(Forward primer used for targeted deep sequencing captured by Digenome-seq (OT9, 1st PCR))

<400> SEQUENCE: 151
gactcctctg tggaaagagc           20

<210> SEQ ID NO 152
<211> LENGTH: 20
<212> TYPE: DNA
<213> ORGANISM: Artificial Sequence
<220> FEATURE:
<223> OTHER INFORMATION: Synthetic(Reverse primer used for targeted deep sequencing captured by Digenome-seq (OT9, 1st PCR))

<400> SEQUENCE: 152
aggactccag tgctgagcac           20

<210> SEQ ID NO 153
<211> LENGTH: 52
<212> TYPE: DNA
<213> ORGANISM: Artificial Sequence
<220> FEATURE:
<223> OTHER INFORMATION: Synthetic(Forward primer used for targeted deep sequencing captured by Digenome-seq (OT9, 2nd PCR))

<400> SEQUENCE: 153
acactctttc cctacacgac gctcttccga tcttcctctg tggaaagagc ct    52

<210> SEQ ID NO 154
<211> LENGTH: 54
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT9, 2nd PCR))

<400> SEQUENCE: 154
gtgactggag ttcagacgtg tgctcttccg atctacaccg tctctccttt gtgc    54

<210> SEQ ID NO 155
<211> LENGTH: 26
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT10, 1st PCR))

<400> SEQUENCE: 155
agggaccgta tcagatattg ttaatc    26

<210> SEQ ID NO 156
<211> LENGTH: 21
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT10, 1st PCR))

<400> SEQUENCE: 156
tccaatgtat tgcagccatc t    21

<210> SEQ ID NO 157
<211> LENGTH: 57
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT10, 2nd PCR))

<400> SEQUENCE: 157
acactctttc cctacacgac gctcttccga tctaatcaat ccttgtgcag cttaatg    57

<210> SEQ ID NO 158
<211> LENGTH: 53
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT10, 2nd PCR))

<400> SEQUENCE: 158
gtgactggag ttcagacgtg tgctcttccg atctcagcca tcttgccctt tga    53

<210> SEQ ID NO 159
<211> LENGTH: 23
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT11, 1st PCR))

<400> SEQUENCE: 159

```
cattgaggaa cctcaccttc tat                                            23
```

<210> SEQ ID NO 160
<211> LENGTH: 23
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT11, 1st PCR))

<400> SEQUENCE: 160

```
atgaatgtct tggtactgtc ctc                                            23
```

<210> SEQ ID NO 161
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT11, 2nd PCR))

<400> SEQUENCE: 161

```
acactctttc cctacacgac gctcttccga tctggaagag gtgtattagg ccatt         55
```

<210> SEQ ID NO 162
<211> LENGTH: 57
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT11, 2nd PCR))

<400> SEQUENCE: 162

```
gtgactggag ttcagacgtg tgctcttccg atctcctctt ctctcttgct tcatctc       57
```

<210> SEQ ID NO 163
<211> LENGTH: 20
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT12, 1st PCR))

<400> SEQUENCE: 163

```
caaagcagct cctcttcctc                                                20
```

<210> SEQ ID NO 164
<211> LENGTH: 20
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT12, 1st PCR))

<400> SEQUENCE: 164

```
cagtgccttt cagtgaacct                                                20
```

<210> SEQ ID NO 165
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT12, 2nd PCR))

<400> SEQUENCE: 165

```
acactctttc cctacacgac gctcttccga tcttctgggt atagagacca tgaca      55
```

<210> SEQ ID NO 166
<211> LENGTH: 59
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT12, 2nd PCR))

<400> SEQUENCE: 166

```
gtgactggag ttcagacgtg tgctcttccg atctcacagc ctgagataat gatagagag    59
```

<210> SEQ ID NO 167
<211> LENGTH: 22
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT13, 1st PCR))

<400> SEQUENCE: 167

```
ggagtcgtac cctggtttat tt                                            22
```

<210> SEQ ID NO 168
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT13, 1st PCR))

<400> SEQUENCE: 168

```
gaagcattgt tccaccttaa cc                                            22
```

<210> SEQ ID NO 169
<211> LENGTH: 58
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT13, 2nd PCR))

<400> SEQUENCE: 169

```
acactctttc cctacacgac gctcttccga tctgggatag aagattaggc agagtatg     58
```

<210> SEQ ID NO 170
<211> LENGTH: 55
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT13, 2nd PCR))

<400> SEQUENCE: 170

```
gtgactggag ttcagacgtg tgctcttccg atcttgcatg tttgaaagga tgagc        55
```

<210> SEQ ID NO 171
<211> LENGTH: 22
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT14, 1st PCR))

<400> SEQUENCE: 171

```
ctctcagacc ctactcacct at                                            22
```

<210> SEQ ID NO 172
<211> LENGTH: 21
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT14, 1st PCR))

<400> SEQUENCE: 172
cactggaagt acctgtggaa g                                            21

<210> SEQ ID NO 173
<211> LENGTH: 57
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT14, 2nd PCR))

<400> SEQUENCE: 173
acactctttc cctacacgac gctcttccga tctagaccct actcacctat atcctttt    57

<210> SEQ ID NO 174
<211> LENGTH: 53
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT14, 2nd PCR))

<400> SEQUENCE: 174
gtgactggag ttcagacgtg tgctcttccg atcttacctg tggaagcagg aga         53

<210> SEQ ID NO 175
<211> LENGTH: 21
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT15, 1st PCR))

<400> SEQUENCE: 175
ggccatcctc aaagacatga a                                            21

<210> SEQ ID NO 176
<211> LENGTH: 19
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT15, 1st PCR))

<400> SEQUENCE: 176
tctcaaactc ccgacctca                                               19

<210> SEQ ID NO 177
<211> LENGTH: 60
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT15, 2nd PCR))

<400> SEQUENCE: 177
acactctttc cctacacgac gctcttccga tctgcatttc tatttattca tctcccacag  60

<210> SEQ ID NO 178
<211> LENGTH: 53
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT15, 2nd PCR))

<400> SEQUENCE: 178
gtgactggag ttcagacgtg tgctcttccg atctctggga ttacaggcgt gag      53

<210> SEQ ID NO 179
<211> LENGTH: 23
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT16, 1st PCR))

<400> SEQUENCE: 179
agaagtttca ggatgacaga tcc                                        23

<210> SEQ ID NO 180
<211> LENGTH: 21
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT16, 1st PCR))

<400> SEQUENCE: 180
caatccacat ctgcgtgttt c                                          21

<210> SEQ ID NO 181
<211> LENGTH: 56
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT16, 2nd PCR))

<400> SEQUENCE: 181
acactctttc cctacacgac gctcttccga tctagaagtt tcaggatgac agatcc    56

<210> SEQ ID NO 182
<211> LENGTH: 55
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT16, 2nd PCR))

<400> SEQUENCE: 182
gtgactggag ttcagacgtg tgctcttccg atctcaatcc acatctgcgt gtttc     55

<210> SEQ ID NO 183
<211> LENGTH: 25
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT17, 1st PCR))

<400> SEQUENCE: 183
tgactcattg tgaatgcctt tattc                                      25

<210> SEQ ID NO 184
<211> LENGTH: 20
<212> TYPE: DNA
<213> ORGANISM: Artificial Sequence
<220> FEATURE:
<223> OTHER INFORMATION: Synthetic(Reverse primer used for targeted deep sequencing captured by Digenome-seq (OT17, 1st PCR))

<400> SEQUENCE: 184
gagttgggtt ctctgcaact                                           20

<210> SEQ ID NO 185
<211> LENGTH: 59
<212> TYPE: DNA
<213> ORGANISM: Artificial Sequence
<220> FEATURE:
<223> OTHER INFORMATION: Synthetic(Forward primer used for targeted deep sequencing captured by Digenome-seq (OT17, 2nd PCR))

<400> SEQUENCE: 185
acactctttc cctacacgac gctcttccga tcttatagag tctagattag cagtagagc     59

<210> SEQ ID NO 186
<211> LENGTH: 59
<212> TYPE: DNA
<213> ORGANISM: Artificial Sequence
<220> FEATURE:
<223> OTHER INFORMATION: Synthetic(Reverse primer used for targeted deep sequencing captured by Digenome-seq (OT17, 2nd PCR))

<400> SEQUENCE: 186
gtgactggag ttcagacgtg tgctcttccg atctaagtct tatctgatac atggatacc     59

<210> SEQ ID NO 187
<211> LENGTH: 18
<212> TYPE: DNA
<213> ORGANISM: Artificial Sequence
<220> FEATURE:
<223> OTHER INFORMATION: Synthetic(Forward primer used for targeted deep sequencing captured by Digenome-seq (OT18, 1st PCR))

<400> SEQUENCE: 187
tgcagctctg gacaggaa                                             18

<210> SEQ ID NO 188
<211> LENGTH: 19
<212> TYPE: DNA
<213> ORGANISM: Artificial Sequence
<220> FEATURE:
<223> OTHER INFORMATION: Synthetic(Reverse primer used for targeted deep sequencing captured by Digenome-seq (OT18, 1st PCR))

<400> SEQUENCE: 188
ggtgggtttc accatcctc                                            19

<210> SEQ ID NO 189
<211> LENGTH: 51
<212> TYPE: DNA
<213> ORGANISM: Artificial Sequence
<220> FEATURE:
<223> OTHER INFORMATION: Synthetic(Forward primer used for targeted deep sequencing captured by Digenome-seq (OT18, 2nd PCR))

<400> SEQUENCE: 189
acactctttc cctacacgac gctcttccga tctgggtgat tccctctgtg g            51

<210> SEQ ID NO 190

<211> LENGTH: 51
<212> TYPE: DNA
<213> ORGANISM: Artificial Sequence
<220> FEATURE:
<223> OTHER INFORMATION: Synthetic(Reverse primer used for targeted deep sequencing captured by Digenome-seq (OT18, 2nd PCR))

<400> SEQUENCE: 190
gtgactggag ttcagacgtg tgctcttccg atctccatcc tcctgccctc t    51

<210> SEQ ID NO 191
<211> LENGTH: 22
<212> TYPE: DNA
<213> ORGANISM: Artificial Sequence
<220> FEATURE:
<223> OTHER INFORMATION: Synthetic(Forward primer used for targeted deep sequencing captured by Digenome-seq (OT19, 1st PCR))

<400> SEQUENCE: 191
gacagcactt agggatgatg aa    22

<210> SEQ ID NO 192
<211> LENGTH: 19
<212> TYPE: DNA
<213> ORGANISM: Artificial Sequence
<220> FEATURE:
<223> OTHER INFORMATION: Synthetic(Reverse primer used for targeted deep sequencing captured by Digenome-seq (OT19, 1st PCR))

<400> SEQUENCE: 192
gatggagctg cccaagaaa    19

<210> SEQ ID NO 193
<211> LENGTH: 53
<212> TYPE: DNA
<213> ORGANISM: Artificial Sequence
<220> FEATURE:
<223> OTHER INFORMATION: Synthetic(Forward primer used for targeted deep sequencing captured by Digenome-seq (OT19, 2nd PCR))

<400> SEQUENCE: 193
acactctttc cctacacgac gctcttccga tctgggatga tgaatggctg gat    53

<210> SEQ ID NO 194
<211> LENGTH: 54
<212> TYPE: DNA
<213> ORGANISM: Artificial Sequence
<220> FEATURE:
<223> OTHER INFORMATION: Synthetic(Reverse primer used for targeted deep sequencing captured by Digenome-seq (OT19, 2nd PCR))

<400> SEQUENCE: 194
gtgactggag ttcagacgtg tgctcttccg atctcttctc catgtaggtg cctt    54

<210> SEQ ID NO 195
<211> LENGTH: 22
<212> TYPE: DNA
<213> ORGANISM: Artificial Sequence
<220> FEATURE:
<223> OTHER INFORMATION: Synthetic(Forward primer used for targeted deep sequencing captured by Digenome-seq (OT20, 1st PCR))

<400> SEQUENCE: 195
cctgagaaca aggagtgtca ag    22

<210> SEQ ID NO 196
<211> LENGTH: 21

<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT20, 1st PCR))

<400> SEQUENCE: 196
ccatggaatg cccagatagt t                                           21

<210> SEQ ID NO 197
<211> LENGTH: 57
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT20, 2nd PCR))

<400> SEQUENCE: 197
acactctttc cctacacgac gctcttccga tctgttgata tcccagctta agcaatc    57

<210> SEQ ID NO 198
<211> LENGTH: 57
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT20, 2nd PCR))

<400> SEQUENCE: 198
gtgactggag ttcagacgtg tgctcttccg atctttaaac atcatttctg gcacgtc    57

<210> SEQ ID NO 199
<211> LENGTH: 24
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT21, 1st PCR))

<400> SEQUENCE: 199
agctattgct gtcaatctct tact                                        24

<210> SEQ ID NO 200
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT21, 1st PCR))

<400> SEQUENCE: 200
tacccagtct caggtagttc tt                                          22

<210> SEQ ID NO 201
<211> LENGTH: 58
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT21, 2nd PCR))

<400> SEQUENCE: 201
acactctttc cctacacgac gctcttccga tcttgctgtc aatctcttac tgtaacta   58

<210> SEQ ID NO 202
<211> LENGTH: 56
<212> TYPE: DNA

```
<213> ORGANISM: Artificial Sequence
<220> FEATURE:
<223> OTHER INFORMATION: Synthetic(Reverse primer used for targeted deep
      sequencing captured by Digenome-seq (OT21, 2nd PCR))

<400> SEQUENCE: 202
gtgactggag ttcagacgtg tgctcttccg atcttagcaa tgcgagaaca gactaa        56

<210> SEQ ID NO 203
<211> LENGTH: 21
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT22, 1st PCR))

<400> SEQUENCE: 203
tgccacacat cccatcatat c                                              21

<210> SEQ ID NO 204
<211> LENGTH: 20
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT22, 1st PCR))

<400> SEQUENCE: 204
cagcagacac agactcacaa                                                20

<210> SEQ ID NO 205
<211> LENGTH: 56
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT22, 2nd PCR))

<400> SEQUENCE: 205
acactctttc cctacacgac gctcttccga tctcaacatg aaatgccaga gtcaaa        56

<210> SEQ ID NO 206
<211> LENGTH: 58
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT22, 2nd PCR))

<400> SEQUENCE: 206
gtgactggag ttcagacgtg tgctcttccg atctcccatt caagttgcaa tcactatc      58

<210> SEQ ID NO 207
<211> LENGTH: 24
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT23, 1st PCR))

<400> SEQUENCE: 207
tcctgaaaga agggataagg taag                                           24

<210> SEQ ID NO 208
<211> LENGTH: 21
<212> TYPE: DNA
<213> ORGANISM: Artificial Sequence
```

<220> FEATURE:
<223> OTHER INFORMATION: Synthetic(Reverse primer used for targeted deep
      sequencing captured by Digenome-seq (OT23, 1st PCR))

<400> SEQUENCE: 208
tgaggatggg tttcggtaaa t                                              21

<210> SEQ ID NO 209
<211> LENGTH: 54
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT23, 2nd PCR))

<400> SEQUENCE: 209
acactctttc cctacacgac gctcttccga tctataaggt aagctcagcc tgtc          54

<210> SEQ ID NO 210
<211> LENGTH: 56
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT23, 2nd PCR))

<400> SEQUENCE: 210
gtgactggag ttcagacgtg tgctcttccg atctgtttca acatgaaggc aaggag        56

<210> SEQ ID NO 211
<211> LENGTH: 25
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT24, 1st PCR))

<400> SEQUENCE: 211
caagaagggt gttaggttat gaaag                                          25

<210> SEQ ID NO 212
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT24, 1st PCR))

<400> SEQUENCE: 212
acagtcaacc cttaaggaag ag                                             22

<210> SEQ ID NO 213
<211> LENGTH: 59
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT24, 2nd PCR))

<400> SEQUENCE: 213
acactctttc cctacacgac gctcttccga tctgggtgtt aggttatgaa agtttaagg     59

<210> SEQ ID NO 214
<211> LENGTH: 56
<212> TYPE: DNA
<213> ORGANISM: Artificial Sequence
<220> FEATURE:

```
<223> OTHER INFORMATION: Synthetic(Reverse primer used for targeted deep
      sequencing captured by Digenome-seq (OT24, 2nd PCR))

<400> SEQUENCE: 214
gtgactggag ttcagacgtg tgctcttccg atctaaggaa gagttgtctt cactcg        56

<210> SEQ ID NO 215
<211> LENGTH: 24
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT25, 1st PCR))

<400> SEQUENCE: 215
ctttcacagc cagtcacaaa taaa                                            24

<210> SEQ ID NO 216
<211> LENGTH: 26
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT25, 1st PCR))

<400> SEQUENCE: 216
ctcacactct aggaaacaga tgatag                                          26

<210> SEQ ID NO 217
<211> LENGTH: 57
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT25, 2nd PCR))

<400> SEQUENCE: 217
acactctttc cctacacgac gctcttccga tctcaatcca ctcagactac agagaaa       57

<210> SEQ ID NO 218
<211> LENGTH: 56
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT25, 2nd PCR))

<400> SEQUENCE: 218
gtgactggag ttcagacgtg tgctcttccg atctagacag gagtgttctc caaatc        56

<210> SEQ ID NO 219
<211> LENGTH: 20
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT26, 1st PCR))

<400> SEQUENCE: 219
gtgagccaag atcacaccat                                                 20

<210> SEQ ID NO 220
<211> LENGTH: 21
<212> TYPE: DNA
<213> ORGANISM: Artificial Sequence
<220> FEATURE:
<223> OTHER INFORMATION: Synthetic(Reverse primer used for targeted deep
``` sequencing captured by Digenome-seq (OT26, 1st PCR))

<400> SEQUENCE: 220
ctctcagcaa gaaggcagat t                                           21

<210> SEQ ID NO 221
<211> LENGTH: 53
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT26, 2nd PCR))

<400> SEQUENCE: 221
acactctttc cctacacgac gctcttccga tctagatcac accattgcac tcc         53

<210> SEQ ID NO 222
<211> LENGTH: 55
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT26, 2nd PCR))

<400> SEQUENCE: 222
gtgactggag ttcagacgtg tgctcttccg atctgccaga tcagtgtctg ctaaa        55

<210> SEQ ID NO 223
<211> LENGTH: 20
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT27, 1st PCR))

<400> SEQUENCE: 223
ggacacgctg agtcaaagtt                                             20

<210> SEQ ID NO 224
<211> LENGTH: 21
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT27, 1st PCR))

<400> SEQUENCE: 224
cctttccttc gtgctgattg a                                           21

<210> SEQ ID NO 225
<211> LENGTH: 53
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT27, 2nd PCR))

<400> SEQUENCE: 225
acactctttc cctacacgac gctcttccga tctgcaacca cgtcgacaat aca         53

<210> SEQ ID NO 226
<211> LENGTH: 56
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT27, 2nd PCR))

<400> SEQUENCE: 226
gtgactggag ttcagacgtg tgctcttccg atctggtgga agtgacaagc aagtta        56

<210> SEQ ID NO 227
<211> LENGTH: 22
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT28, 1st PCR))

<400> SEQUENCE: 227
cccaacaatt ccttctttga gc        22

<210> SEQ ID NO 228
<211> LENGTH: 23
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT28, 1st PCR))

<400> SEQUENCE: 228
tctgctatta gaggaggcta gaa        23

<210> SEQ ID NO 229
<211> LENGTH: 57
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT28, 2nd PCR))

<400> SEQUENCE: 229
acactctttc cctacacgac gctcttccga tctcaattcc ttctttgagc tcactat        57

<210> SEQ ID NO 230
<211> LENGTH: 54
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT28, 2nd PCR))

<400> SEQUENCE: 230
gtgactggag ttcagacgtg tgctcttccg atctgaggct agaacaacct tgga        54

<210> SEQ ID NO 231
<211> LENGTH: 23
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT29, 1st PCR))

<400> SEQUENCE: 231
gggcaaatcc ataacccaga ata        23

<210> SEQ ID NO 232
<211> LENGTH: 20
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT29, 1st PCR))

<400> SEQUENCE: 232
aggcgatgca tgagcttaaa        20

<210> SEQ ID NO 233
<211> LENGTH: 53
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT29, 2nd PCR))

<400> SEQUENCE: 233
acactctttc cctacacgac gctcttccga tctgggcaaa tccataaccc aga        53

<210> SEQ ID NO 234
<211> LENGTH: 57
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT29, 2nd PCR))

<400> SEQUENCE: 234
gtgactggag ttcagacgtg tgctcttccg atctgtagct aatctggcta ccatcac        57

<210> SEQ ID NO 235
<211> LENGTH: 19
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT30, 1st PCR))

<400> SEQUENCE: 235
attggctggc acacagtag        19

<210> SEQ ID NO 236
<211> LENGTH: 22
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT30, 1st PCR))

<400> SEQUENCE: 236
cccaggatct agcaaacatt ca        22

<210> SEQ ID NO 237
<211> LENGTH: 57
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT30, 2nd PCR))

<400> SEQUENCE: 237
acactctttc cctacacgac gctcttccga tcttgaatga atgaaggaaa gaatggg        57

<210> SEQ ID NO 238
<211> LENGTH: 57
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT30, 2nd PCR))

<400> SEQUENCE: 238
gtgactggag ttcagacgtg tgctcttccg atctgcaaac attcatcttt cgagcta        57

<210> SEQ ID NO 239
<211> LENGTH: 20
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT31, 1st PCR))

<400> SEQUENCE: 239
cacttctcgc ctttgacctt        20

<210> SEQ ID NO 240
<211> LENGTH: 20
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT31, 1st PCR))

<400> SEQUENCE: 240
tggctgtgct cactttactg        20

<210> SEQ ID NO 241
<211> LENGTH: 54
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT31, 2nd PCR))

<400> SEQUENCE: 241
acactctttc cctacacgac gctcttccga tctagaggag gaaactggag ctta        54

<210> SEQ ID NO 242
<211> LENGTH: 53
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT31, 2nd PCR))

<400> SEQUENCE: 242
gtgactggag ttcagacgtg tgctcttccg atctactttta ctgccaccag tgc        53

<210> SEQ ID NO 243
<211> LENGTH: 21
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT32, 1st PCR))

<400> SEQUENCE: 243
atcttccaca ggtgcaaatc t        21

<210> SEQ ID NO 244
<211> LENGTH: 18
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT32, 1st PCR))

<400> SEQUENCE: 244
ttgcctatgg ctgccttg                                                    18

<210> SEQ ID NO 245
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT32, 2nd PCR))

<400> SEQUENCE: 245
acactctttc cctacacgac gctcttccga tctctggtca ttctcttccg tcaaa          55

<210> SEQ ID NO 246
<211> LENGTH: 54
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT32, 2nd PCR))

<400> SEQUENCE: 246
gtgactggag ttcagacgtg tgctcttccg atctaacagt atgggcctga aaag           54

<210> SEQ ID NO 247
<211> LENGTH: 22
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT33, 1st PCR))

<400> SEQUENCE: 247
catgtaacca cgactacctc aa                                               22

<210> SEQ ID NO 248
<211> LENGTH: 19
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT33, 1st PCR))

<400> SEQUENCE: 248
ccatggcttg cagcaattt                                                   19

<210> SEQ ID NO 249
<211> LENGTH: 59
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT33, 2nd PCR))

<400> SEQUENCE: 249
acactctttc cctacacgac gctcttccga tctgtaacca cgactacctc aagatataa      59

<210> SEQ ID NO 250
<211> LENGTH: 56
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT33, 2nd PCR))

<400> SEQUENCE: 250
gtgactggag ttcagacgtg tgctcttccg atctcacaca gacgtactgt aagga          56

<210> SEQ ID NO 251
<211> LENGTH: 26
<212> TYPE: DNA
<213> ORGANISM: Artificial Sequence
<220> FEATURE:
<223> OTHER INFORMATION: Synthetic(Forward primer used for targeted deep
sequencing captured by Digenome-seq (OT34, 1st PCR))

<400> SEQUENCE: 251
cttagaggaa agagaactgg gattat                                          26

<210> SEQ ID NO 252
<211> LENGTH: 23
<212> TYPE: DNA
<213> ORGANISM: Artificial Sequence
<220> FEATURE:
<223> OTHER INFORMATION: Synthetic(Reverse primer used for targeted deep
sequencing captured by Digenome-seq (OT34, 1st PCR))

<400> SEQUENCE: 252
agtgtggctg attatggtga tta                                             23

<210> SEQ ID NO 253
<211> LENGTH: 57
<212> TYPE: DNA
<213> ORGANISM: Artificial Sequence
<220> FEATURE:
<223> OTHER INFORMATION: Synthetic(Forward primer used for targeted deep
sequencing captured by Digenome-seq (OT34, 2nd PCR))

<400> SEQUENCE: 253
acactctttc cctacacgac gctcttccga tctccaagag tagcctaacc tttacaa        57

<210> SEQ ID NO 254
<211> LENGTH: 55
<212> TYPE: DNA
<213> ORGANISM: Artificial Sequence
<220> FEATURE:
<223> OTHER INFORMATION: Synthetic(Reverse primer used for targeted deep
sequencing captured by Digenome-seq (OT34, 2nd PCR))

<400> SEQUENCE: 254
gtgactggag ttcagacgtg tgctcttccg atctcacgta aattgcacct gtcac          55

<210> SEQ ID NO 255
<211> LENGTH: 22
<212> TYPE: DNA
<213> ORGANISM: Artificial Sequence
<220> FEATURE:
<223> OTHER INFORMATION: Synthetic(Forward primer used for targeted deep
sequencing captured by Digenome-seq (OT35, 1st PCR))

<400> SEQUENCE: 255
tttctctgcc attcttcctc tg                                              22

<210> SEQ ID NO 256
<211> LENGTH: 22
<212> TYPE: DNA
<213> ORGANISM: Artificial Sequence
<220> FEATURE:
<223> OTHER INFORMATION: Synthetic(Reverse primer used for targeted deep
sequencing captured by Digenome-seq (OT35, 1st PCR))

<400> SEQUENCE: 256
gaatgaagac acgaggcatt tg                                              22

<210> SEQ ID NO 257
<211> LENGTH: 53
<212> TYPE: DNA
<213> ORGANISM: Artificial Sequence
<220> FEATURE:
<223> OTHER INFORMATION: Synthetic(Forward primer used for targeted deep sequencing captured by Digenome-seq (OT35, 2nd PCR))

<400> SEQUENCE: 257
acactctttc cctacacgac gctcttccga tcttcttagc ccatgttgct tcc        53

<210> SEQ ID NO 258
<211> LENGTH: 56
<212> TYPE: DNA
<213> ORGANISM: Artificial Sequence
<220> FEATURE:
<223> OTHER INFORMATION: Synthetic(Reverse primer used for targeted deep sequencing captured by Digenome-seq (OT35, 2nd PCR))

<400> SEQUENCE: 258
gtgactggag ttcagacgtg tgctcttccg atcttccaga atgtaccttg cactttt    56

<210> SEQ ID NO 259
<211> LENGTH: 22
<212> TYPE: DNA
<213> ORGANISM: Artificial Sequence
<220> FEATURE:
<223> OTHER INFORMATION: Synthetic(Forward primer used for targeted deep sequencing captured by Digenome-seq (OT36, 1st PCR))

<400> SEQUENCE: 259
tgctgtcttt agttccttca tt                                          22

<210> SEQ ID NO 260
<211> LENGTH: 20
<212> TYPE: DNA
<213> ORGANISM: Artificial Sequence
<220> FEATURE:
<223> OTHER INFORMATION: Synthetic(Reverse primer used for targeted deep sequencing captured by Digenome-seq (OT36, 1st PCR))

<400> SEQUENCE: 260
ttaacccagc atcagctctc                                             20

<210> SEQ ID NO 261
<211> LENGTH: 55
<212> TYPE: DNA
<213> ORGANISM: Artificial Sequence
<220> FEATURE:
<223> OTHER INFORMATION: Synthetic(Forward primer used for targeted deep sequencing captured by Digenome-seq (OT36, 2nd PCR))

<400> SEQUENCE: 261
acactctttc cctacacgac gctcttccga tcttgctgtc tttagttcct tcatt      55

<210> SEQ ID NO 262
<211> LENGTH: 54
<212> TYPE: DNA
<213> ORGANISM: Artificial Sequence
<220> FEATURE:
<223> OTHER INFORMATION: Synthetic(Reverse primer used for targeted deep sequencing captured by Digenome-seq (OT36, 2nd PCR))

<400> SEQUENCE: 262
gtgactggag ttcagacgtg tgctcttccg atctttaacc cagcatcagc tctc       54

-continued

```
<210> SEQ ID NO 263
<211> LENGTH: 20
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT37, 1st PCR))

<400> SEQUENCE: 263
tttccagaag agccgacaag                                                 20

<210> SEQ ID NO 264
<211> LENGTH: 20
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT37, 1st PCR))

<400> SEQUENCE: 264
ccaacaacca ccacgactaa                                                 20

<210> SEQ ID NO 265
<211> LENGTH: 51
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT37, 2nd PCR))

<400> SEQUENCE: 265
acactctttc cctacacgac gctcttccga tctgggccct tctgctttga g              51

<210> SEQ ID NO 266
<211> LENGTH: 54
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT37, 2nd PCR))

<400> SEQUENCE: 266
gtgactggag ttcagacgtg tgctcttccg atctagtctc ccatgaaggc tgta           54

<210> SEQ ID NO 267
<211> LENGTH: 24
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT38, 1st PCR))

<400> SEQUENCE: 267
aaagtacata gaggacgtgc atag                                            24

<210> SEQ ID NO 268
<211> LENGTH: 19
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT38, 1st PCR))

<400> SEQUENCE: 268
agttcaccac caccacaag                                                  19

<210> SEQ ID NO 269
```

```
<211> LENGTH: 55
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT38, 2nd PCR))

<400> SEQUENCE: 269
acactctttc cctacacgac gctcttccga tcttgtgcaa atactacgcc atttc            55

<210> SEQ ID NO 270
<211> LENGTH: 55
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT38, 2nd PCR))

<400> SEQUENCE: 270
gtgactggag ttcagacgtg tgctcttccg atctacaagt ttgcacttgc tttca            55

<210> SEQ ID NO 271
<211> LENGTH: 18
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT39, 1st PCR))

<400> SEQUENCE: 271
cacctggacc accagaaa                                                     18

<210> SEQ ID NO 272
<211> LENGTH: 19
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT39, 1st PCR))

<400> SEQUENCE: 272
gctgtttgca aatgcctca                                                    19

<210> SEQ ID NO 273
<211> LENGTH: 51
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT39, 2nd PCR))

<400> SEQUENCE: 273
acactctttc cctacacgac gctcttccga tctcacctgg accaccagaa a                51

<210> SEQ ID NO 274
<211> LENGTH: 54
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT39, 2nd PCR))

<400> SEQUENCE: 274
gtgactggag ttcagacgtg tgctcttccg atctacccat ctctgcagac ctta             54

<210> SEQ ID NO 275
<211> LENGTH: 24
```

```
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT40, 1st PCR))

<400> SEQUENCE: 275
ctgatttcct gagtttctcc ctaa                                           24

<210> SEQ ID NO 276
<211> LENGTH: 19
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT40, 1st PCR))

<400> SEQUENCE: 276
aagtgtgggc tgtgcataa                                                 19

<210> SEQ ID NO 277
<211> LENGTH: 57
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT40, 2nd PCR))

<400> SEQUENCE: 277
acactctttc cctacacgac gctcttccga tctctgtgaa gggatttcaa actttcc       57

<210> SEQ ID NO 278
<211> LENGTH: 55
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT40, 2nd PCR))

<400> SEQUENCE: 278
gtgactggag ttcagacgtg tgctcttccg atctcgatca aggctaacgt catca         55

<210> SEQ ID NO 279
<211> LENGTH: 21
<212> TYPE: DNA
<213> ORGANISM: Artificial Sequence
<220> FEATURE:
<223> OTHER INFORMATION: Synthetic(Forward primer used for targeted deep
      sequencing captured by Digenome-seq (OT41, 1st PCR))

<400> SEQUENCE: 279
catctcctgc tgtgtcatct t                                              21

<210> SEQ ID NO 280
<211> LENGTH: 23
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT41, 1st PCR))

<400> SEQUENCE: 280
ccagtctcgg gtatgtcttt att                                            23

<210> SEQ ID NO 281
<211> LENGTH: 55
<212> TYPE: DNA
```

-continued

<213> ORGANISM: Artificial Sequence
<220> FEATURE:
<223> OTHER INFORMATION: Synthetic(Forward primer used for targeted deep
      sequencing captured by Digenome-seq (OT41, 2nd PCR))

<400> SEQUENCE: 281
acactctttc cctacacgac gctcttccga tctgactgac ttccatcttc ctcac      55

<210> SEQ ID NO 282
<211> LENGTH: 58
<212> TYPE: DNA
<213> ORGANISM: Artificial Sequence
<220> FEATURE:
<223> OTHER INFORMATION: Synthetic(Reverse primer used for targeted deep
      sequencing captured by Digenome-seq (OT41, 2nd PCR))

<400> SEQUENCE: 282
gtgactggag ttcagacgtg tgctcttccg atctcagact aatacatccg gtctcatc   58

<210> SEQ ID NO 283
<211> LENGTH: 20
<212> TYPE: DNA
<213> ORGANISM: Artificial Sequence
<220> FEATURE:
<223> OTHER INFORMATION: Synthetic(Forward primer used for qPCR (mouse
      vegfa)

<400> SEQUENCE: 283
acgtcagaga gcaacatcac                                              20

<210> SEQ ID NO 284
<211> LENGTH: 23
<212> TYPE: DNA
<213> ORGANISM: Artificial Sequence
<220> FEATURE:
<223> OTHER INFORMATION: Synthetic(Reverse primer used for qPCR (mouse
      vegfa)

<400> SEQUENCE: 284
ctgtctttct ttggtctgca ttc                                          23

<210> SEQ ID NO 285
<211> LENGTH: 22
<212> TYPE: DNA
<213> ORGANISM: Artificial Sequence
<220> FEATURE:
<223> OTHER INFORMATION: Synthetic(Forward primer used for qPCR (mouse
      gapdh)

<400> SEQUENCE: 285
gctgagtatg tcgtggagtc ta                                           22

<210> SEQ ID NO 286
<211> LENGTH: 20
<212> TYPE: DNA
<213> ORGANISM: Artificial Sequence
<220> FEATURE:
<223> OTHER INFORMATION: Synthetic(Reverse primer used for qPCR (mouse
      gapdh)

<400> SEQUENCE: 286
gtggttcaca cccatcacaa                                              20

<210> SEQ ID NO 287
<211> LENGTH: 22
<212> TYPE: DNA
<213> ORGANISM: Artificial Sequence
<220> FEATURE:
<223> OTHER INFORMATION: Synthetic(Forward primer used for qPCR (human vegfa-1)

<400> SEQUENCE: 287
cgagtacatc ttcaagccat cc                                    22

<210> SEQ ID NO 288
<211> LENGTH: 22
<212> TYPE: DNA
<213> ORGANISM: Artificial Sequence
<220> FEATURE:
<223> OTHER INFORMATION: Synthetic(Reverse primer used for qPCR (human vegfa-1)

<400> SEQUENCE: 288
ggtgaggttt gatccgcata at                                    22

<210> SEQ ID NO 289
<211> LENGTH: 19
<212> TYPE: DNA
<213> ORGANISM: Artificial Sequence
<220> FEATURE:
<223> OTHER INFORMATION: Synthetic(Forward primer used for qPCR (human vegfa-2)

<400> SEQUENCE: 289
agaaggagga gggcagaat                                        19

<210> SEQ ID NO 290
<211> LENGTH: 22
<212> TYPE: DNA
<213> ORGANISM: Artificial Sequence
<220> FEATURE:
<223> OTHER INFORMATION: Synthetic(Reverse primer used for qPCR (human vegfa-2)

<400> SEQUENCE: 290
cacaggatgg cttgaagatg ta                                    22

<210> SEQ ID NO 291
<211> LENGTH: 20
<212> TYPE: DNA
<213> ORGANISM: Artificial Sequence
<220> FEATURE:
<223> OTHER INFORMATION: Synthetic(Forward primer used for qPCR (human gapdh)

<400> SEQUENCE: 291
caatgacccc ttcattgacc                                       20

<210> SEQ ID NO 292
<211> LENGTH: 20
<212> TYPE: DNA
<213> ORGANISM: Artificial Sequence
<220> FEATURE:
<223> OTHER INFORMATION: Synthetic(Reverse primer used for qPCR (human gapdh)

<400> SEQUENCE: 292
ttgattttgg agggatctcg                                       20

<210> SEQ ID NO 293
<211> LENGTH: 23
<212> TYPE: DNA
<213> ORGANISM: Artificial Sequence
<220> FEATURE:

<223> OTHER INFORMATION: Synthetic(Target sequence of sgRNA with PAM
    (Vegfa-1 gene))

<400> SEQUENCE: 293
ctcctggaag atgtccacca ggg                                              23

<210> SEQ ID NO 294
<211> LENGTH: 23
<212> TYPE: DNA
<213> ORGANISM: Artificial Sequence
<220> FEATURE:
<223> OTHER INFORMATION: Synthetic(Target sequence of sgRNA with PAM
    (Vegfa-2 gene))

<400> SEQUENCE: 294
agctcatctc tcctatgtgc tgg                                              23

<210> SEQ ID NO 295
<211> LENGTH: 23
<212> TYPE: DNA
<213> ORGANISM: Artificial Sequence
<220> FEATURE:
<223> OTHER INFORMATION: Synthetic(Target sequence of sgRNA with PAM
    (Vegfa-3 gene))

<400> SEQUENCE: 295
gaccctggtg gacatcttcc agg                                              23

<210> SEQ ID NO 296
<211> LENGTH: 23
<212> TYPE: DNA
<213> ORGANISM: Artificial Sequence
<220> FEATURE:
<223> OTHER INFORMATION: Synthetic(Target sequence of sgRNA with PAM
    (Vegfa-4 gene))

<400> SEQUENCE: 296
actcctggaa gatgtccacc agg                                              23

<210> SEQ ID NO 297
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
    sgRNA with PAM in mouse genome (OT1))

<400> SEQUENCE: 297
ctcctggaag attttcacca ggg                                              23

<210> SEQ ID NO 298
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
    sgRNA with PAM in mouse genome (OT2))

<400> SEQUENCE: 298
ctcctggaag atctccagga agg                                              23

<210> SEQ ID NO 299
<211> LENGTH: 23
<212> TYPE: DNA
<213> ORGANISM: Artificial Sequence
<220> FEATURE:
<223> OTHER INFORMATION: Synthetic(Potential off-target site of Vegfa-1 sgRNA with PAM in mouse genome (OT3))

<400> SEQUENCE: 299
ctcctggaag aggttctcca ggg                                        23

<210> SEQ ID NO 300
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT4))

<400> SEQUENCE: 300
ctcttggcag atgtccacaa ggg                                        23

<210> SEQ ID NO 301
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT5))

<400> SEQUENCE: 301
ctcctggaag ctgcccatca tgg                                        23

<210> SEQ ID NO 302
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT6))

<400> SEQUENCE: 302
ctcctggaaa atgcccaccc tgg                                        23

<210> SEQ ID NO 303
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT7))

<400> SEQUENCE: 303
ctcctggaag atgtgggcca tgg                                        23

<210> SEQ ID NO 304
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT8))

<400> SEQUENCE: 304
ctcctgaaag ctgaccacca cgg                                        23

<210> SEQ ID NO 305
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT9))

```
<400> SEQUENCE: 305
cacatggagg atgtccacca tgg                                          23

<210> SEQ ID NO 306
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT10))

<400> SEQUENCE: 306
ctcctggaag ctgttgacca ggg                                          23

<210> SEQ ID NO 307
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT11))

<400> SEQUENCE: 307
ctcctggaag aggacaacca agg                                          23

<210> SEQ ID NO 308
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT12))

<400> SEQUENCE: 308
ctgctggatg ttgtccacca ggg                                          23

<210> SEQ ID NO 309
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT13))

<400> SEQUENCE: 309
ctcctggaag ttgtcctcct tgg                                          23

<210> SEQ ID NO 310
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT14))

<400> SEQUENCE: 310
cccctggaag atttccatca agg                                          23

<210> SEQ ID NO 311
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT15))
```

```
<400> SEQUENCE: 311
ctcttggcag ctgtccacca tgg                                             23

<210> SEQ ID NO 312
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT16))

<400> SEQUENCE: 312
ctccaagaag atgtcctcca tgg                                             23

<210> SEQ ID NO 313
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT17))

<400> SEQUENCE: 313
ctcctggaag atgtcctgga agg                                             23

<210> SEQ ID NO 314
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT18))

<400> SEQUENCE: 314
ctcctggtag atgttcagca tgg                                             23

<210> SEQ ID NO 315
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT19))

<400> SEQUENCE: 315
gtcctggaag ctgtccacaa agg                                             23

<210> SEQ ID NO 316
<211> LENGTH: 23
<212> TYPE: DNA
<213> ORGANISM: Artificial Sequence
<220> FEATURE:
<223> OTHER INFORMATION: Synthetic(Potential off-target site of Vegfa-1
      sgRNA with PAM in mouse genome (OT20))

<400> SEQUENCE: 316
ctcagtgaag atgtccacca agg                                             23

<210> SEQ ID NO 317
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT1))
```

```
<400> SEQUENCE: 317
atcctgtaag acatccaccc tgg                                              23

<210> SEQ ID NO 318
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT2))

<400> SEQUENCE: 318
ttgctggaag atgtccccct tgg                                              23

<210> SEQ ID NO 319
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT3))

<400> SEQUENCE: 319
tacctggaag aattccacca cgg                                              23

<210> SEQ ID NO 320
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT4))

<400> SEQUENCE: 320
gcctgggaag atgtccacca ggg                                              23

<210> SEQ ID NO 321
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT5))

<400> SEQUENCE: 321
ttccaggaag aaatccacca tgg                                              23

<210> SEQ ID NO 322
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT6))

<400> SEQUENCE: 322
acaatagaag aagtccacca tgg                                              23

<210> SEQ ID NO 323
<211> LENGTH: 23
<212> TYPE: DNA
<213> ORGANISM: Artificial Sequence
```

```
<220> FEATURE:
<223> OTHER INFORMATION: Synthetic(In vitro cleavage site in human
      genome identified by Digenome-seq using the VEGFA sgRNA with PAM
      (OT7))

<400> SEQUENCE: 323
ctccaggaag ttctccacca agg                                            23

<210> SEQ ID NO 324
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT8))

<400> SEQUENCE: 324
aattaataag atgtccacct acg                                            23

<210> SEQ ID NO 325
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT9))

<400> SEQUENCE: 325
gtcctggaag atgagcacca agg                                            23

<210> SEQ ID NO 326
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT10))

<400> SEQUENCE: 326
gtgatggaag atgtccactt agg                                            23

<210> SEQ ID NO 327
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT11))

<400> SEQUENCE: 327
ctccaggaag atttccatca tgg                                            23

<210> SEQ ID NO 328
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT12))

<400> SEQUENCE: 328
gtcctggagg atttccacca ggg                                            23
```

<210> SEQ ID NO 329
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT13))

<400> SEQUENCE: 329
gtccagaaag atatccacct agg                                              23

<210> SEQ ID NO 330
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT14))

<400> SEQUENCE: 330
cacctggaag atttccacct tgg                                              23

<210> SEQ ID NO 331
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT15))

<400> SEQUENCE: 331
ctactggaag aggtccaccc tgg                                              23

<210> SEQ ID NO 332
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT16))

<400> SEQUENCE: 332
ctactgggag aagtccacct tgg                                              23

<210> SEQ ID NO 333
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT17))

<400> SEQUENCE: 333
cttcaggaag atgtccacaa tgg                                              23

<210> SEQ ID NO 334
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT18))

```
<400> SEQUENCE: 334
ctcccggaag ctgtccaccc tgg                                           23

<210> SEQ ID NO 335
<211> LENGTH: 24
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT19))

<400> SEQUENCE: 335
gactcctgaa gatgtacacc ctgg                                          24

<210> SEQ ID NO 336
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT20))

<400> SEQUENCE: 336
gaactggatg atgtccacct tgg                                           23

<210> SEQ ID NO 337
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT21))

<400> SEQUENCE: 337
gccttggaag atgtccctca tgg                                           23

<210> SEQ ID NO 338
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT22))

<400> SEQUENCE: 338
ctccttgaaa gagtccaccc agg                                           23

<210> SEQ ID NO 339
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT23))

<400> SEQUENCE: 339
ctcctgcaag atgtcctcca gga                                           23

<210> SEQ ID NO 340
<211> LENGTH: 23
<212> TYPE: DNA
```

<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT24))

<400> SEQUENCE: 340
ggcctggaaa atgtccaccg tgg                                           23

<210> SEQ ID NO 341
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT25))

<400> SEQUENCE: 341
tcatggaaga tattccacca ggg                                           23

<210> SEQ ID NO 342
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT26))

<400> SEQUENCE: 342
aagatggaag acatccacca ggg                                           23

<210> SEQ ID NO 343
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT27))

<400> SEQUENCE: 343
cagctggaag atgtccacct ttg                                           23

<210> SEQ ID NO 344
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT28))

<400> SEQUENCE: 344
cagctggaag atgtccacca cga                                           23

<210> SEQ ID NO 345
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT29))

<400> SEQUENCE: 345
ctcctggaag gagtccacca tga                                           23

<210> SEQ ID NO 346
<211> LENGTH: 23
<212> TYPE: DNA
<213> ORGANISM: Artificial Sequence
<220> FEATURE:
<223> OTHER INFORMATION: Synthetic(In vitro cleavage site in human
genome identified by Digenome-seq using the VEGFA sgRNA with PAM
(OT30))

<400> SEQUENCE: 346
tactcctggg atctccaccc atg                                        23

<210> SEQ ID NO 347
<211> LENGTH: 23
<212> TYPE: DNA
<213> ORGANISM: Artificial Sequence
<220> FEATURE:
<223> OTHER INFORMATION: Synthetic(In vitro cleavage site in human
genome identified by Digenome-seq using the VEGFA sgRNA with PAM
(OT31))

<400> SEQUENCE: 347
cgtctgaaag atgtccacca cgc                                        23

<210> SEQ ID NO 348
<211> LENGTH: 23
<212> TYPE: DNA
<213> ORGANISM: Artificial Sequence
<220> FEATURE:
<223> OTHER INFORMATION: Synthetic(In vitro cleavage site in human
genome identified by Digenome-seq using the VEGFA sgRNA with PAM
(OT32))

<400> SEQUENCE: 348
ggtctggaag atgtcaacca cag                                        23

<210> SEQ ID NO 349
<211> LENGTH: 23
<212> TYPE: DNA
<213> ORGANISM: Artificial Sequence
<220> FEATURE:
<223> OTHER INFORMATION: Synthetic(In vitro cleavage site in human
genome identified by Digenome-seq using the VEGFA sgRNA with PAM
(OT33))

<400> SEQUENCE: 349
ctcctggtca atatccaccc aag                                        23

<210> SEQ ID NO 350
<211> LENGTH: 23
<212> TYPE: DNA
<213> ORGANISM: Artificial Sequence
<220> FEATURE:
<223> OTHER INFORMATION: Synthetic(In vitro cleavage site in human
genome identified by Digenome-seq using the VEGFA sgRNA with PAM
(OT34))

<400> SEQUENCE: 350
ccctggaaga atgtccacca gga                                        23

<210> SEQ ID NO 351
<211> LENGTH: 23
<212> TYPE: DNA
<213> ORGANISM: Artificial Sequence
<220> FEATURE:
<223> OTHER INFORMATION: Synthetic(In vitro cleavage site in human
genome identified by Digenome-seq using the VEGFA sgRNA with PAM (OT35))

<400> SEQUENCE: 351
tgcctgaaag acatccacca agg                                           23

<210> SEQ ID NO 352
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT36))

<400> SEQUENCE: 352
tgacaggaag atgtccaccc atg                                           23

<210> SEQ ID NO 353
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT37))

<400> SEQUENCE: 353
cctcctgctg atgtccaccc agg                                           23

<210> SEQ ID NO 354
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT38))

<400> SEQUENCE: 354
gctcctggaa gaatccacca cag                                           23

<210> SEQ ID NO 355
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT39))

<400> SEQUENCE: 355
cagctgggag atgtccacca tga                                           23

<210> SEQ ID NO 356
<211> LENGTH: 23
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT40))

<400> SEQUENCE: 356
ttgggggaag aagtccacca agg                                           23

<210> SEQ ID NO 357
<211> LENGTH: 23

```
<212> TYPE: DNA
<213> ORGANISM: Artificial Sequence
<220> FEATURE:
<223> OTHER INFORMATION: Synthetic(In vitro cleavage site in human
      genome identified by Digenome-seq using the VEGFA sgRNA with PAM
      (OT41))

<400> SEQUENCE: 357
ccctaggaag aggtccacca ggg                                             23

<210> SEQ ID NO 358
<211> LENGTH: 4107
<212> TYPE: DNA
<213> ORGANISM: Artificial Sequence
<220> FEATURE:
<223> OTHER INFORMATION: Synthetic(Cas9 conding sequence)

<400> SEQUENCE: 358
atggacaaga agtacagcat cggcctggac atcggtacca acagcgtggg ctgggccgtg      60
atcaccgacg agtacaaggt gcccagcaag aagttcaagg tgctgggcaa caccgaccgc     120
cacagcatca agaagaacct gatcggcgcc ctgctgttcg acagcggcga gaccgccgag     180
gccacccgcc tgaagcgcac cgcccgccgc cgctacaccc gccgcaagaa ccgcatctgc     240
tacctgcagg agatcttcag caacgagatg gccaaggtgg acgacagctt cttccaccgc     300
ctggaggaga gcttcctggt ggaggaggac aagaagcacg agcgccaccc catcttcggc     360
aacatcgtgg acgaggtggc ctaccacgag aagtacccca ccatctacca cctgcgcaag     420
aagctggtgg acagcaccga caaggccgac ctgcgcctga tctacctggc cctggcccac     480
atgatcaagt tccgcggcca cttcctgatc gagggcgacc tgaaccccga caacagcgac     540
gtggacaagc tgttcatcca gctggtgcag acctacaacc agctgttcga ggagaacccc     600
atcaacgcca gcggcgtgga cgccaaggcc atcctgagcg cccgcctgag caagagccgc     660
cgcctggaga acctgatcgc ccagctgccc ggcgagaaga gaacggcct gttcggcaac     720 ctgatcgccc tgagcctggg cctgaccccc aacttcaaga gcaacttcga cctggccgag     780
gacgccaagc tgcagctgag caaggacacc tacgacgacg acctggacaa cctgctggcc     840
cagatcggcg accagtacgc cgacctgttc ctggccgcca gaacctgag cgacgccatc     900 ctgctgagcg acatcctgcg cgtgaacacc gagatcacca aggcccccct gagcgccagc     960
atgatcaagc gctacgacga gcaccaccag gacctgaccc tgctgaaggc cctggtgcgc    1020
cagcagctgc ccgagaagta caaggagatc ttcttcgacc agagcaagaa cggctacgcc    1080
ggctacatcg acggcggcgc cagccaggag gagttctaca agttcatcaa gcccatcctg    1140
gagaagatgg acggcaccga ggagctgctg gtgaagctga accgcgagga cctgctgcgc    1200
aagcagcgca ccttcgacaa cggcagcatc ccccaccaga tccacctggg cgagctgcac    1260
gccatcctgc gccgccagga ggacttctac cccttcctga ggacaaccg cgagaagatc    1320 gagaagatct gaccttccg catccctac tacgtgggcc cctggcccg cggcaacagc    1380 cgcttcgcct ggatgacccg caagagcgag gagaccatca cccctggaa cttcgaggag    1440 gtggtggaca agggcgccag cgcccagagc ttcatcgagc gcatgaccaa cttcgacaag    1500
aacctgccca acgagaaggt gctgcccaag cacagcctgc tgtacgagta cttcaccgtg    1560
tacaacgagc tgaccaaggt gaagtacgtg accgagggca tgcgcaagcc cgccttcctg    1620
agcggcgagc agaagaaggc catcgtggac ctgctgttca gaccaaccg caaggtgacc    1680 gtgaagcagc tgaaggagga ctacttcaag aagatcgagt gcttcgacag cgtggagatc    1740
```

-continued

```
agcggcgtgg aggaccgctt caacgccagc ctgggcacct accacgacct gctgaagatc    1800
atcaaggaca aggacttcct ggacaacgag gagaacgagg acatcctgga ggacatcgtg    1860
ctgaccctga ccctgttcga ggaccgcgag atgatcgagg agcgcctgaa gacctacgcc    1920
cacctgttcg acgacaaggt gatgaagcag ctgaagcgcc gccgctacac cggctggggc    1980
cgcctgagcc gcaagcttat caacggcatc cgcgacaagc agagcggcaa gaccatcctg    2040
gacttcctga gagcgacgg cttcgccaac cgcaacttca tgcagctgat ccacgacgac    2100
agcctgacct tcaaggagga catccagaag gcccaggtga gcggccaggg cgacagcctg    2160
cacgagcaca tcgccaacct ggccggcagc ccgccatca agaagggcat cctgcagacc     2220
gtgaaggtgg tggacgagct ggtgaaggtg atgggccgcc acaagcccga gaacatcgtg    2280
atcgagatgg cccgcgagaa ccagaccacc cagaagggcc agaagaacag ccgcgagcgc    2340
atgaagcgca tcgaggaggg catcaaggag ctgggcagcc agatcctgaa ggagcacccc    2400
gtggagaaca cccagctgca gaacgagaag ctgtacctgt actacctgca gaacggccgc    2460
gacatgtacg tggaccagga gctggacatc aaccgcctga gcgactacga cgtggaccac    2520
atcgtgcccc agagcttcct gaaggacgac agcatcgaca caaggtgct gacccgcagc    2580
gacaagaacc gcggcaagag cgacaacgtg cccagcgagg aggtggtgaa gaagatgaag    2640
aactactggc gccagctgct gaacgccaag ctgatcaccc agcgcaagtt cgacaacctg    2700
accaaggccc agcgcggcgg cctgagcgag ctggacaagg ccggcttcat caagcgccag    2760
ctggtggaga cccgccagat caccaagcac gtggcccaga tcctggacag ccgcatgaac    2820
accaagtacg acgagaacga caagctgatc cgcgaggtga aggtgatcac cctgaagagc    2880
aagctggtga gcgacttccg caaggacttc cagttctaca aggtgcgcga gatcaacaac    2940
taccaccacg cccacgacgc ctacctgaac gccgtggtgg gcaccgccct gatcaagaag    3000
taccccaagc tggagagcga gttcgtgtac ggcgactaca aggtgtacga cgtgcgcaag    3060
atgatcgcca gagcgagca ggagatcggc aaggccaccg ccaagtactt cttctacagc     3120
aacatcatga acttcttcaa gaccgagatc accctggcca acggcgagat ccgcaagcgc    3180
cccctgatcg agaccaacgg cgagaccggc gagatcgtgt gggacaaggg ccgcgacttc    3240
gccaccgtgc gcaaggtgct gagcatgccc caggtgaaca tcgtgaagaa gaccgaggtg    3300
cagaccggcg gcttcagcaa ggagagcatc ctgcccaagc gcaacagcga caagctgatc    3360
gcccgcaaga aggactggga ccccaagaag tacggcggct cgacagccc caccgtggcc    3420
tacagcgtgc tggtggtggc caaggtggag aagggcaaga gcaagaagct gaagagcgtg    3480
aaggagctgc tgggcatcac catcatggag cgcagcagct tcgagaagaa ccccatcgac    3540
ttcctggagg ccaagggcta caaggaggtg aagaaggacc tgatcatcaa gctgcccaag    3600
tacagcctgt tcgagctgga gaacggccgc aagcgcatgc tggccagcgc cggcgagctg    3660
cagaagggca cgagctggc cctgcccagc aagtacgtga acttcctgta cctggccagc    3720
cactacgaga agctgaaggg cagccccgag gacaacgagc agaagcagct gttcgtggag    3780
cagcacaagc actacctgga cgagatcatc gagcagatca gcgagttcag caagcgcgtg    3840
atcctggccg acgccaacct ggacaaggtg ctgagcgcct acaacaagca ccgcgacaag    3900
cccatccgcg agcaggccga gaacatcatc caccctgttca ccctgaccaa cctgggcgcc    3960
cccgccgcct tcaagtactt cgacaccacc atcgaccgca gcgctacac cagcaccaag    4020
gaggtgctga cgccaccct gatccaccag agcatcaccg gtctgtacga gacccgcatc    4080
gacctgagcc agctgggcgg cgactaa                                        4107
```

<210> SEQ ID NO 359
<211> LENGTH: 12
<212> TYPE: RNA
<213> ORGANISM: Artificial Sequence
<220> FEATURE:
<223> OTHER INFORMATION: Synthetic(Essential part of crRNA)

<400> SEQUENCE: 359
guuuuagagc ua                                               12

<210> SEQ ID NO 360
<211> LENGTH: 10
<212> TYPE: RNA
<213> ORGANISM: Artificial Sequence
<220> FEATURE:
<223> OTHER INFORMATION: Synthetic(3' end part of crRNA)

<400> SEQUENCE: 360
ugcuguuuug                                                  10

<210> SEQ ID NO 361
<211> LENGTH: 60
<212> TYPE: RNA
<213> ORGANISM: Artificial Sequence
<220> FEATURE:
<223> OTHER INFORMATION: Synthetic(Essential part of tracrRNA)

<400> SEQUENCE: 361
uagcaaguua aauaaggcu aguccguuau caacuugaaa aaguggcacc gagucggugc    60

<210> SEQ ID NO 362
<211> LENGTH: 50
<212> TYPE: DNA
<213> ORGANISM: Artificial Sequence
<220> FEATURE:
<223> OTHER INFORMATION: Synthetic_oligonucleotide

<400> SEQUENCE: 362
ctcgtcgggg tactcctgga agatgtccac cagggtctca atcggacggc             50

<210> SEQ ID NO 363
<211> LENGTH: 50
<212> TYPE: DNA
<213> ORGANISM: Artificial Sequence
<220> FEATURE:
<223> OTHER INFORMATION: Synthetic_oligonucleotide

<400> SEQUENCE: 363
ctcatcaggg tactcctgga agatgtccac cagggtctcg attggatggc             50

<210> SEQ ID NO 364
<211> LENGTH: 51
<212> TYPE: DNA
<213> ORGANISM: Artificial Sequence
<220> FEATURE:
<223> OTHER INFORMATION: Synthetic_oligonucleotide

<400> SEQUENCE: 364
ctcgtcgggg tactcctgga agatgtccaa ccagggtctc aatcggacgg c           51

<210> SEQ ID NO 365
<211> LENGTH: 47
<212> TYPE: DNA
<213> ORGANISM: Artificial Sequence
<220> FEATURE:

<223> OTHER INFORMATION: Synthetic_oligonucleotide

<400> SEQUENCE: 365
ctcgtcgggg tactcctgga agatgtccag ggtctcaatc ggacggc        47

<210> SEQ ID NO 366
<211> LENGTH: 13
<212> TYPE: DNA
<213> ORGANISM: Artificial Sequence
<220> FEATURE:
<223> OTHER INFORMATION: Synthetic_oligonucleotide

<400> SEQUENCE: 366
ctcgtcggac ggc        13

<210> SEQ ID NO 367
<211> LENGTH: 49
<212> TYPE: DNA
<213> ORGANISM: Artificial Sequence
<220> FEATURE:
<223> OTHER INFORMATION: Synthetic_oligonucleotide

<400> SEQUENCE: 367
ctcgtcgggg tactcctgga agatgtcacc agggtctcaa tcggacggc        49

<210> SEQ ID NO 368
<211> LENGTH: 40
<212> TYPE: DNA
<213> ORGANISM: Artificial Sequence
<220> FEATURE:
<223> OTHER INFORMATION: Synthetic_oligonucleotide

<400> SEQUENCE: 368
ctcgtcgggg tactcctgga agatgtctca atcggacggc        40

<210> SEQ ID NO 369
<211> LENGTH: 51
<212> TYPE: DNA
<213> ORGANISM: Artificial Sequence
<220> FEATURE:
<223> OTHER INFORMATION: Synthetic_oligonucleotide

<400> SEQUENCE: 369
ctcatcaggg tactcctgga agatgtccaa ccagggtctc gattggatgg c        51

<210> SEQ ID NO 370
<211> LENGTH: 47
<212> TYPE: DNA
<213> ORGANISM: Artificial Sequence
<220> FEATURE:
<223> OTHER INFORMATION: Synthetic_oligonucleotide

<400> SEQUENCE: 370
ctcatcaggg tactcctgga agatgtccag ggtctcgatt ggatggc        47

<210> SEQ ID NO 371
<211> LENGTH: 49
<212> TYPE: DNA
<213> ORGANISM: Artificial Sequence
<220> FEATURE:
<223> OTHER INFORMATION: Synthetic_oligonucleotide

<400> SEQUENCE: 371
ctcatcaggg tactcctgga agatgtcccc agggtctcga ttggatggc        49

<210> SEQ ID NO 372
<211> LENGTH: 51
<212> TYPE: DNA
<213> ORGANISM: Artificial Sequence
<220> FEATURE:
<223> OTHER INFORMATION: Synthetic_oligonucleotide

<400> SEQUENCE: 372
ctcatcaggg tactcctgga agatgtccat ccagggtctc gattggatgg c    51

<210> SEQ ID NO 373
<211> LENGTH: 42
<212> TYPE: DNA
<213> ORGANISM: Artificial Sequence
<220> FEATURE:
<223> OTHER INFORMATION: Synthetic_oligonucleotide

<400> SEQUENCE: 373
ctcatcaggg tactcctgga agatgtctct cgattggatg gc    42

<210> SEQ ID NO 374
<211> LENGTH: 40
<212> TYPE: DNA
<213> ORGANISM: Artificial Sequence
<220> FEATURE:
<223> OTHER INFORMATION: Synthetic_oligonucleotide

<400> SEQUENCE: 374
ctcgtcgggg tactcctgga agatgtctca atcggacggc    40

<210> SEQ ID NO 375
<211> LENGTH: 40
<212> TYPE: DNA
<213> ORGANISM: Artificial Sequence
<220> FEATURE:
<223> OTHER INFORMATION: Synthetic_oligonucleotide

<400> SEQUENCE: 375
ctcgtcgggg tactcctgga agatgtctca atcggacggc    40

<210> SEQ ID NO 376
<211> LENGTH: 38
<212> TYPE: DNA
<213> ORGANISM: Artificial Sequence
<220> FEATURE:
<223> OTHER INFORMATION: Synthetic_oligonucleotide

<400> SEQUENCE: 376
ctcgtcgggg tactcctgga gggtctcaat cggacggc    38

<210> SEQ ID NO 377
<211> LENGTH: 40
<212> TYPE: DNA
<213> ORGANISM: Artificial Sequence
<220> FEATURE:
<223> OTHER INFORMATION: Synthetic_oligonucleotide

<400> SEQUENCE: 377
ctcgtcgggg tactcctgga agatgtctca atcggacggc    40

<210> SEQ ID NO 378
<211> LENGTH: 47
<212> TYPE: DNA
<213> ORGANISM: Artificial Sequence
<220> FEATURE:
<223> OTHER INFORMATION: Synthetic_oligonucleotide

<400> SEQUENCE: 378
ctcgtcgggg tactcctgga agatgtccag ggtctcaatc ggacggc 47

<210> SEQ ID NO 379
<211> LENGTH: 49
<212> TYPE: DNA
<213> ORGANISM: Artificial Sequence
<220> FEATURE:
<223> OTHER INFORMATION: Synthetic_oligonucleotide

<400> SEQUENCE: 379
ctcgtcgggg tactcctgga agatgtcacc agggtctcaa tcggacggc 49

<210> SEQ ID NO 380
<211> LENGTH: 48
<212> TYPE: DNA
<213> ORGANISM: Artificial Sequence
<220> FEATURE:
<223> OTHER INFORMATION: Synthetic_oligonucleotide

<400> SEQUENCE: 380
ctcgtcgggg tactcctgga agatgtccca gggtctcaat cggacggc 48

<210> SEQ ID NO 381
<211> LENGTH: 49
<212> TYPE: DNA
<213> ORGANISM: Artificial Sequence
<220> FEATURE:
<223> OTHER INFORMATION: Synthetic_oligonucleotide

<400> SEQUENCE: 381
ctcgtcgggg tactcctgga agatgtcccc agggtctcaa tcggacggc 49

<210> SEQ ID NO 382
<211> LENGTH: 48
<212> TYPE: DNA
<213> ORGANISM: Artificial Sequence
<220> FEATURE:
<223> OTHER INFORMATION: Synthetic_oligonucleotide

<400> SEQUENCE: 382
ctcgtcgggg tactcctgga agatgtccaa gggtctcaat cggacggc 48

<210> SEQ ID NO 383
<211> LENGTH: 50
<212> TYPE: DNA
<213> ORGANISM: Artificial Sequence
<220> FEATURE:
<223> OTHER INFORMATION: Synthetic_oligonucleotide

<400> SEQUENCE: 383
tcccaggccc agggcggtcc tcagaagcca ggaggcagca gagaactccc 50

<210> SEQ ID NO 384
<211> LENGTH: 49
<212> TYPE: DNA
<213> ORGANISM: Artificial Sequence
<220> FEATURE:
<223> OTHER INFORMATION: Synthetic_oligonucleotide

<400> SEQUENCE: 384
tcccaggccc agggcggtcc tcagaagccg gaggcagcag agaactccc 49

<210> SEQ ID NO 385
<211> LENGTH: 51

```
<212> TYPE: DNA
<213> ORGANISM: Artificial Sequence
<220> FEATURE:
<223> OTHER INFORMATION: Synthetic_oligonucleotide

<400> SEQUENCE: 385
tcccaggccc agggcggtcc tcagaagccc aggaggcagc agagaactcc c      51

<210> SEQ ID NO 386
<211> LENGTH: 42
<212> TYPE: DNA
<213> ORGANISM: Artificial Sequence
<220> FEATURE:
<223> OTHER INFORMATION: Synthetic_oligonucleotide

<400> SEQUENCE: 386
tcccaggccc agggcggtcc taggaggcag cagagaactc cc                42

<210> SEQ ID NO 387
<211> LENGTH: 49
<212> TYPE: DNA
<213> ORGANISM: Artificial Sequence
<220> FEATURE:
<223> OTHER INFORMATION: Synthetic_oligonucleotide

<400> SEQUENCE: 387
tcccaggccc agggcggtcc tcagaagcag gaggcagcag agaactccc         49

<210> SEQ ID NO 388
<211> LENGTH: 43
<212> TYPE: DNA
<213> ORGANISM: Artificial Sequence
<220> FEATURE:
<223> OTHER INFORMATION: Synthetic_oligonucleotide

<400> SEQUENCE: 388
tcccaggccc agggcggtcc tcagaagcca gcagagaact ccc               43

<210> SEQ ID NO 389
<211> LENGTH: 50
<212> TYPE: DNA
<213> ORGANISM: Artificial Sequence
<220> FEATURE:
<223> OTHER INFORMATION: Synthetic_oligonucleotide

<400> SEQUENCE: 389
gagcagcccc atgaggacct tctacaggtg gtcccagagt tagcctgccg        50

<210> SEQ ID NO 390
<211> LENGTH: 50
<212> TYPE: DNA
<213> ORGANISM: Artificial Sequence
<220> FEATURE:
<223> OTHER INFORMATION: Synthetic_oligonucleotide

<400> SEQUENCE: 390
gagtagtccc atgaggacct tctacaggtg gtcccagagc taacctaccg        50
```